United States Patent
Belding et al.

(10) Patent No.: US 12,239,454 B2
(45) Date of Patent: Mar. 4, 2025

(54) COMMUNICATION AND USER INTERFACE CONTROL IN USER ACTIVITY MONITORING SYSTEMS

(71) Applicant: T.J.Smith & Nephew, Limited, Hull (GB)

(72) Inventors: Jonathan Edward Mika Belding, Dorchester (GB); Johannes Dagevos van Rij, Skidby (GB); Allan Kenneth Frazer Grugeon Hunt, Beverley (GB); Jonathon Simon Lay, Beckenham (GB); Brian William Quist, Andover, MA (US); Damian Lawson Smith, Swanland (GB)

(73) Assignee: T.J.Smith and Nephew, Limited, Hull (GB)

( * ) Notice: Subject to any disclaimer, the term of this patent is extended or adjusted under 35 U.S.C. 154(b) by 748 days.

(21) Appl. No.: 17/607,233

(22) PCT Filed: Apr. 16, 2020

(86) PCT No.: PCT/EP2020/060687
§ 371 (c)(1),
(2) Date: Oct. 28, 2021

(87) PCT Pub. No.: WO2020/221595
PCT Pub. Date: Nov. 5, 2020

(65) Prior Publication Data
US 2022/0218271 A1 Jul. 14, 2022

(30) Foreign Application Priority Data

May 1, 2019 (GB) .................................. 1906090
May 1, 2019 (GB) .................................. 1906092

(Continued)

(51) Int. Cl.
*A61B 5/00* (2006.01)
*A43B 3/48* (2022.01)
(Continued)

(52) U.S. Cl.
CPC ................ *A61B 5/447* (2013.01); *A43B 3/48* (2022.01); *A61B 5/0004* (2013.01);
(Continued)

(58) Field of Classification Search
CPC ..... A61B 5/447; A61B 5/0004; A61B 5/0022; A61B 5/1036; A61B 5/1112;
(Continued)

(56) References Cited

U.S. PATENT DOCUMENTS 3,974,491 A 8/1976 Sipe
4,610,253 A 9/1986 Rosenberg
(Continued)

FOREIGN PATENT DOCUMENTS

CN 105631195 B 12/2017
CN 110025316 A 7/2019
(Continued)

OTHER PUBLICATIONS

Abbott Diabetes Care Ltd., "FreeStyle Libre Flash Glucose Monitoring System—User's Manual," Mar. 2014, 124 pages.
(Continued)

*Primary Examiner* — May A Abouelela
(74) *Attorney, Agent, or Firm* — Knobbe, Martens, Olson & Bear, LLP

(57) ABSTRACT

In some aspects, a non-transitory computer readable medium is disclosed that has an application stored thereon that when executed by a processor of an electronic device causes the processor to perform a process. The process can include receiving motion data from a motion sensor, the motion data being indicative of motion by a user while (Continued)

wearing the motion sensor. The process can also include transmitting the motion data to a server, receiving from the server a time that the motion data indicates a foot of the user experienced a loading force which risked adversely impacting an existing foot ulcer or causing a new foot ulcer, determining a geographic location of the motion sensor at the time that the foot experienced the loading force, displaying the time and the geographic location, and requesting that the user identify an activity engaged in by the user at the time and the geographic location.

23 Claims, 32 Drawing Sheets

(30) Foreign Application Priority Data

May 1, 2019 (GB) .................................. 1906095
May 1, 2019 (GB) .................................. 1906097

(51) Int. Cl.
| | | |
|---|---|---|
| A61B 5/103 | (2006.01) | |
| A61B 5/11 | (2006.01) | |
| G06F 3/14 | (2006.01) | |
| G16H 40/67 | (2018.01) | |
| H04W 4/029 | (2018.01) | |
| H04W 4/38 | (2018.01) | |
| G06F 3/0482 | (2013.01) | |
| G06F 3/0484 | (2022.01) | |

(52) U.S. Cl.
CPC .......... *A61B 5/0022* (2013.01); *A61B 5/1036* (2013.01); *A61B 5/1112* (2013.01); *A61B 5/1123* (2013.01); *A61B 5/6807* (2013.01); *A61B 5/7275* (2013.01); *A61B 5/742* (2013.01); *G06F 3/14* (2013.01); *G16H 40/67* (2018.01); *H04W 4/029* (2018.02); *H04W 4/38* (2018.02); *A61B 2562/0219* (2013.01); *A61B 2562/0223* (2013.01); *G06F 3/0482* (2013.01); *G06F 3/0484* (2013.01)

(58) Field of Classification Search
CPC ... A61B 5/1123; A61B 5/6807; A61B 5/7275; A61B 5/742; A61B 2562/0219; A61B 2562/0223; A61B 5/0024; A61B 5/4833; A61B 5/6833; A61B 5/6812; A61B 5/6828; A61B 5/1118; A43B 3/48; A43B 3/02; A43B 3/34; A43B 7/147; G06F 3/14; G06F 3/0482; G06F 3/0484; G16H 40/67; H04W 4/029; H04W 4/38

See application file for complete search history.

(56) References Cited

U.S. PATENT DOCUMENTS

| | | | |
|---|---|---|---|
| 5,107,854 A | 4/1992 | Knotts et al. | |
| 5,253,654 A | 10/1993 | Thomas et al. | |
| 5,642,096 A | 6/1997 | Leyerer et al. | |
| 5,875,571 A | 3/1999 | Huang | |
| 5,879,292 A | 3/1999 | Sternberg et al. | |
| 6,031,463 A | 2/2000 | Bechmann | |
| 6,282,448 B1 | 8/2001 | Katz et al. | |
| 6,287,253 B1 | 9/2001 | Ortega et al. | |
| 6,571,193 B1 | 5/2003 | Unuma et al. | |
| 6,602,191 B2 | 8/2003 | Quy | |
| 7,616,110 B2 | 11/2009 | Crump et al. | |
| 7,996,177 B2 | 8/2011 | Tatsuta et al. | |
| 7,998,092 B2 | 8/2011 | Avni et al. | |
| 8,111,165 B2 | 2/2012 | Ortega et al. | |
| 8,280,682 B2 | 10/2012 | Vock et al. | |
| 8,388,553 B2 | 3/2013 | James et al. | |
| 8,753,275 B2 | 6/2014 | Najafi et al. | |
| 8,925,392 B2 | 1/2015 | Esposito et al. | |
| 8,976,062 B2 | 3/2015 | Park et al. | |
| 9,220,455 B2 | 12/2015 | Sarrafzadeh et al. | |
| 9,251,685 B2 | 2/2016 | Patil et al. | |
| 9,338,819 B2 | 5/2016 | Meng et al. | |
| 9,427,179 B2 | 8/2016 | Mestrovic et al. | |
| 9,439,599 B2 | 9/2016 | Thompson et al. | |
| 9,629,585 B2 | 4/2017 | Das et al. | |
| 9,693,691 B2 | 7/2017 | Johnson | |
| 9,861,550 B2 | 1/2018 | Ribble et al. | |
| 9,907,103 B2 | 2/2018 | Chen et al. | |
| 9,972,116 B2 | 5/2018 | Sano et al. | |
| 10,019,555 B2 | 7/2018 | Manice et al. | |
| 10,085,675 B2 | 10/2018 | Nagasaki et al. | |
| 10,127,357 B2 | 11/2018 | Whiting et al. | |
| 10,166,164 B2 | 1/2019 | Johnson et al. | |
| 10,274,305 B2 | 4/2019 | Huang et al. | |
| 10,335,636 B2 | 7/2019 | Holma et al. | |
| 11,497,964 B1* | 11/2022 | Hunter | A63B 53/005 |
| 12,114,995 B2 | 10/2024 | Walgreen et al. | |
| 2003/0088294 A1 | 5/2003 | Gesotti | |
| 2004/0102931 A1 | 5/2004 | Ellis et al. | |
| 2005/0099294 A1 | 5/2005 | Bogner et al. | |
| 2005/0165284 A1 | 7/2005 | Gefen | |
| 2006/0052678 A1 | 3/2006 | Drinan et al. | |
| 2007/0173903 A1 | 7/2007 | Goren et al. | |
| 2008/0096726 A1 | 4/2008 | Riley et al. | |
| 2008/0216593 A1 | 9/2008 | Jacobsen et al. | |
| 2008/0242945 A1 | 10/2008 | Gugliotti et al. | |
| 2008/0287832 A1 | 11/2008 | Collins et al. | |
| 2009/0069727 A1 | 3/2009 | Neustaedter et al. | |
| 2009/0070939 A1 | 3/2009 | Hann | |
| 2009/0209830 A1* | 8/2009 | Nagle | A61B 5/445 |
| | | | 600/301 |
| 2009/0234249 A1 | 9/2009 | Randolph | |
| 2009/0234262 A1 | 9/2009 | Reid, Jr. et al. | |
| 2009/0292194 A1 | 11/2009 | Libbus et al. | |
| 2010/0056873 A1 | 3/2010 | Allen et al. | |
| 2010/0099956 A1 | 4/2010 | Cole et al. | |
| 2010/0162832 A1 | 7/2010 | Brauers | |
| 2010/0198022 A1 | 8/2010 | Vuillerme et al. | |
| 2010/0225476 A1 | 9/2010 | Klose | |
| 2010/0298742 A1 | 11/2010 | Perlman et al. | |
| 2010/0324455 A1 | 12/2010 | Rangel et al. | |
| 2011/0054359 A1 | 3/2011 | Sazonov et al. | |
| 2011/0130697 A1 | 6/2011 | Nagle et al. | |
| 2011/0214501 A1 | 9/2011 | Ross et al. | |
| 2011/0263950 A1 | 10/2011 | Larson et al. | |
| 2012/0010535 A1 | 1/2012 | Kubiak et al. | |
| 2012/0109013 A1* | 5/2012 | Everett | A61B 5/1036 |
| | | | 600/587 |
| 2012/0184878 A1* | 7/2012 | Najafi | A61B 5/4833 |
| | | | 600/592 |
| 2012/0185267 A1 | 7/2012 | Kamen et al. | |
| 2012/0238914 A1 | 9/2012 | Goldfield et al. | |
| 2012/0259651 A1 | 10/2012 | Mallon et al. | |
| 2012/0290217 A1 | 11/2012 | Shoval et al. | |
| 2013/0023720 A1 | 1/2013 | Solomon et al. | |
| 2013/0167848 A1 | 7/2013 | Frassica et al. | |
| 2013/0213145 A1 | 8/2013 | Owings et al. | |
| 2013/0282324 A1 | 10/2013 | Carter et al. | |
| 2013/0317753 A1 | 11/2013 | Kamen et al. | |
| 2014/0039840 A1 | 2/2014 | Yuen et al. | |
| 2014/0089673 A1 | 3/2014 | Luna | |
| 2014/0107932 A1 | 4/2014 | Luna | |
| 2014/0135657 A1 | 5/2014 | Wu et al. | |
| 2014/0188499 A1 | 7/2014 | Bell et al. | |
| 2014/0200486 A1 | 7/2014 | Bechtel et al. | |
| 2014/0203797 A1 | 7/2014 | Stivoric et al. | |
| 2014/0221787 A1 | 8/2014 | Teller et al. | |
| 2014/0235166 A1 | 8/2014 | Molettiere et al. | |
| 2014/0303460 A1 | 10/2014 | Corley et al. | |
| 2014/0350435 A1 | 11/2014 | Lam | |
| 2014/0372147 A1 | 12/2014 | White | |
| 2014/0378786 A1 | 12/2014 | Hong et al. | |
| 2015/0094545 A1 | 4/2015 | Russell et al. | |

(56) References Cited

U.S. PATENT DOCUMENTS

| | | | |
|---|---|---|---|
| 2015/0125839 A1 | 5/2015 | Tillges et al. | |
| 2015/0182843 A1 | 7/2015 | Esposito et al. | |
| 2015/0190059 A1* | 7/2015 | Petersen | A61B 5/0022 |
| | | | 600/549 |
| 2016/0092651 A1 | 3/2016 | Austin et al. | |
| 2016/0120433 A1 | 5/2016 | Hughes et al. | |
| 2016/0135731 A1 | 5/2016 | Drennan | |
| 2016/0213924 A1 | 7/2016 | Coleman et al. | |
| 2016/0228050 A1 | 8/2016 | Sugla et al. | |
| 2016/0256080 A1 | 9/2016 | Shen et al. | |
| 2016/0275776 A1 | 9/2016 | Shen et al. | |
| 2016/0292509 A1 | 10/2016 | Kaps et al. | |
| 2016/0296144 A1 | 10/2016 | Gaddam et al. | |
| 2016/0317083 A1 | 11/2016 | DeLuke et al. | |
| 2016/0317084 A1 | 11/2016 | DeLuke et al. | |
| 2016/0331322 A1 | 11/2016 | Son et al. | |
| 2016/0367192 A1 | 12/2016 | Iyengar et al. | |
| 2017/0011210 A1 | 1/2017 | Cheong et al. | |
| 2017/0027498 A1* | 2/2017 | Larson | A61B 5/447 |
| 2017/0027529 A1* | 2/2017 | Frieder | H04W 52/0254 |
| 2017/0046503 A1 | 2/2017 | Cho et al. | |
| 2017/0055851 A1* | 3/2017 | Al-Ali | A61B 5/1117 |
| 2017/0056724 A1* | 3/2017 | Baker | G01S 19/19 |
| 2017/0079868 A1* | 3/2017 | Reid, Jr. | A61B 5/6812 |
| 2017/0160400 A1* | 6/2017 | Larbi | A61B 5/445 |
| 2017/0188841 A1* | 7/2017 | Ma | G01K 3/14 |
| 2017/0199972 A1 | 7/2017 | Hussam et al. | |
| 2017/0225033 A1 | 8/2017 | Czaja | |
| 2017/0231015 A1 | 8/2017 | Jang et al. | |
| 2017/0281073 A1 | 10/2017 | Drennan et al. | |
| 2017/0347899 A1 | 12/2017 | Bhushan et al. | |
| 2017/0367644 A1 | 12/2017 | Sharman et al. | |
| 2018/0000407 A1 | 1/2018 | Johnson et al. | |
| 2018/0018864 A1 | 1/2018 | Baker | |
| 2018/0020931 A1 | 1/2018 | Shusterman | |
| 2018/0025146 A1 | 1/2018 | Vasyltsov et al. | |
| 2018/0074547 A1* | 3/2018 | Smadi | H02J 7/0045 |
| 2018/0132287 A1 | 5/2018 | Cheng et al. | |
| 2018/0185558 A1 | 7/2018 | Weston | |
| 2018/0271409 A1 | 9/2018 | Gong et al. | |
| 2018/0360157 A1 | 12/2018 | Jeong et al. | |
| 2019/0082771 A1 | 3/2019 | Shin et al. | |
| 2019/0209777 A1* | 7/2019 | O'Connell | A63B 24/0062 |
| 2019/0313913 A1* | 10/2019 | Fu | G16H 40/67 |
| 2020/0034123 A1* | 1/2020 | Fagundes | G06F 3/0482 |
| 2020/0229765 A1* | 7/2020 | Peabody | A61B 5/6824 |
| 2020/0297244 A1* | 9/2020 | Brownhill | A61B 5/6802 |
| 2021/0100496 A1* | 4/2021 | Hartwell | A61B 5/4538 |
| 2023/0157897 A1 | 5/2023 | Engel et al. | |

FOREIGN PATENT DOCUMENTS

| | | |
|---|---|---|
| DE | 19612334 A1 | 1/1997 |
| DE | 102013013013 A1 | 2/2015 |
| DE | 102014222955 A1 | 5/2016 |
| EP | 2675315 B1 | 5/2020 |
| EP | 3962360 A1 | 3/2022 |
| GB | 2439750 A | 1/2008 |
| IN | 342014 | 8/2014 |
| JP | 2005245709 A | 9/2005 |
| JP | 2013085611 A | 5/2013 |
| JP | 2014046151 A | 3/2014 |
| WO | WO-2005121729 A1 | 12/2005 |
| WO | WO-2011113070 A1 | 9/2011 |
| WO | WO-2013064852 A1 | 5/2013 |
| WO | WO-2014178755 A1 | 11/2014 |
| WO | WO-2016018448 A1 | 2/2016 |
| WO | WO-2016109744 A1 | 7/2016 |
| WO | WO-2016154230 A1 | 9/2016 |
| WO | WO-2016180073 A1 | 11/2016 |
| WO | WO-2016186904 A1 | 11/2016 |
| WO | WO-2017048979 A1 | 3/2017 |
| WO | WO-2017205728 A1 | 11/2017 |
| WO | WO-2017214188 A1 | 12/2017 |
| WO | WO-2018096390 A1 | 5/2018 |
| WO | WO-2018144946 A1 | 8/2018 |
| WO | WO-2018159851 A1 | 9/2018 |
| WO | WO-2018162736 A1 | 9/2018 |
| WO | WO-2019042790 A1 | 3/2019 |
| WO | WO-2019096828 A1 | 5/2019 |
| WO | WO-2019162272 A1 | 8/2019 |
| WO | WO-2019234011 A1 | 12/2019 |
| WO | WO-2019238927 A1 | 12/2019 |
| WO | WO-2019243171 A1 | 12/2019 |

OTHER PUBLICATIONS

Amjadi M., et al., "Ultra-Stretchable and Skin-Mountable Strain Sensors Using Carbon Nanotubes-Ecoflex Nanocomposites," Nanotechnology, Institute of Physics Publishing, vol. 26, No. 37, Aug. 25, 2015, 11 pages.

Centauri Medical, Inc., "DynaSense—Instructions for Use," Document No. 1312AJ (User Manual), Jul. 2013, 54 pages.

Crews R., et al., "A Method for Assessing Off-loading Compliance," Journal of the American Podiatric Medical Association, vol. 99 (2), Mar./Apr. 2009, 6 pages.

Crews R., et al., "Role and Determinants of Adherence to Offloading in Diabetic Foot Ulcer Healing: A Prospective Investigation," Diabetes Care, vol. 39, Aug. 2016, pp. 1371-1377 (7 pages).

Fitbit, "Introducing Fitbit Coach," YouTube, retrieved from https://www.youtube.com/watch?v=QDYxWeQMrAw, Oct. 24, 2017, 1 page.

Hanft J., et al., "A Guide To Preventative Offloading Of Diabetic Foot Ulcers," Podiatry Today, Nov. 2011, retrieved from www.podiatrytoday.com/guide-preventative-offloading-diabetic-foot-ulcers, 8 pages.

International Search Report and Written Opinion for Application No. PCT/EP2020/060687, mailed on Jul. 15, 2020, 18 pages.

Kosecki D., "9 Things You Need to Know About Your New Fitbit Coach Subscription," Fitbit, Dec. 22, 2017, retrieved from https://blog.fitbit.com/new-fitbit-coach/, 12 pages.

Muscillo R., et al., "An Adaptive Kalman-Based Bayes Estimation Technique To Classify Locomotor Activities In Young And Elderly Adults Through Accelerometers," Medical Engineering & Physics, Butterworth-Heinemann, GB, vol. 32, No. 8, Oct. 1, 2010 (Oct. 1, 2010), pp. 849-859, XP027267622, ISSN:1350-4533 [retrieved on Jun. 23, 2010] the whole document.

Nakamoto., H., et al., "Stretchable Strain Sensor with Anisotropy and Application for Joint Angle Measurement," IEEE Sensors Journal, vol. 16, No. 10, May 2016, pp. 3572-3579.

Raviglione A., et al., "Real-Time Smart Textile-Based System to Monitor Pressure Offloading of Diabetic Foot Ulcers," Journal of Diabetes Science and Technology, vol. 11, Sep. 2017, 5 pages.

Smith and Nephew Medical Ltd., "Sandy 2012980—Healthcare Professional User Manual," Jul. 2018, retrieved from https://apps.fcc.gov/oetcf/eas/reports/ViewExhibitReport.cfm?mode=ExhibitscalledFromFrame=N&application_id=f%2FbhDROytnS96PwjOmDTNA%3D%3D&fcc_id=2AEAJ-2012980, retrieved on Aug. 22, 2018, 8 pages.

Tairych A., et al., "Distributed Sensing: Multiple Capacitive Stretch Sensors on a Single Channel," Proceedings of SPIE, vol. 10163, Apr. 17, 2017, pp. 1016306-1-1016306-10.

Votzke C., et al., "Highly-Stretchable Biomechanical Strain Sensor Using Printed Liquid Metal Paste," IEEE Biomedical Circuits and Systems Conference (BIOCAS), Oct. 17, 2018, XP033483141, 4 pages.

International Preliminary Report on Patentability for Application No. PCT/EP2020/060687, mailed on Nov. 11, 2021, 11 pages.

* cited by examiner

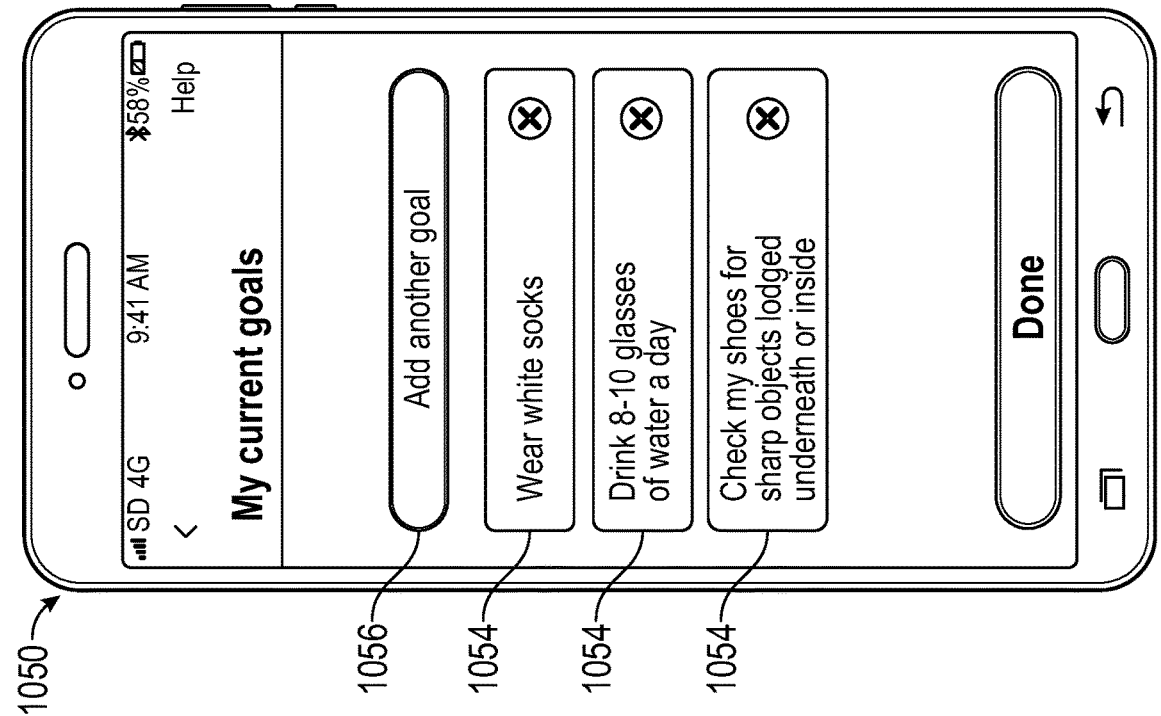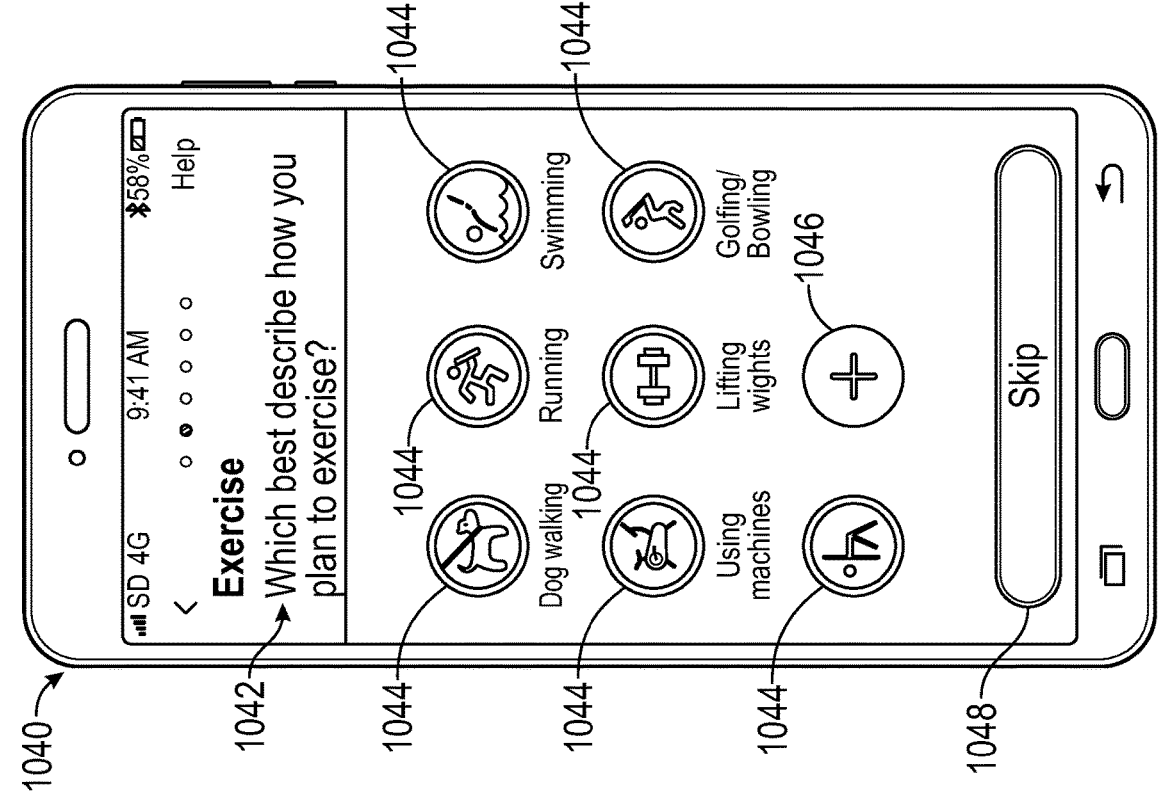

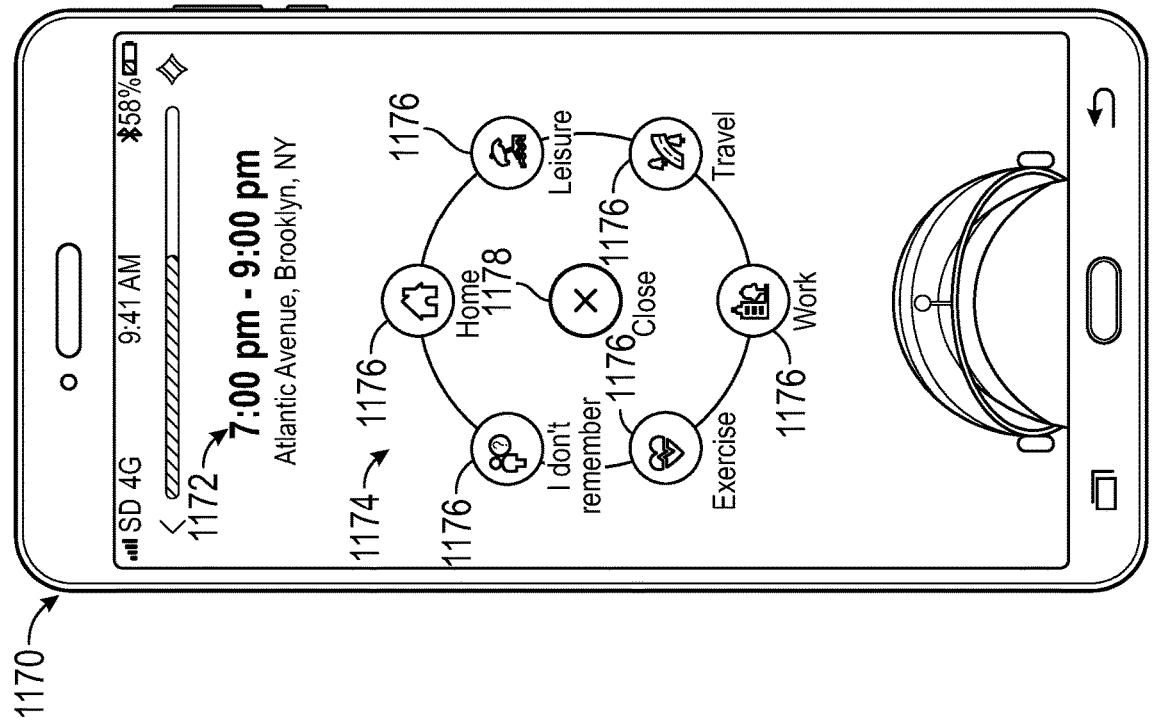
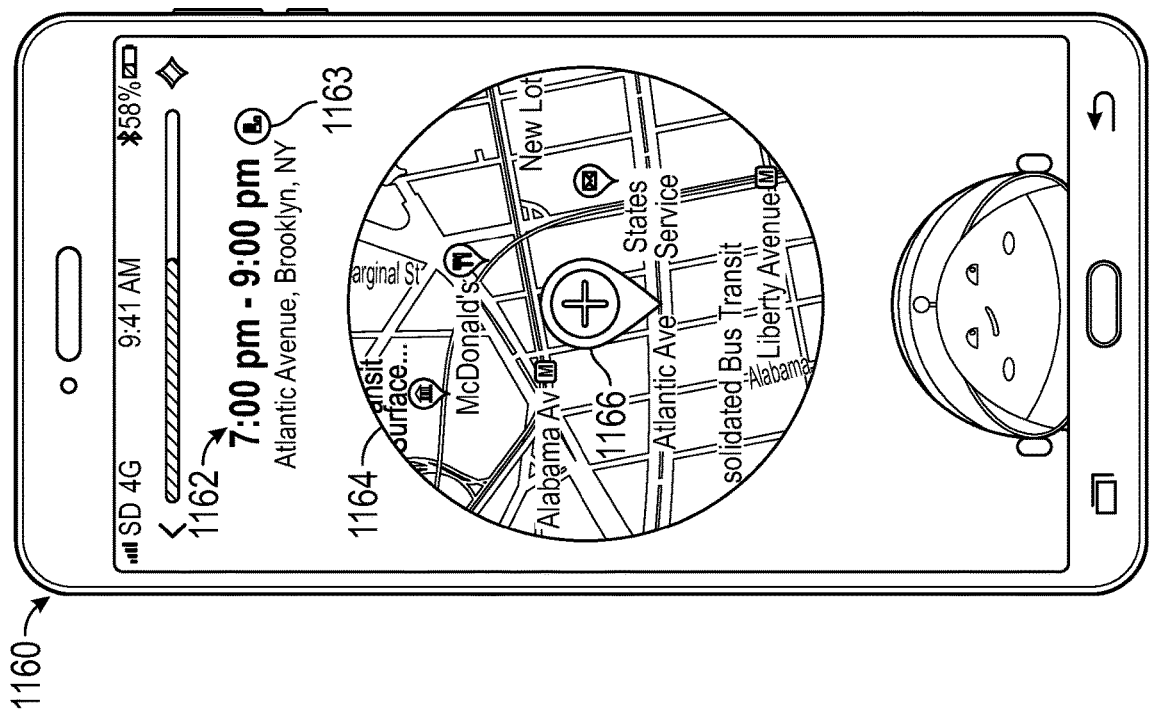

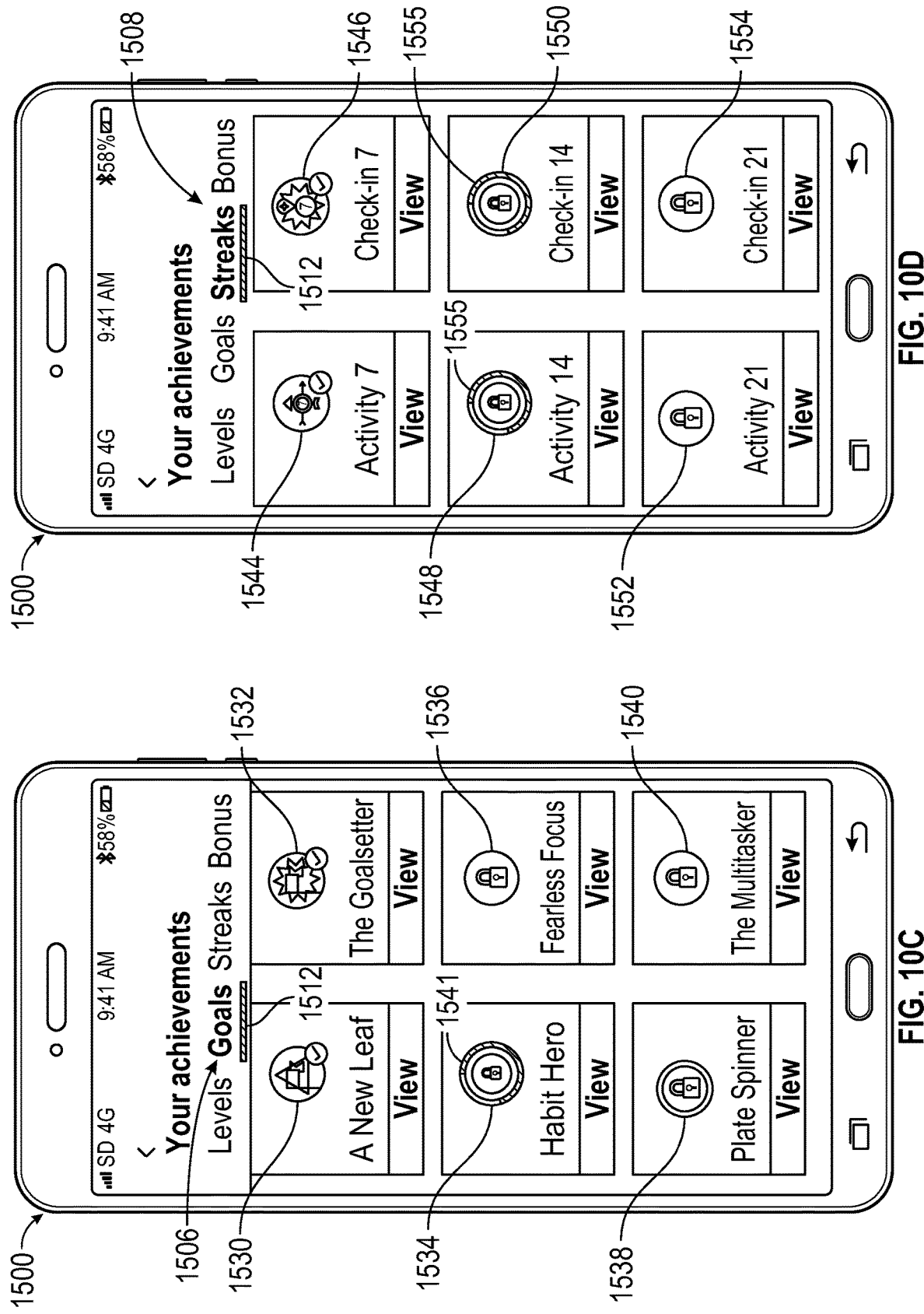

FIG. 12C

COMMUNICATION AND USER INTERFACE CONTROL IN USER ACTIVITY MONITORING SYSTEMS

CROSS-REFERENCE TO RELATED APPLICATIONS

This application is a U.S. national stage application of International Patent Application No. PCT/EP2020/060687, filed Apr. 16, 2020, which claims priority to U.K. Provisional Application Nos. 1906090.4, 1906092.0, 1906095.3, and 1906097.9 filed on May 1, 2019; the disclosures of which are hereby incorporated by reference in their entirety.

TECHNICAL FIELD

Embodiments of the present disclosure relate to apparatuses, systems, and methods for managing communication between user activity monitoring devices and other devices.

BACKGROUND

Pressure ulcers, which may also be known as pressure sores, bedsores, or decubitus ulcers, are injuries to skin and underlying tissue resulting from prolonged pressure on the skin, soft tissue, muscle, or bone above capillary filling pressure (approximately 32 mmHg).

One type of pressure ulcer that develops on a foot is known as a diabetic foot ulcer (DFU), which tends to occur with a higher frequency and intensity in the diabetic population. Management and treatment of diabetic foot ulcers requires offloading the diabetic foot ulcers by using cushioned footwear, such as a support boot, cast, shoe, or the like. While offloading can be effective, it has been found that non-compliance with or non-use of the offloading devices can play a large role in the delayed healing of the diabetic foot ulcers.

Prior art approaches and systems provide little or no information regarding an individual's lifestyle and compliance with the offloading devices. Gaining insight into the individual's lifestyle can be important for the prevention and healing of pressure ulcers. However, because of these limitations, the prevention and healing of pressure ulcers using prior art approaches and systems may be delayed or, worse yet, worsened leading to prolonged discomfort, hospitalization, or even surgery.

SUMMARY

In some aspects, a non-transitory computer readable medium is disclosed that has an application stored thereon that when executed by a processor of an electronic device causes the processor to perform a process. The process can include: receiving, by a communication interface, motion data from a motion sensor, the motion data being indicative of motion by a user while wearing the motion sensor; determining a time at which to request from the user contextual information for the motion data; disabling a functionality of the application prior to the time; enabling the functionality of the application subsequent to the time; and requesting from the user the contextual information at the time.

The non-transitory computer readable medium of the preceding paragraph can include one or more of the following features: The contextual information can be received from the user prior to the time and subsequent to the time. The contextual information can include an identification of a type of activity engaged in by the user while wearing the motion sensor. The disabling can include disabling the functionality by preventing user access to the functionality prior to the time. The functionality can include an ability of the user to provide inputs responding to a plurality of prompts. The contextual information can be requested from the user via a touchscreen. The process can include transmitting the motion data to a server via a computer network, the motion data being received from the motion sensor when the communication interface no more than 100 meters from the motion sensor. The computer network can be a cellular network. The motion sensor can include an accelerometer and a magnetometer, and the motion data can include sensor data from the accelerometer and the magnetometer.

In some aspects, a method is disclosed for gathering motion data from a motion sensor and controlling user engagement with an application that processes the motion data. The method can include, under control of a processor executing an application: receiving, by a communication interface, motion data from a motion sensor, the motion data being indicative of motion by a user while wearing the motion sensor; determining a time at which to request from the user contextual information for the motion data; disabling a functionality of the application prior to the time; enabling the functionality of the application subsequent to the time; and requesting from the user the contextual information at the time.

The method of the preceding paragraph can include one or more of the following features: The method can include receiving from the user the contextual information prior to the time and subsequent to the time. The contextual information can include an identification of a type of activity engaged in by the user while wearing the motion sensor. The disabling can include preventing user access to the functionality prior to the time. The functionality can include an ability of the user to provide inputs responding to a plurality of prompts. The contextual information can be requested and received from the user using a touchscreen. The method can include transmitting the motion data to a server via a computer network, the motion data being received from the motion sensor when the communication interface no more than 100 meters from the motion sensor. The computer network can be a cellular network. The motion sensor can include an accelerometer and a magnetometer, and the motion data can include sensor data from the accelerometer and the magnetometer.

In some aspects, an apparatus is disclosed for gathering motion data from a motion sensor and controlling user engagement with an application that processes the motion data. The apparatus can include: a communication interface configured to communicate with a motion sensor; and a processor configured to execute an application to: receive motion data from the motion sensor, the motion data being indicative of motion by a user while wearing the motion sensor, determine a time at which to request from the user contextual information for the motion data, disable a functionality of the application prior to the time, enable the functionality of the application subsequent to the time, and request from the user the contextual information at the time.

The apparatus of the preceding paragraph can include one or more of the following features: The apparatus can include a housing supporting the communication interface and the processor, a display configured to request from the user the contextual information, or a user input configured to receive the contextual information from the user. A system can include the apparatus and the motion sensor or a server, the processor being configured to transmit the motion data to the server via the communication interface.

In some aspects, a non-transitory computer readable medium is disclosed that has an application stored thereon that when executed by a processor of an electronic device causes the processor to perform a process. The process can include: receiving, by a communication interface, motion data from a motion sensor, the motion data being indicative of motion by a user while wearing the motion sensor; requesting and receiving from the user contextual information for the motion data; determining an engagement metric for the user from the contextual information, the engagement metric being indicative of an amount of engagement by the user with the application; and adjusting, responsive to the engagement metric, a graphical user interface of the application for presentation to the user.

The non-transitory computer readable medium of the preceding paragraph can include one or more of the following features: The contextual information can include an identification of an activity engaged in by the user while wearing the motion sensor or an indication by the user of how the user is feeling. The determining can include determining the engagement metric from a count of a number of days for which the user provided the contextual information. The adjusting can include adjusting the graphical user interface differently if the count satisfies a threshold than if the count does not satisfy the threshold. The determining can include determining the engagement metric from a number of consecutive days for which the user provided the contextual information. The adjusting can include adjusting the graphical user interface by presenting a user feedback selected from a set of first feedback options rather than a set of second feedback options, the set of first feedback options being different from the set of second feedback options. The adjusting can include adjusting the graphical user interface by changing a formatting of information included in the graphical user interface. The adjusting can include adjusting the graphical user interface by incorporating a first image rather than a second image in the graphical user interface, the first image being different from the second image. The contextual information can be requested and received from the user via a touchscreen. The process can include: according at least to a number of goals set by the user or a number of the goals completed by the user, assigning a badge from a plurality of badges to the user; and incorporating the badge in the graphical user interface. The process can include transmitting the motion data to a server via a computer network, the motion data being received from the motion sensor when the communication interface is no more than 100 meters from the motion sensor. The computer network can be a cellular network. The motion sensor can include an accelerometer and a magnetometer, and the motion data can include sensor data from the accelerometer and the magnetometer.

In some aspects, a method is disclosed for gathering motion data from a motion sensor and processing contextual information associated with the motion data. The method can include, under control of a processor executing an application: receiving, by a communication interface, motion data from a motion sensor, the motion data being indicative of motion by a user while wearing the motion sensor; requesting and receiving from the user contextual information for the motion data; determining an engagement metric for the user from the contextual information, the engagement metric being indicative of an amount of engagement by the user with the application; and adjusting, responsive to the engagement metric, a graphical user interface of the application, the graphical user interface generated by the processor for presentation to the user.

The method of the preceding paragraph can include one or more of the following features: The contextual information can include an identification of an activity engaged in by the user while wearing the motion sensor or an indication by the user of how the user is feeling. The determining can include determining the engagement metric from a count of a number of days for which the user provided the contextual information. The adjusting can include adjusting the graphical user interface by presenting a user feedback selected from a set of first feedback options rather than a set of second feedback options, the set of first feedback options being different from the set of second feedback options. The adjusting can include adjusting the graphical user interface by changing a formatting of information included in the graphical user interface or by incorporating a first image rather than a second image in the graphical user interface, the first image being different from the second image. The contextual information can be requested and received from the user using a touchscreen. The method can include transmitting the motion data to a server via a computer network, the motion data being received from the motion sensor when the communication interface is no more than 100 meters from the motion sensor. The motion sensor can include an accelerometer and a magnetometer, and the motion data can include sensor data from the accelerometer and the magnetometer.

In some aspects, an apparatus is disclosed for gathering motion data from a motion sensor and processing contextual information associated with the motion data. The apparatus can include: a communication interface configured to communicate with a motion sensor; and a processor configured to execute an application to: receive motion data from the motion sensor, the motion data being indicative of motion by a user while wearing the motion sensor, request and receive from the user contextual information for the motion data, determine an engagement metric for the user from the contextual information, the engagement metric being indicative of an amount of engagement by the user with the application, and adjust, responsive to the engagement metric, a graphical user interface of the application, the graphical user interface being generated by the processor for presentation to the user.

The apparatus of the preceding paragraph can include one or more of the following features: The apparatus can include a housing supporting the communication interface and the processor, a display configured to request from the user the contextual information and present the graphical user interface, or a user input configured to receive the contextual information from the user. A system can include the apparatus and the motion sensor or a server, the processor being configured to transmit the motion data to the server via the communication interface.

In some aspects, a non-transitory computer readable medium is disclosed that has an application stored thereon that when executed by a processor of an electronic device causes the processor to perform a process. The process can include: receiving, by a communication interface, motion data from a motion sensor, the motion data being indicative of motion by a user while wearing the motion sensor; transmitting, by the communication interface, the motion data to a server; receiving, by the communication interface, from the server a time that the motion data indicates a foot of the user experienced a loading force which risked adversely impacting an existing ulcer on the foot or risked causing a new ulcer on the foot; determining a geographic location of the motion sensor at the time that the foot experienced the loading force; displaying the time and the geographic location to the user on a display; requesting on the display that the user identify an activity engaged in by the user at the time and the geographic location; and transmitting the activity to the server for storage to a memory device in association with the time and the geographic location.

The non-transitory computer readable medium of the preceding paragraph can include one or more of the following features: The motion data can be received from the motion sensor when the communication interface no more than 100 meters from the motion sensor, and the motion data can be transmitted to the server via a computer network. The computer network can be a cellular network. The motion sensor can include an accelerometer and a magnetometer, and the motion data can include sensor data from the accelerometer and the magnetometer. The determining can include determining the geographic location from a physical location of the processor at the time. The determining can include determining the physical location using a global positioning system (GPS) receiver or a communication received via a computer network. The displaying can include displaying the time and the geographic location together on the display. The time can indicate when, based at least on the motion data, the foot experienced the loading force which risked adversely impacting the existing ulcer and the user is determined to have not been wearing an offloading device. The activity can include a type of transportation, a type of exercise, a type of leisure, a type of home activity, or a type of work. The process can include requesting that the user identify the activity from a plurality of different activity types previously indicated by the user to be types of activities commonly engaged in by the user.

In some aspects, a method is disclosed for gathering motion data from a motion sensor and processing event information associated with the motion data. The method can include: receiving, by a communication interface, motion data from a motion sensor, the motion data being indicative of motion by a user while wearing the motion sensor; transmitting, by the communication interface, the motion data to a server; receiving, by the communication interface, from the server a time that the motion data indicates a foot of the user experienced a loading force which risked adversely impacting an existing ulcer on the foot or risked causing a new ulcer on the foot; determining, by a processor, a geographic location of the motion sensor at the time that the foot experienced the loading force; displaying the time and the geographic location to the user on a display; requesting on the display that the user identify an activity engaged in by the user at the time and the geographic location; and transmitting the activity to the server for storage to a memory device in association with the time and the geographic location.

The method of the preceding paragraph can include one or more of the following features: The motion data can be received from the motion sensor when the communication interface no more than 100 meters from the motion sensor, and the motion data can be transmitted to the server via a computer network. The computer network can be a cellular network. The motion sensor can include an accelerometer and a magnetometer, and the motion data can include sensor data from the accelerometer and the magnetometer. The determining can include determining the geographic location from a physical location of the processor at the time. The determining can include determining the physical location using a global positioning system (GPS) receiver or a communication received via a computer network. The time can indicate when, based at least on the motion data, the foot experienced the loading force which risked adversely impacting the existing ulcer. The method can include receiving the activity from the user via a user input. The activity can include a type of transportation, a type of exercise, a type of leisure, a type of hobby, or a type of work. The requesting can include requesting that the user identify the activity from a plurality of different activity types previously indicated by the user to be types of activities commonly engaged in by the user.

In some aspects, an apparatus is disclosed for gathering motion data from a motion sensor and processing event information associated with the motion data. The apparatus can include: a communication interface configured to communicate with a motion sensor and a server; and a processor configured to: receive motion data from the motion sensor, the motion data being indicative of motion by a user while wearing the motion sensor, transmit the motion data to the server, receive from the server a time that the motion data indicates a foot of the user experienced a loading force which risked adversely impacting an existing ulcer on the foot or risked causing a new ulcer on the foot, determine a geographic location of the motion sensor at the time that the foot experienced the loading force, output for presentation to the user the time and the geographic location, request that the user identify an activity engaged in by the user at the time and the geographic location, and transmit the activity to the server for storage to a memory device in association with the time and the geographic location.

The apparatus of the preceding paragraph can include one or more of the following features: The apparatus can include a housing supporting the communication interface and the processor, a display configured to present the time and the geographic location, or a user input configured to receive the activity from the user. A system can include the apparatus and the motion sensor or the server.

In some aspects, a non-transitory computer readable medium is disclosed that has an application stored thereon that when executed by a processor of an electronic device causes the processor to perform a process. The process can include: requesting from the server, via a communication interface, behavior data indicative of (i) a duration of time that a foot of a user was active and (ii) a duration of time that the user used an offloading device, the behavior data being determined from motion data gathered by a first motion sensor worn by the user and from offloading device usage data gathered by a second motion sensor supported by the offloading device; generating a first user interface comprising a first value responsive to the duration of time that the foot was active and a second value responsive to the duration of time that the user used the offloading device; and displaying the first user interface on a display.

The non-transitory computer readable medium of the preceding paragraph can include one or more of the following features: The process can include generating a second user interface which permits a selection of individual users of a plurality of users for which the motion data and the offloading device usage data has been collected, the plurality of users comprising the user; and the process can include transitioning from displaying the second user interface on the display to displaying the first user interface responsive to a user input. The process can include, responsive to a user input, displaying the first user interface on the display in place of the second user interface. The first user interface can include a third value indicative of a difference between the duration of time that the foot was active and the duration of time that the user used the offloading device. The first user interface can identify the third value as corresponding to a period at which the foot was at risk of injury. The first user interface can include a target period of time for which the foot should be active, and the process can include setting the target period of time responsive to a user input. The process can include receiving from the server a plurality of activity types identified as being types of activities engaged in by the user during which the foot was at risk of injury, and the first user interface can identify the plurality of activity types. The first user interface can identify a plurality of durations corresponding to the plurality of activity types, the plurality of durations indicating lengths of time during which the foot was at risk of injury during engagement in the types of activities. The first user interface can identify a plurality of offloading device utilizations corresponding to the plurality of activity types, the plurality of offloading device utilizations indicating portions of time during which the foot was at risk of injury during engagement in the types of activities when the offloading device was unused by the user. Upon selection of one of the activity types by the user, the first user interface can present at least one of: (i) a number of events engaged in by the user during the selected one of the activity types and during which the foot was at risk of injury, (ii) an average time during which the foot was at risk of injury during engagement in the selected one of the activity types by the user, (iii) a number of impacts to the foot during engagement in the selected one of the activity types by the user, or (iv) a portion of time during which the foot was at risk of injury during engagement in the types of activities when the offloading device was unused by the user. The process can include generating a second user interface which identifies the duration of time that the foot was active during individual periods of a plurality of periods of time and the duration of time that the user used the offloading device during the individual periods of the plurality of periods of time; and the process can include displaying the second user interface on the display. The computer network can be a cellular network. The motion data can include sensor data from an accelerometer and a magnetometer of the first motion sensor.

In some aspects, a method is disclosed for processing motion data gathered by a motion sensor. The method can include, under control of a processor executing an application: requesting from the server, via a communication interface, behavior data indicative of (i) a duration of time that a foot of a user was active and (ii) a duration of time that the user used an offloading device, the behavior data being determined from motion data gathered by a first motion sensor worn by the user and from offloading device usage data gathered by a second motion sensor positioned on the offloading device; generating, by a processor, a first user interface comprising a first value responsive to the duration of time that the foot was active and a second value responsive to the duration of time that the user used the offloading device; and displaying the first user interface on a display.

The method of the preceding paragraph can include one or more of the following features: The method can include generating, by the processor, a second user interface which permits a selection of individual users of a plurality of users for which the motion data and the offloading device usage data has been collected, the plurality of users comprising the user; and the method can include transitioning from displaying the second user interface on the display to displaying the first user interface responsive to a user input. The first user interface can include a third value responsive to a comparison of the duration of time that the foot was active and the duration of time that the user used the offloading device, or the first user interface can identify the third value as corresponding to a period at which the foot was at risk of injury. The method can include receiving, via the communication interface, from the server a plurality of activity types identified as being types of activities engaged in by the user during which the foot was at risk of injury, and the first user interface can identify the plurality of activity types. The first user interface can identify a plurality of durations corresponding to the plurality of activity types, the plurality of durations indicating lengths of time during which the foot was at risk of injury during engagement in the types of activities. The first user interface can identify a plurality of offloading device utilizations corresponding to the plurality of activity types, the plurality of offloading device utilizations indicating portions of time during which the foot was at risk of injury during engagement in the types of activities when the offloading device was unused by the user. Upon selection of one of the activity types by the user, the first user interface can present at least one of: (i) a number of events engaged in by the user during the selected one of the activity types and during which the foot was at risk of injury, (ii) an average time during which the foot was at risk of injury during engagement in the selected one of the activity types by the user, (iii) a number of impacts to the foot during engagement in the selected one of the activity types by the user, or (iv) a portion of time during which the foot was at risk of injury during engagement in the types of activities when the offloading device was unused by the user. The method can include generating a second user interface which identifies the duration of time that the foot was active during individual periods of a plurality of periods of time and the duration of time that the user used the offloading device during the individual periods of the plurality of periods of time; and the method can include displaying the second user interface on the display.

In some aspects, an apparatus is disclosed for processing motion data gathered by a motion sensor. The apparatus can include: a communication interface configured to communicate with a server via a computer network; and a processor configured to execute an application to: request from the server behavior data indicative of (i) a duration of time that a foot of a user was active and (ii) a duration of time that the user used an offloading device, the behavior data being determined from motion data gathered by a first motion sensor worn by the user and from offloading device usage data gathered by a second motion sensor supported by the offloading device, generate for presentation a first user interface comprising a first value responsive to the duration of time that the foot was active and a second value responsive to the duration of time that the user used the offloading device, and output the first user interface.

The apparatus of the preceding paragraph can include one or more of the following features: The apparatus can include a housing supporting the communication interface and the processor, a display configured to present the first user interface, or a user input configured to receive user inputs from the user. A system can include the apparatus and the first motion sensor, the second motion sensor, or the server.

BRIEF DESCRIPTION OF THE DRAWINGS

Embodiments of the present disclosure will now be described hereinafter, by way of example only, with reference to the accompanying drawings in which:

FIG. 7E illustrates an example exercise type interface presentable in the computing environment of FIG. 3;

FIG. 7F illustrates an example user goal interface presentable in the computing environment of FIG. 3;

FIG. 8I illustrates an example geographic location interface presentable in the computing environment of FIG. 3;

FIG. 8J illustrates an example activity input interface presentable in the computing environment of FIG. 3;

FIGS. 10A, 10B, 10C, 10D, and 10E illustrate example achievement summary interfaces presentable in the computing environment of FIG. 3;

FIG. 12C illustrates an example individual user interface presentable in the computing environment of FIG. 3;

DETAILED DESCRIPTION

Introduction to User Activity Monitoring

Figure 1:
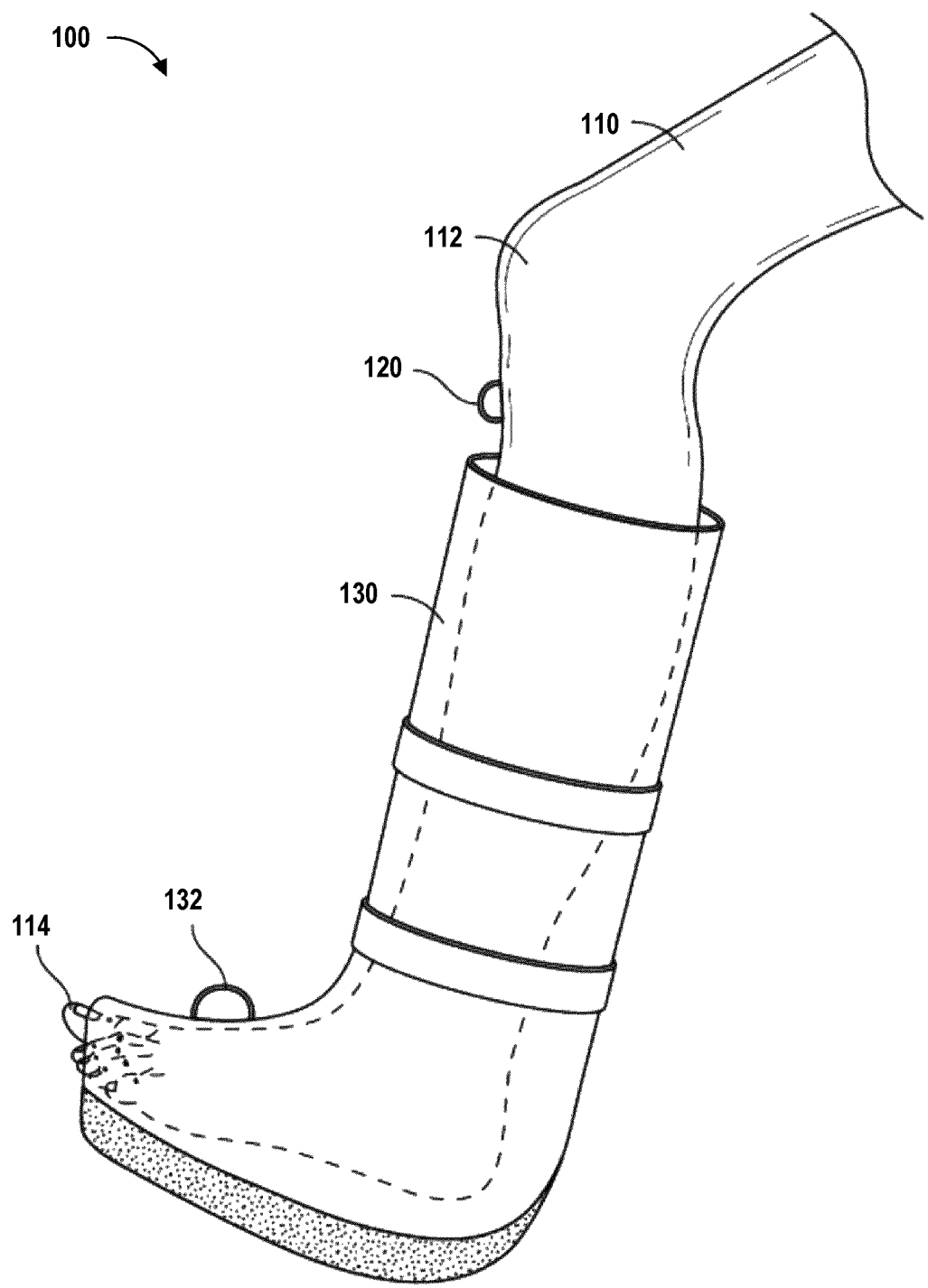
FIG. 1 illustrates an example user activity monitoring system that includes an activity monitoring device and an offloading monitoring device.

Activities of a user may be desirably monitored by an activity monitoring device for a variety of reasons, including wound prevention and monitoring. In one example, the activities of a user can be monitored when the user may be prone to or already have a wound, such as a pressure ulcer. Information gathered by the activity monitoring device about the activities of the user can be helpful for assisting with prevention or treatment of the pressure ulcer. In addition, information gathered by the activity monitoring device about the activities can be useful for checking compliance with a treatment regimen.

Some aspects disclosed herein relate to wound monitoring or therapy for a human or animal body. Therefore, any reference to a wound herein can refer to a wound on a human or animal body, and any reference to a body herein can refer to a human or animal body. The disclosed technology may relate to preventing or minimizing damage to physiological tissue or living tissue, or to the treatment of damaged tissue (for example, a wound as described herein).

As used herein the expression "wound" may include an injury to living tissue that may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may have the potential to be cut (for example, for joint replacement/surgical alteration/reconstruction).

Some aspects relate to methods of monitoring or treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure or traditional advanced wound care, which is not aided by the using of applied negative pressure (may also be referred to as non-negative pressure therapy).

Although the present disclosure may refer to pressure ulcers, foot ulcers, or the like, the systems and methods disclosed herein can be used for preventing, monitoring, or treating any type of skin injury or wound, such as venous leg ulcer.

User Activity Monitoring System

FIG. 1 illustrates a user activity monitoring system 100 including an activity monitoring device 120 attached to a body part 110. The activity monitoring device 120 can be attached to the body part 110 using a strap, adhesive, or other coupling mechanism and may be worn on or supported by the body.

The body part 110 can be a leg of a user that includes a knee 112 and a foot 114. As illustrated, the activity monitoring device 120 can be supported by the body part 110 at a position between the knee 112 and the foot 114, such as proximate to the knee 112. In other aspects, the activity monitoring device 120 can be supported by another part of the body part 110, such as above the knee 112 or elsewhere. The activity monitoring device 120 can monitor and record activities (for instance, walking, jumping, sitting, laying down, running, squatting, or standing) of the body part 110, such as from a position, movement, or orientation of the activity monitoring device 120 or one or more other sensors of the activity monitoring device 120. The activity monitoring device 120 can, for example, be used for loading monitoring of loading of the foot 114. In certain implementations, multiple body parts can be monitored by the activity monitoring device 120, and different sensors can be used for monitoring different body parts.

The body part 110 is shown wearing and being partly covered by an offloading device 130. The offloading device 130 can support the body part 110 and reduce a pressure on the foot 114 when the user may be standing or engaging in other activities. An offloading monitoring device 132 can be attached to the offloading device 130. The offloading monitoring device 132 can be the same as or similar to the activity monitoring device 120 and monitor and record activities of the offloading device 130. The offloading monitoring device 132 can be supported by the offloading device 130 using a strap, adhesive, or other coupling mechanism. The offloading monitoring device 132 can be attached to an inner surface or outer surface of the offloading device 130. Although not shown in FIG. 1, the offloading monitoring device 132 may be attached to an offloading device that is not worn by the user (for example, a cane or a walker). Moreover, the activity monitoring device 120 can be worn regardless of whether the offloading device 130 may be worn.

The user activity monitoring system 100 can additionally or alternatively include one or more of the activity monitoring device 120 or the offloading monitoring device 132 at other positions, such as at a position supported by the offloading device 130, another part of the body part 110, another device not worn such as a cane or a walker, or elsewhere. The one or more additional or alternative of the activity monitoring device 120 or the offloading monitoring device 132 can be the same as or similar to the activity monitoring device 120 may monitor and record activities of the offloading device 130, the another part of the body part 110, or the body.

Figure 2:
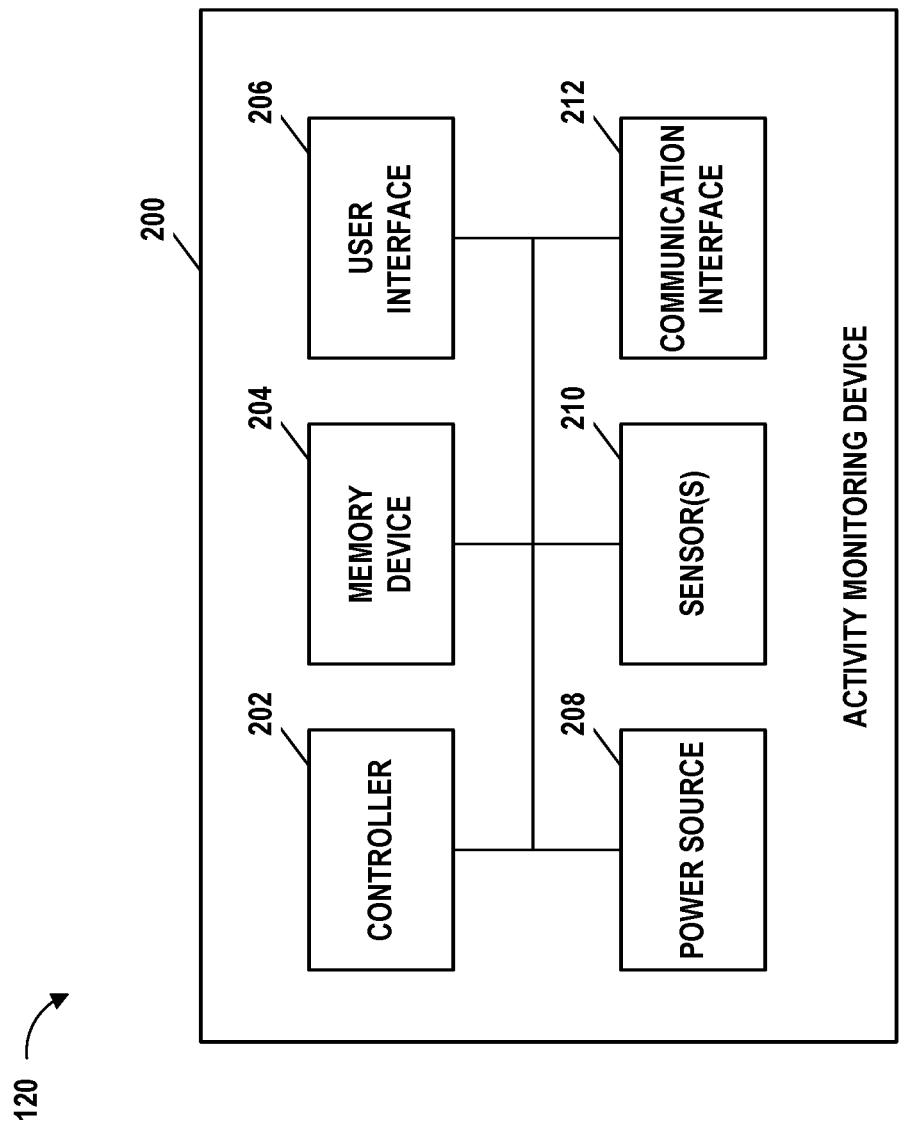
FIG. 2 illustrates example components of the activity monitoring device of FIG. 1.

FIG. 2 illustrates example components of the activity monitoring device 120. The activity monitoring device 120 can include a housing 200, a controller 202, a memory device 204, a user interface 206, a power source 208, one or more sensors 210, and a communication interface 212 that are configured to communicate, such as electrically, with one another. The power source 208 can provide power to one or more components of the activity monitoring device 120.

One or more of the components of the activity monitoring device 120 can be contained in or supported by the housing 200. The housing 200 can be composed of a top portion and a bottom portion that are sealed together, and the top portion or the bottom portion can be hard or soft. The housing 200 can be flexible and have a mechanical structure and design features that provide for a shouldered keyway alignment of components within the housing 200. The housing 200 can support a circuit board on its inside and on which one or more components of the activity monitoring device 120 may be positioned.

The housing 200 can be made by stereolithography (SLA) or polyjet from photopolymer 3D printing material or by 3D printing from an engineering resin with a shorehardness of 80A. The housing 200 can include an elastomer, a thermoplastic elastomer, or be constructed by injection molding. The molded parts of the housing 200 can be made from liquid silicone rubber in white. An adhesive (for example, one for attaching plastics and elastomeric materials) can be used to glue the top and bottom portions of the housing 200 together, and a wide range of other adhesives (for example, cyanoacrylates, silicones, epoxies, hydrogels, hydrocolloids, sealant systems) or other techniques (for example use of double-sided adhesive tapes, ultrasonic welding, staking) can be used.

The controller 202 can control operations of one or more other components (for instance, the memory device 204, the user interface 206, the power source 208, the one or more sensors 210, or the communication interface 212) of the activity monitoring device 120 according at least to instructions stored in the memory device 204. The controller 202 can, for instance, control monitoring of loading of the body part 110 with a weight of the body or positioning of the body part 110 and record data indicative of loading of the body part 110 or positioning of the body part 110 to the memory device 204.

The user interface 206 can include one or more output elements, such as visual feedback devices (for example, light emitting diodes), haptic feedback devices, or audio devices (for example, speakers), that provide user outputs to a user. The one or more output elements can convey status information to the user like whether the activity monitoring device 120 is successfully functioning or has successfully configured communication with another device. The user interface 206 can include one or more input elements, such as buttons, switches, dials, touch pads, microphones, or touch screens, for receiving user inputs for configuring the activity monitoring device 120. In some aspects, the user interface 206 may have no more than one user input element, such as a button, for receiving user inputs to activate and deactivate the activity monitoring device 120 or performing one or more other functions.

The one or more sensors 210 can be used to detect and monitor a motion of the activity monitoring device 120 or other characteristics of or around the activity monitoring device 120. The one or more sensors 210 can be used to detect and monitor activities of the user of the activity monitoring device 120 that include, for instance, a loading or positioning of the body part 110. The one or more sensors 210 can include one or more accelerometers, gyroscopes, magnetometers, impedance sensors, thermistors, pressure sensors, or optical sensors, among other types of sensors. The one or more sensors 210 can be positioned proximate to the body part 110 or may be remote from the body part 110 yet usable to monitor characteristics of the body part 110.

The communication interface 212 can be used to communicate with other devices, such as wirelessly via radio waves and according to a Bluetooth™ protocol like Bluetooth™ Low Energy or another protocol. The communication interface 212 can, for example, communicate and pair with other devices and transmit device usage or sensor data like alarms, monitored loading or positioning, or changes to a monitoring or therapy program performed by the activity monitoring device 120 to the other devices. The communication interface 212 can be used to receive data, including commands, from the other devices. The communication interface 212 can permit communication with (for example, transfer of data to or processing commands from) another device once a communication channel has been configured for communication with the another device (for example, by device pairing). The communication interface 212 may, in some aspects, be unable to communicate farther than 10 meters, 30 meters, or 100 meters away from the communication interface 212.

Figure 3:
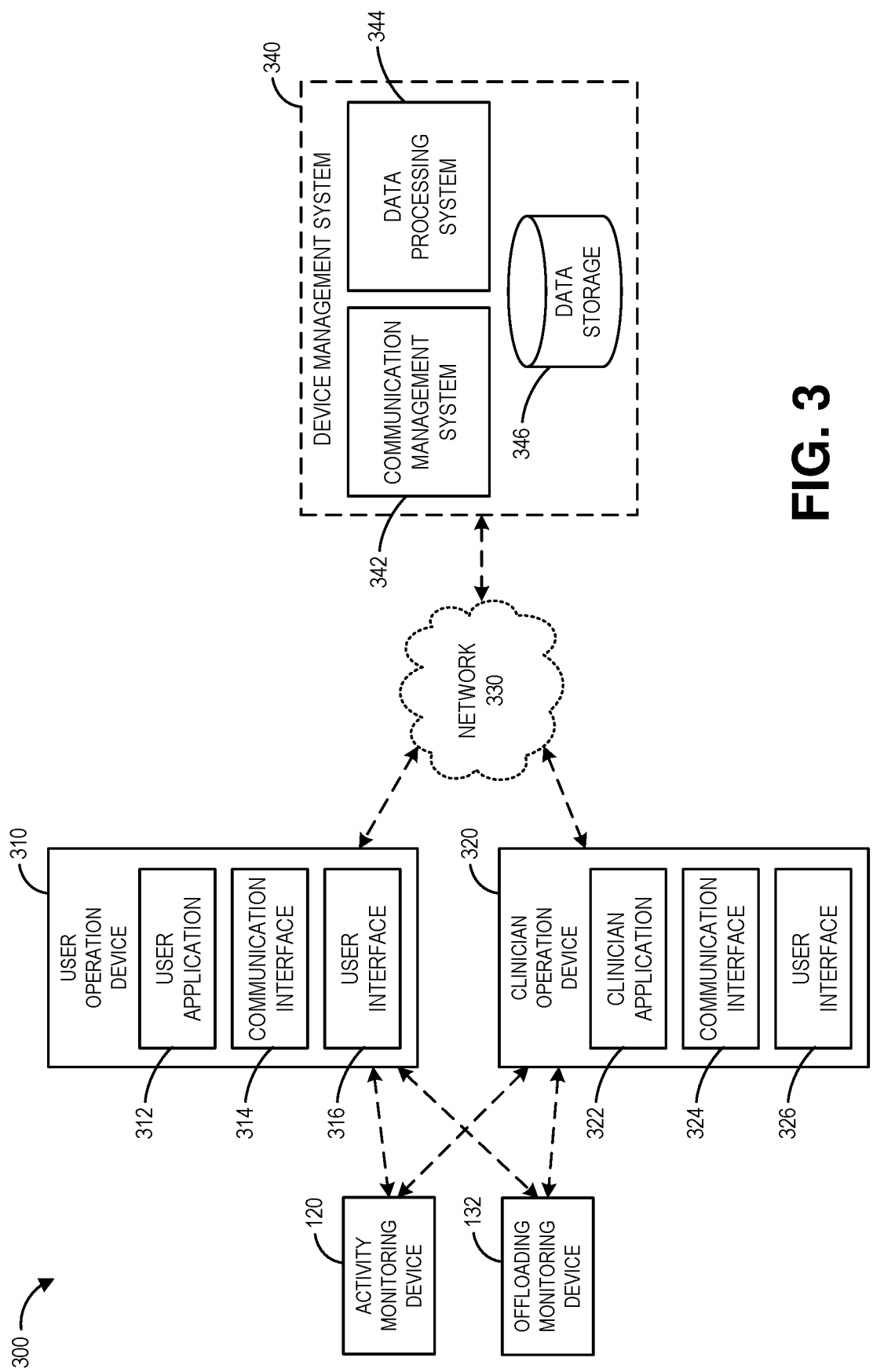
FIG. 3 illustrates an example computing environment that includes the activity monitoring device and the offloading monitoring device of FIG. 1.

FIG. 3 illustrates a computing environment 300 that includes the activity monitoring device 120 and the offloading monitoring device 132. The computing environment 300 shows the activity monitoring device 120 and the offloading monitoring device 132 in communication with a user operation device 310 and a clinician operation device 320, as well as the user operation device 310 and the clinician operation device 320 in communication with a device management system 340 via a network 330.

The user operation device 310 can be operated by a user, such as a wearer, of the activity monitoring device 120 and the offloading monitoring device 132. The user operation device 310 can permit the user to use the user operation device 310 to collect, process, review, or transmit the data gathered by the activity monitoring device 120 and the offloading monitoring device 132. On the other hand, the clinician operation device 320 can be operated by a clinician for the user, such as an individual who supervises, assists, or cares for the user that uses the activity monitoring device 120 and the offloading monitoring device 132. The clinician operation device 320 can permit the clinician to use the clinician operation device 320 to collect, process, review, or transmit the data gathered by the activity monitoring device 120 and the offloading monitoring device 132.

The user operation device 310 and the clinician operating device 320 may each be a computing device such as a smart phone, a tablet computer, or a desktop computer. In some aspects, the user operation device 310 and the clinician operating device 320 can receive, send, present, and access data gathered by the activity monitoring device 120 and the offloading monitoring device 132 or data determined therefrom, but may not process the data gathered by the activity monitoring device 120 and the offloading monitoring device 132 to analyze the characteristics of the data (such as to identify from the data when the user used an offloading device or calculate a duration of activity engaged in by the user.

The user operation device 310 can include a user application 312, a communication interface 314 (which can, for instance, include any one or more of the features of the communication interface 212), and a user interface 316 (which can, for instance, include any one or more of the features of the user interface 206). The user application 312 can be program that is executed by processor of the user operation device 310. The user application 312 can enable the user operation device 310 to communicate via the communication interface 314 with the activity monitoring device 120, the offloading monitoring device 132, and the device management system 340. The user application 312 may receive, collect, process, review, or transmit (i) data gathered or determined by the activity monitoring device 120 and the offloading monitoring device 132, such as motion data, alarms, monitored loading or positioning, or changes to a monitoring or therapy program, (ii) data collected or determined by the user application 312, such as user observations, goal information, or identifications of activities engaged in by a user, or (iii) data collected or determined by the device management system 340, such as a duration of time that the user was active, a portion of time that the user used an offloading device, or an amount of time at which an injury of the user may be at risk due to activity by the user or nonuse of the offloading device. The user application 312 can moreover present to the user one or more graphical user interfaces, such as one or more of the graphical user interfaces described herein, with the user interface 316, such as on a display or a touchscreen of the user interface 316.

The user application 312 can be used to gather information from the user to assist with understanding what type of activity was engaged in by the user when the foot of the user may have experienced a force which risked adversely impacting an existing ulcer on the foot or risked causing a new ulcer on the foot. The user application 312 can receive from the device management system 340 a time that the motion data from the activity monitoring device 120 indicates a foot of the user experienced a force which risked adversely impacting an existing ulcer on the foot or risked causing a new ulcer on the foot, and the user application 312 can determine a geographic location of the user operation device 310 (such as from a global positioning system (GPS) receiver of the user operation device 310 or a communication received by the user operation device 310 via the network 330) that may be indicative of a geographic location of the activity monitoring device 120 at the time. The user application 312 may output the time and the geographic location of the user operation device 310 along with a request that the user identify the type of activity engaged in by the user at the time and the geographic location. The type of activity can, for example, include a type of transportation, a type of exercise, a type of leisure, a type of hobby, or a type of work. The request may list a set of types of activities commonly engaged in by the user to assist in selecting the type of activity engaged in by the user.

The user application 312 can include a functionality lock out that causes certain functionality of the user application 312 to be disabled (such as by preventing access to the functionality) prior to a check-in time for the user. The check-in time can be a time provided by the user when the user anticipates that the user will settle down and likely not engage in additional activity which may adversely impact an existing or new foot ulcer. The functionality lock out can assist with controlling a timing of engagement by the user with the user application 312, such as until after the user may have settled down for a day, to help ensure a complete collection of requested information from the user for the day. The functionality can, for instance, include an ability of the user to respond to prompts, such as regarding the user's thoughts or observations on the day or the user's feelings. Although the functionality lock out may lock out some functionality, other functionality of the user application 312 can be available prior to the check-in time for access or completion by the user prior to the check-in time.

The user application 312 can include aspects and interfaces that seek to increase the amount or frequency of user engagement with the user application 312. The user application 312 may request contextual information (such as an identification of an activity engaged in by the user while wearing the activity monitoring device 120 or an indication by the user of how the user is feeling) to assist with tracking or understanding why the foot of the user may have experienced a force which risked adversely impacting an existing ulcer on the foot or risked causing a new ulcer on the foot. From the contextual information, such as a timing or frequency of receipt of the contextual information, the user application 312 can determine an engagement metric for the user that may be indicative of an amount of engagement by the user with the user application 312. The engagement metric can, in turn, be used by the user application 312 to adjust a graphical interface generated by the user application 312 and presented to the user by the user interface 316.

The clinician operation device 320 can include a clinician application 322, a communication interface 324 (which can, for instance, include any one or more of the features of the communication interface 212), and a user interface 326 (which can, for instance, include any one or more of the features of the user interface 206). The clinician application 322 can be program that is executed by processor of the clinician operation device 320. The clinician application 322 can enable the clinician operation device 320 to communicate via the communication interface 324 with the activity monitoring device 120, the offloading monitoring device 132, and the device management system 340. The clinician application 322 may receive, collect, process, review, or transmit (i) data gathered or determined by the activity monitoring device 120 and the offloading monitoring device 132, such as motion data, alarms, monitored loading or positioning, or changes to a monitoring or therapy program, (ii) data collected or determined by the user application 312, such as user observations, goal information, or identifications of activities engaged in by a user, or (iii) data collected or determined by the device management system 340, such as a duration of time that the user was active, a portion of time that the user used an offloading device, or an amount of time at which an injury of the user may be at risk due to activity by the user or nonuse of the offloading device. The clinician application 322 can present to the clinician one or more graphical user interfaces, such as one or more of the graphical user interfaces described herein, with the user interface 326, such as on a display or a touchscreen of the user interface 326.

In some aspects, the clinician operation device 320 may not directly communicate with the activity monitoring device 120 or the offloading monitoring device 132. Instead, the clinician operation device 320 may receive any data collected by or associated with the activity monitoring device 120 and offloading monitoring device 132 from the device management system 340 through the user operation device 310. Such a design may desirably limit the number of devices (other than the user operation device 310) that may receive data directly from the activity monitoring device 120 and the offloading monitoring device 132 and thereby enhance the security of and limit access to the data.

The device management system 340 can be a computing device, such as a server, and include a communication management system 342, a data processing system 344, and a data storage 346 that may be in communication with one another. The device management system 340 may, for instance, be constructed partly or entirely of a server infrastructure or a cloud architecture, such as using a cloud infrastructure provided by Amazon Web Services™ (AWS), Microsoft™ Azure™, Google Cloud Platform™ (GCP), or Oracle™ Cloud Infrastructure (OCI). The server infrastructure and the cloud infrastructure can be compliant with the requirements of HIPAA (Health Insurance Portability and Accountability Act of 1996) and provide data privacy and security protections in view of the potentially sensitive nature of the data collected, processed, or determined by the device management system 340.

The communication management system 342 may permit the device management system 340 to communicate over the network 330 with the user operation device 310 and the clinician operation device 320. The communication management system 342 can include an application programming interface (API), such as a cloud API, to facilitate its communications.

The data processing system 344 can collect, process, present, store (such as in the data storage 346), or transmit the data gathered or determined by the activity monitoring device 120 and the offloading monitoring device 132 (such as motion data, alarms, monitored loading or positioning, or changes to a monitoring or therapy program) and the data collected or determined by the user application 312 (such as user observations, goal information, or identifications of activities engaged in by a user). For example, the data processing system 344 can process the data gathered by the activity monitoring device 120 and the offloading monitoring device 132 to determine an activity likely engaged in by the user (such as sitting/standing, driving a car, walking, or laying down with foot elevated) during various periods of time over which the data was gathered, as well as whether the user likely wore an offloading device (such as from a comparison of the motion data from the activity monitoring device 120 and the offloading monitoring device 132) during various periods of time over which the data was gathered. The determined likely activity or use of the offloading device may be shared by the device management system 340 with the user operation device 310 or the clinician operation device 320. As another example, the data processing system 344 can process the data gathered by the activity monitoring device 120 and the offloading monitoring device 132 to identify events of interest, such as events that may indicate excessive pressure being placed on the body part 110, and may share the events of interest with the user operation device 310 or the clinician operation device 320.

The network 330 can be a computer network, such as a cellular communications network. Although the network 330 is shown as one connected network, the network 330 can be subdivided into one or more separate networks which may not directly communicate with one another. For example, the device management system 340 can communicate with the user operation device 310 via a separate and different network from the network that the device management system 340 uses to communication with the clinician operation device 320.

Although certain data processing in the computing environment 300 may be described as being performed by the activity monitoring device 120, the offloading monitoring device 132, the user operation device 310, the clinician operation device 320, or the data processing system 344, the certain data processing can be shifted to a different device or system in the computing environment 300. For example, the user operation device 310 may be described as not processing the motion data provided by the activity monitoring device 120 and the offloading monitoring device 132 and can instead rely on the data processing system 344 to analyze the motion data; however, the user operation device 310 can additionally or alternatively analyze the motion data using similar or different approaches or algorithms to the data processing system 344.

Figure 4:
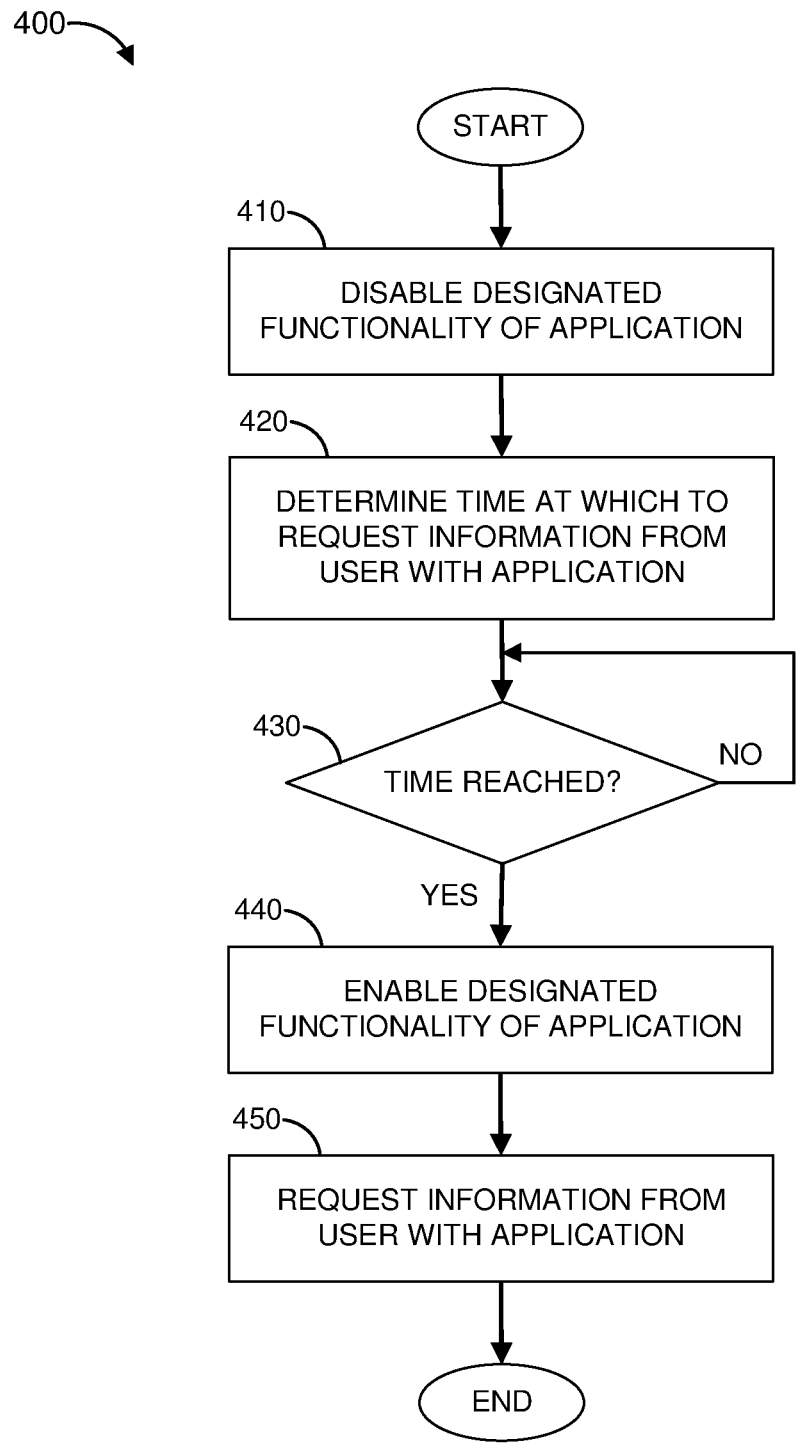
FIG. 4 illustrates an example functionality lockout process implementable in the computing environment of FIG. 3.

FIG. 4 illustrates a functionality lockout process 400 for disabling and enabling a functionality of an application, such as the user application 312 of the user operation device 310. For convenience, the functionality lockout process 400 is described in the context of the computing environment 300, but may instead be implemented in other components or systems described herein, or by other computing systems not shown. The functionality lockout process 400 can advantageously, in certain implementations, restrict the functionality of the user application 312 until a set to time try to encourage specific user engagement and collection of all desired or requested data from the user.

At block 410, the functionality lockout process 400 can disable a designated functionality of the application. The designated functionality may be a first subset of the functionality of the application, and a second subset of the application may not be disabled by the functionality lockout process 400. The functionality to be disabled can be designated by a programming in the application or responsive to changes in a flag in the memory device where the flag may be controlled by the application. For example, the designated functionality can include an ability of the user of the user operation device 310 to (i) be presented, by the user application 312, with prompts to which the user is requested to reply or (ii) provide inputs to the user application 312 by responding to the prompts. The prompts, for instance, may request that the user indicate how the user is feeling or the condition of the user's ulcer. Other examples of the designated functionality that may be disabled can include a functionality for accessing certain information within or through the user application 312 or a functionality associated with how the user responds to inputs to the user application 312 (such as by dismissing certain requests or providing one or more alternative prompts in place of the prompts).

At block 420, the functionality lockout process 400 can determine a time at which to request information from the user with the application. For example, the user application 312 may request via the user interface 316 that the user provide a check-in time at which the user is requested to provide information. The check-in time can be a time each day (or some other repeated time basis, such as hourly, every N hours, every N days, or weekly where N may be an integer) and may be in the afternoon or evening in some implementations. The check-in time can be a time provided or selected by the user when the user anticipates that the user will settle down and likely not engage in additional activity which may adversely impact an existing or new ulcer. The check-in time may be indicated to the user or understood by the user to be the time for requesting of certain information like contextual information for motion data gathered by the activity monitoring device 120, such as by identifying a type of activity associated with an event risked adversely impacting an existing ulcer on a foot the user or risked causing a new ulcer on the foot. The event can be an application of force to the foot when the user was determined to have not been wearing an offloading device. Additionally or alternatively, the user application 312 can request that the user interact with the user application 312 in a desired manner at the check-in time.

At block 430, the functionality lockout process 400 can remain on hold until the time at which to request information from the user has been reached (or at a time after such time). The user application 312 can continue to provide enabled functionalities during the on hold time, such as even to provide the information that is to be requested at the check-in time. One example of such an enabled functionality can be the ability to provide the contextual information for motion data gathered by the activity monitoring device 120. Once the time has been reached, the functionality lockout process 400 can transition to block 440.

At block 440, the functionality lockout process 400 can enable the designated functionality of the application that may have been disabled at block 410. The designated functionality can be enabled by a programming in the application due to expiration of a timer or responsive to the flag in the memory device where the flag may be controlled by the application according to a system time provided by the user operation device 310. For example, the user application 312 can unlock the ability of the user of the user operation device 310 to (i) be presented, by the user application 312, with prompts to which the user is requested to reply or (ii) provide inputs to the user application 312 by responding to the prompts. The user application 312 moreover may present the prompts responsive to enabling the designated functionality. In another example, the user application 312 can unlock the user's access to certain information within or through the user application 312 or adjust how the user application 312 responds to inputs to the user application 312.

At block 450, the functionality lockout process 400 can request the information from the user with the application. The user application 312, for example, can request via the user interface 316 that the user provide the requested information. Additionally or alternatively, the user application 312 can request that the user interact with the user application 312 in the desired manner.

Upon completion of the functionality lockout process 400, the designated functionality of the application may again be disabled. The functionality lockout process 400 may then, in some implementations, return to block 430 and remain on hold until the time at which to request information from the user has been again reached.

Although the time at which to request the information determined at block 420 may be indicated to the user or understood by the user to be the time for requesting of certain information like the contextual information, the functionality lockout process 400 can further serve to lock out the designated functionality of the user application 312 from the user until after the check-in time. This functionality lockout may be not communicated to the user at block 420 as a reason for requesting the check-in time. The functionality lockout may, however, be later communicated to the user in the event that the user attempts to access or deploy the designated functionality of the user application 312 prior to the check-in time. The functionality lockout can accordingly desirably allow the user to access the user application 312 throughout the day but push the user to at least interact with user application 312 at the check-in time.

Figure 5:
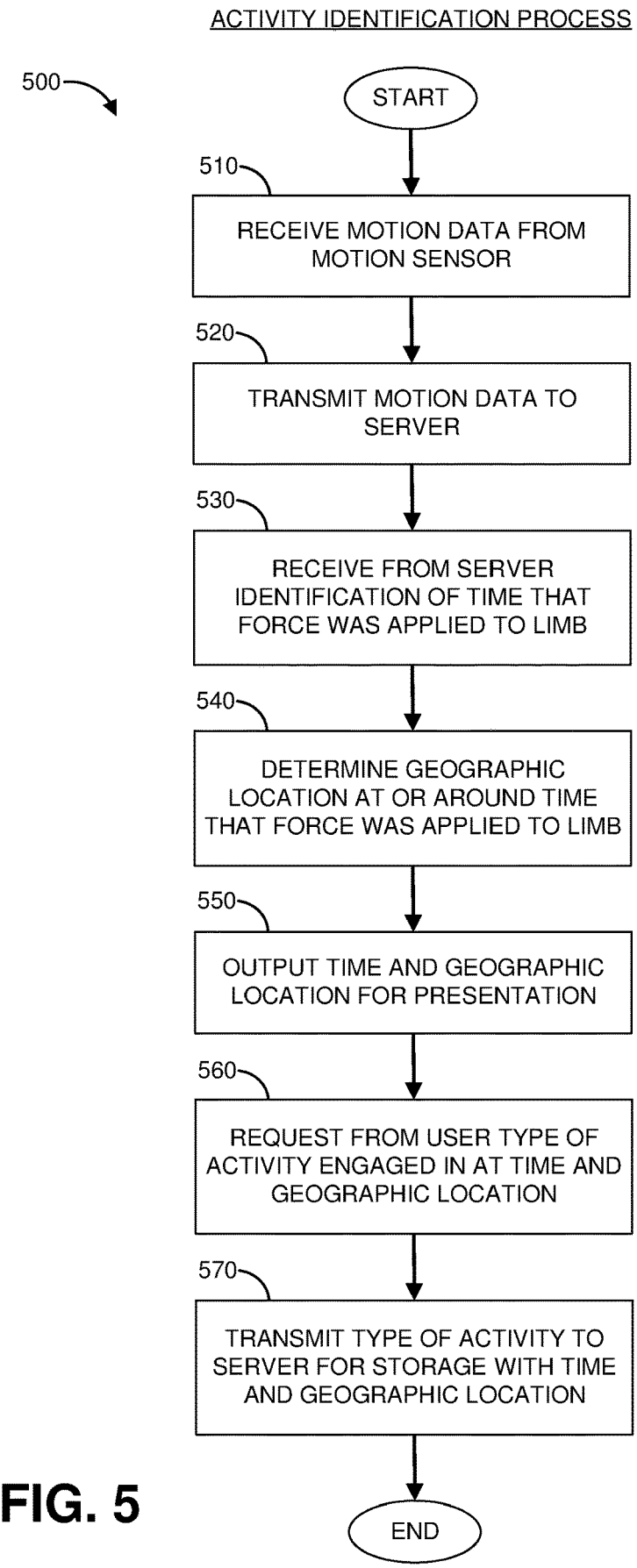
FIG. 5 illustrates an example activity identification process implementable in the computing environment of FIG. 3.

FIG. 5 illustrates an activity identification process 500 for determining a type of activity engaged in by a user at a time and a geographic location of an event which risked adversely impacting an existing ulcer on a foot the user or risked causing a new ulcer on the foot. For convenience, the activity identification process 500 is described in the context of the computing environment 300, but may instead be implemented in other components or systems described herein, or by other computing systems not shown. The activity identification process 500 can advantageously, in certain implementations, assist a user in timely recalling and providing information relevant to the treatment or prevention of an ulcer so that the information can be stored for later access, such as during a consultation between the user and a clinician.

At block 510, the activity identification process 500 can receive motion data from a motion sensor. For example, the user application 312 can receive motion data, such as accelerometer or magnetometer data, from the activity monitoring device 120 via the communication interface 314.

At block 520, the activity identification process 500 can transmit the motion data to a server. For example, the user application 312 can transmit the motion data via the communication interface 314 to the community management system 342 of the device management system 340. The user application 312 may forward the motion data from the activity monitoring device 120 without processing or may process, such as analyze or compress, the motion data prior to forwarding.

At block 530, the activity identification process 500 can receive from the server and identification of a time that a force was applied to a limb of the user, such as when the user was determined to have not been wearing an offloading device. The application of force to the limb without use an offloading device may be referred to as an event. For example, the user application 312 can receive via the communication interface 314 a time (such as a particular instant or time range) from the device management system 340 that the motion data indicates a foot of the user experienced a force which risked adversely impacting existing ulcer on the foot or risked causing a new ulcer on the foot. The data processing system 344 of the device management system 340 may, for instance, have determined the time from analyzing the motion data.

At block 540, the activity identification process 500 can determine a geographic location at or around a time that the force was applied to the name of the user. For example, the geographic location can be a location of the user operation device 310, which may be assumed to match a location of the activity monitoring device 120 at or around the time. The geographic location can be determined by the user application 312 from a global positioning satellite (GPS) receiver of the user operation device 310 or a communication received by the user operation device 310 via the network 330.

At block 550, the activity identification process 500 can output the time and geographic location for presentation. For example, the user application 312 can output the time and geographic location on a graphical user interface for presentation on a display of the user interface 316.

At block 560, the activity identification process 500 can request from the user a type of activity engaged in by the user at the time and geographic location. For example, the user application 312 can output the request on the graphical user interface along with the time and geographic location at block 550. The types of activities can include one or more types of activities described herein, such as a type of transportation (for instance, in a car, on a bus, riding a bike, on a train, on a plane, or walking), a type of exercise (for instance, dog walking, running, swimming, using machines, lifting weights, golfing, bowling, or stretching), a type of leisure (for instance, shopping, entertainment, sightseeing, socializing, going for a stroll, or eating out), a type of home activity (for instance, sitting down, lying down, walking up or down stairs, gardening, cleaning, or cooking), or a type of work (for instance, sitting, walking, manual labor, driving, or standing).

In reply to the request, the user may select one or more of the types of activities, such as by a selection of the one or more types of activities via the user interface 316. In some aspects, the user may select only one of the types of activities. To assist the user with identifying one or more types of activities from numerous different types of activity, the user application 312 may initially present a list of types of activities identified by the user as being types of activities commonly engaged in by the user. The user application 312 can, in turn, receive the selected one or more types of activities.

At block 570, the activity identification process 500 can transmit the type of activity to the server for storage with the time and geographic location. For example, the user application 312 can transmit the type of activity identified by the user to the communication management system 342 for processing by the data processing system 344 and storage in association with the time and geographic location in the data storage 346.

Figure 6:
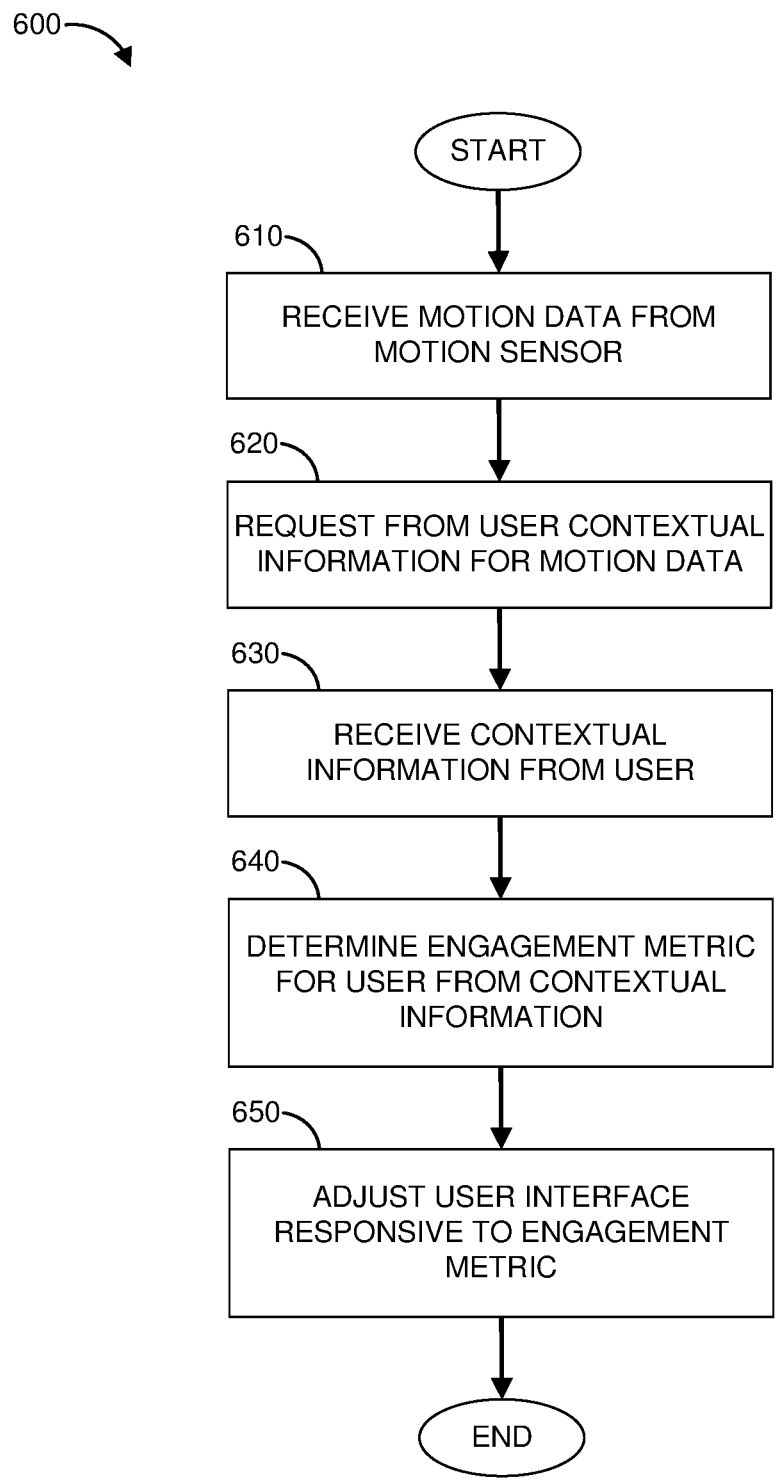
FIG. 6 illustrates an example interface control process implementable in the computing environment of FIG. 3.

FIG. 6 illustrates an interface control process 600 for controlling one or more aspects of a graphical user interface of an application, such as the user application 312, according to an amount of engagement by the user with the user application 312. For convenience, the interface control process 600 is described in the context of the computing environment 300, but may instead be implemented in other components or systems described herein, or by other computing systems not shown. The interface control process 600 can advantageously, in certain implementations, encourage and reward engagement with the user application 312 by the user by changing graphical elements of the application responsive to the engagement.

At block 610, the interface control process 600 can receive motion data from a motion sensor. For example, the user application 312 can receive motion data, such as accelerometer or magnetometer data, from the activity monitoring device 120 via the communication interface 314.

At block 620, the interface control process 600 can request from the user contextual information for the motion data. The user application 312, for example, can request via the user interface 316 that the user provide contextual information for the motion data gathered by the activity monitoring device 120. The contextual information can include an identification of a type of activity associated with an event which risked adversely impacting an existing ulcer on a foot the user or risked causing a new ulcer on the foot. The event can be an application of force to the foot when the user was determined to have not been wearing an offloading device.

At block 630, the interface control process 600 can receive the contextual information from the user. For example, the user may select one or more of the types of activities, such as by a selection of the one or more types of activities via the user interface 316. In some aspects, the user may select only one of the types of activities. To assist the user with identifying one or more types of activities from numerous different types of activity, the user application 312 may initially present a list of types of activities identified by the user as being types of activities commonly engaged in by the user. The user application 312 can, in turn, receive the selected one or more types of activities. The contextual information may include additional or alternative information, such as how the user felt that day or the condition of the user's foot or ulcer, or may include interactions between the user and the user application 312 that may be considered desirable engagement.

At block 640, the interface control process 600 can determine an engagement metric for the user from the contextual information. The engagement metric can be indicative of an amount of engagement by the user with the application. The engagement metric can be determined from a count of a number of days (or other time periods) for which the user provided the contextual information or a number of consecutive days (or other time periods) for which the user provided the contextual information. For example, the user application 312 can determine the engagement metric from or to be a count of the number of days for which the user provided the contextual information. In instances where the user may have provided partial but not all requested conjectural information for a particular day, the user application 312 may not include that particular day in the count.

At block 650, the interface control process 600 can adjust a user interface, such as a graphical user interface, responsive to the engagement metric. For example, the user application 312 can adjust a graphical user interface generated by the user application 312 and output the graphical user interface for presentation on a display of the user interface 316. The graphical user interface may be adjusted, for instance, by (i) presenting to the user feedback that was selected from one set of feedback options rather than another set of feedback options, (ii) changing the formatting of information included in the graphical user interface, or (iii) incorporating one image rather than another image in the graphical user interface. The graphical user interface can be adjusted differently if the engagement metric satisfies a threshold than if the engagement metric does not satisfy the threshold.

The adjustment in the user interface at block 650 can desirably, in certain aspects, encourage the user to continue to engage with the user application 312 by, for example, providing positive feedback to the user (such as through permitting the user to advance through multiple levels, awarding the user virtual awards to celebrate accomplishments by the user, or increase an aesthetic appeal of the user application 312), giving the user enhanced access to information (such as permitting the user to have additional information about treatment), or relaxing some expectations for engaging with the user application 312 (such as no longer requiring the user to provide certain information or requesting information in a more concise manner which permits the user to view fewer graphical user interfaces or provide fewer inputs).

FIGS. 7A-7G illustrate example user interfaces that can be presented by the user application 312 on the user interface 316 of the user operation device 310 and assist with introducing a user to operation of the user application 312, engaging the user with the user application 312, and initiating collection of information by the user application 312.

Figure 7B:
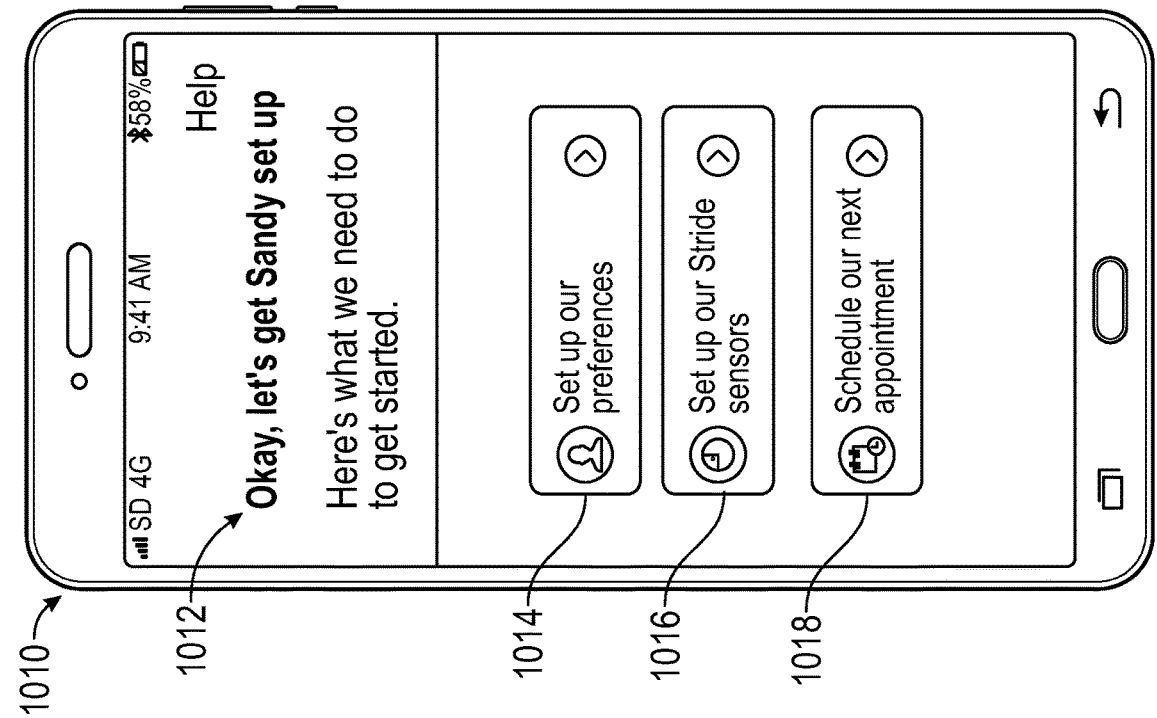
FIG. 7B illustrates an example configuration interface presentable in the computing environment of FIG. 3.
Figure 7A:
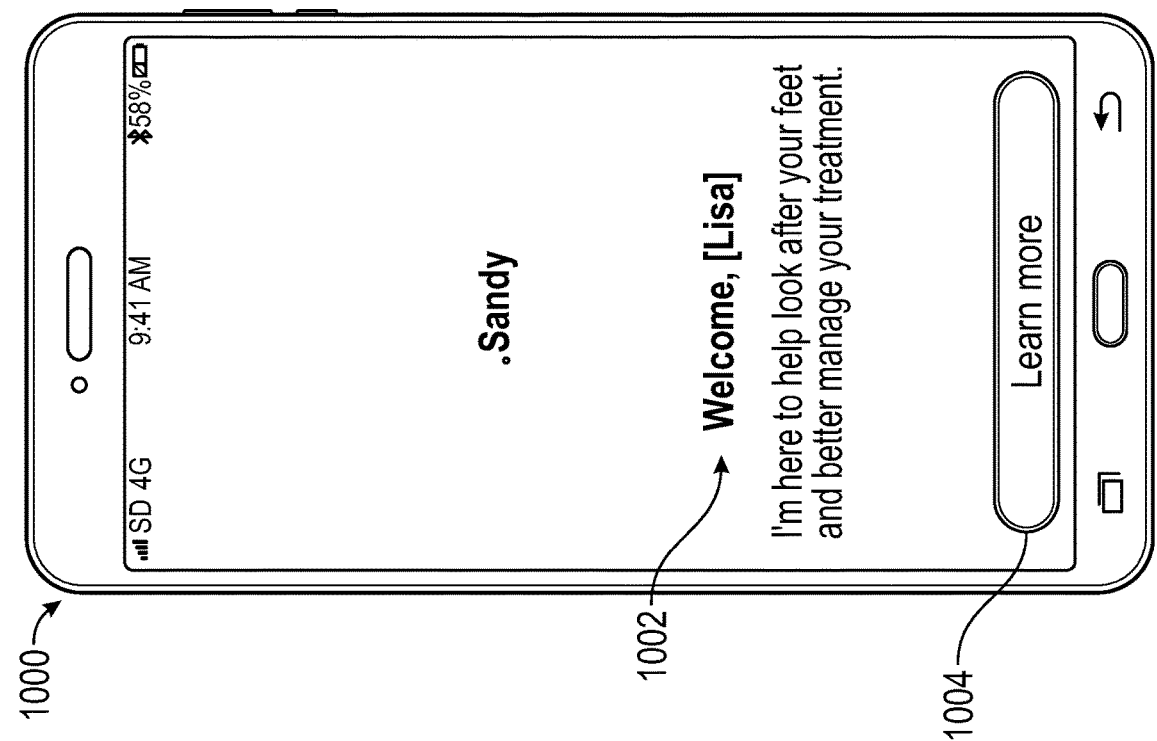
FIG. 7A illustrates an example welcome interface presentable in the computing environment of FIG. 3.
Figure 7D:
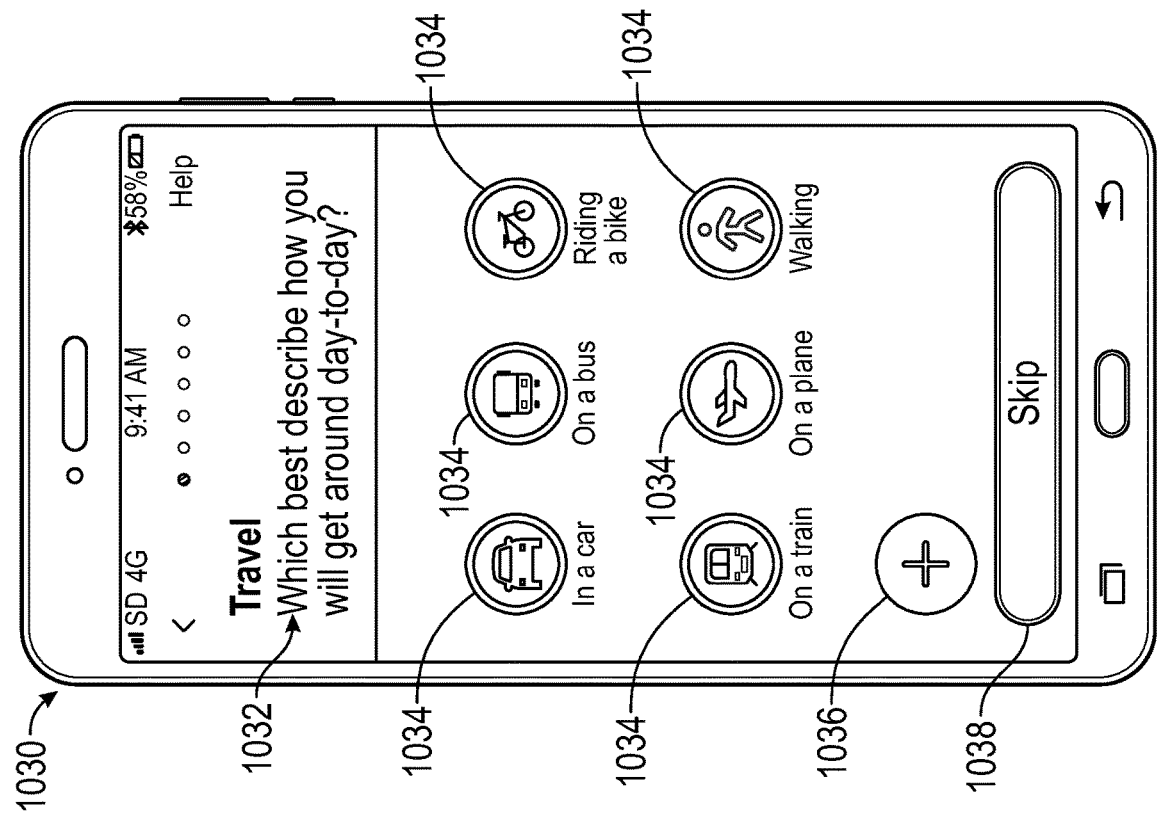
FIG. 7D illustrates an example travel type interface presentable in the computing environment of FIG. 3.

FIG. 7A illustrates an example welcome interface 1000 that can present a customized message 1002, such as a user's name or other user or wound-specific message, and an learn more element 1004. The learn more element 1004 can, upon selection by a user, transition the user interface 316 to present a configuration interface 1010, which is shown in FIG. 7B.

The configuration interface 1010 can provide an introductory message 1012 and include selectable elements 1014, 1016, and 1018. The selectable elements 1014, 1016, and 1018 can each transition the user application 312 to different configuration screens that may be part of a user onboarding or setup process for the user application 312.

Figure 7C:
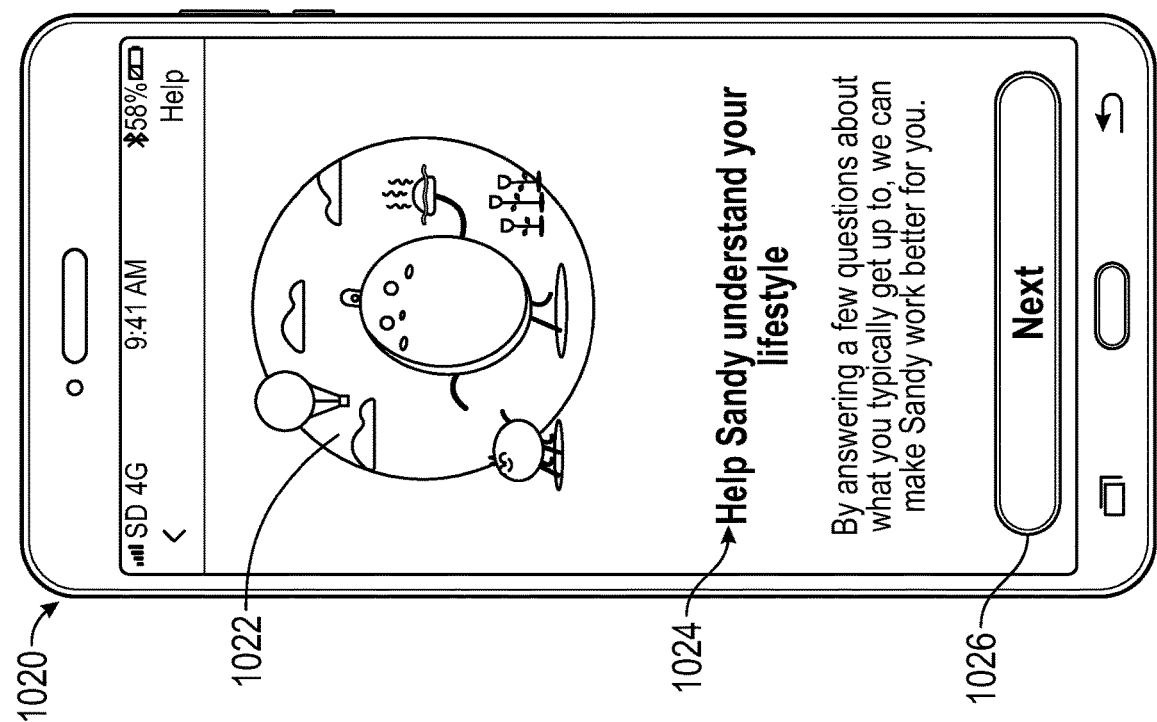
FIG. 7C illustrates an introduction interface presentable in the computing environment of FIG. 3.

FIG. 7C illustrates an introduction interface 1020 that may be presented upon completion of application configuration through the configuration interface 1010. The introduction interface 1020 can include a character 1022 (sometimes referred to as an avatar) that may be used to improve engagement with the user application 312. As described further herein, the character 1022 may be customized by the user to adjust how the user receives information from the user application 312. The introduction interface 1020 can have an instructional message 1024 and a next element 1026. Selection of the next element 1026 by a user can trigger a transition by the user interface 316 to a travel type interface 1030 shown in FIG. 7D.

As shown, the travel type interface 1030 can present a travel type request 1032, which can indicate that the user is requested to identify one or more types of transportations which the user commonly utilizes to travel. The travel type interface 1030 can also include selectable travel type elements 1034 that permit the user to indicate one or more specific types of transportation to the user application 312. This information can, for example, enable the user application 312 to determine the types of transportation utilized by the user to provide more efficient display of data or enable the user to more efficiently input event data. The travel type interface 1030 can include a selectable custom element 1036, which may permit the user to provide a custom activity type input, and a selectable skip element 1038, which may allow the user to elect not to select one or more of the selectable travel type elements 1034 or the selectable custom element 1036.

The user application 312 may transition to an exercise type interface 1040 shown in FIG. 7E after presenting the travel type interface 1030. The exercise type interface 1040 can present an exercise type request 1042, which can indicate that the user is requested to identify one or more types of exercise which the user commonly engages in. The exercise type interface 1040 can also include selectable exercise type elements 1044 that permit the user to indicate one or more specific types of exercise to the user application 312. This information can, for example, enable the user application 312 to determine the types of exercise engaged in by the user to provide more efficient display of data or enable the user to more efficiently input event data. The exercise type interface 1040 can include a selectable custom element 1046, which may permit the user to provide a custom exercise type input, and a selectable skip element 1048, which may allow the user to elect not to select one or more of the selectable exercise type elements 1044 or the selectable custom element 1046.

Although not illustrated, the user application 312 may transition to other activity type interfaces, including a leisure type interface, a home activity interface, a work type interface, or an assisted movement interface. These interfaces can be configured similarly to the travel type interface 1030 or the exercise type interface 1040. The leisure type interface can present a leisure type request, which can indicate that the user is requested to identify one or more types of leisure that the user commonly engages in which, similar to the exercise type interface, can include selectable leisure type elements that facilitate the user's input of such activities. The work type interface can be similarly configured to the exercise and leisure type interface and may additionally be preceded by a work qualifier interface that requests a user to indicate whether the user will be working during the wearing of the activity monitoring device 120. If the user indicates that the user will be wearing the activity monitoring device 120, then the user may be presented with the work type interface which can request the user to identify one or more types of work activities that the user will be commonly be engaged in, along with respective selectable elements. If the user indicates that the user will not be wearing the activity monitoring device 120, then the user application 312 may not present the work type interface and proceed to another user interface. The assisted movement interface can present an assisted movement request, which can indicate that the user is requested to identify one or more manners or modes of assisted movement that the user will use. As with the other activity interfaces, the assisted movement interface can include selectable assisted movement type elements that facilitate the user's input of what type of assisted movement device the user may use while wearing the activity monitoring device 120.

FIG. 7F illustrates a user goal interface 1050 that can be used to collect additional goal data form the user for the user application 312. As shown, the user goal interface 1050 can have a goal add element 1056, which enables to user to enter a new goal, and selectable goal elements 1054, each relating to a different goal provided by the user or a clinician for the user. This information can assist the user application 312 in tracking information about the performance of activities or behaviors by the user to assist the user in remaining accountable for actions, such as goals related to a therapy for the user.

Figure 7H:
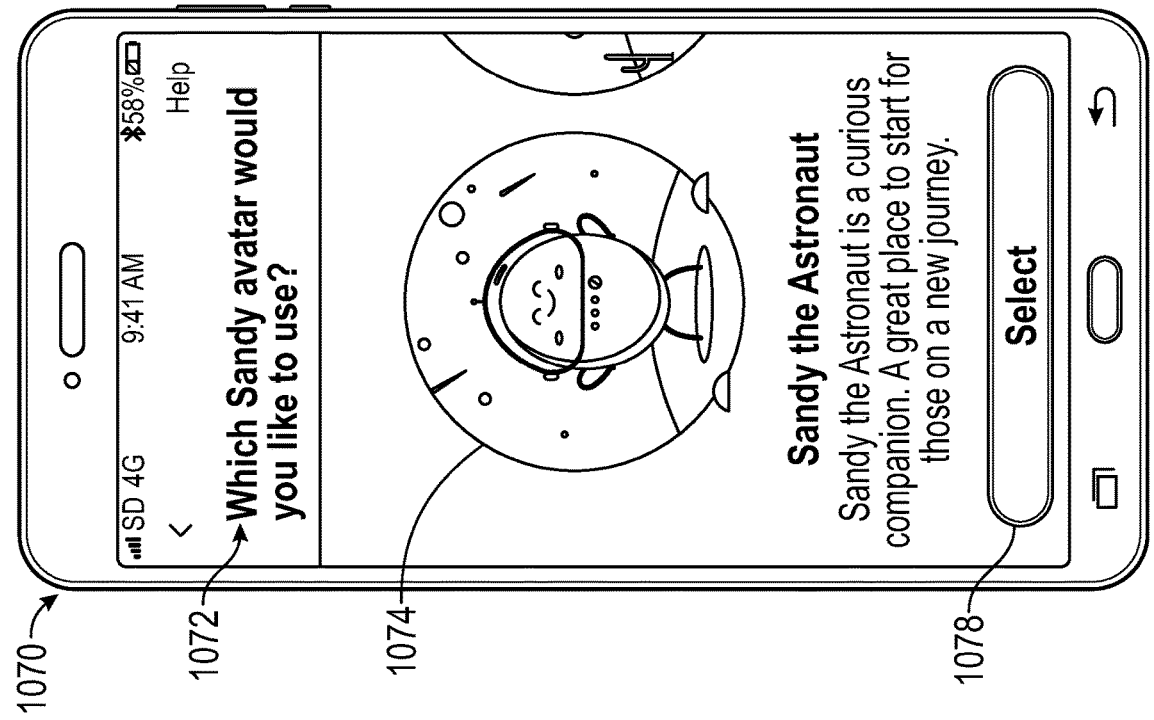
FIG. 7H illustrates an example character select interface presentable in the computing environment of FIG. 3.
Figure 7G:
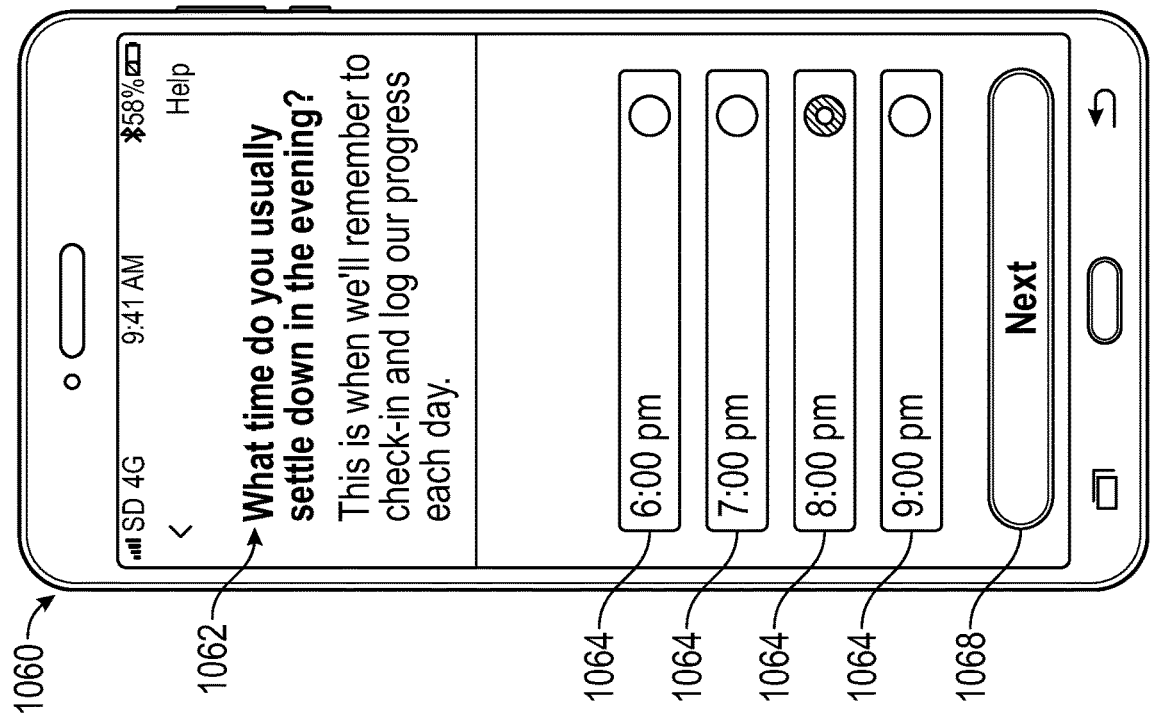
FIG. 7G illustrates an example check-in setting interface presentable in the computing environment of FIG. 3.

FIG. 7G illustrates a check-in setting interface 1060 that can be used to determine a time at which the user may be prompted to provide information related to treatment. As shown, the check-in setting interface 1060 can present a time request 1062, which may prompt for a time of day at which the user typically settles down and reduces his or her activity, and include selectable time elements 1064, each corresponding to a different time at which the user may elect to check-in. The time provided by the user via the selectable time elements 1064 can assist the user application 312 in customizing the time that information related to therapy is requested from the user, as well as permit the user application 312 to disable certain of its functionality to encourage engagement with the user application 312 subsequent to the user setting down and reducing activity for the day. The check-in setting interface 1060 can include a next selectable element 1068 that may allow the user to submit the time selected by the selectable time elements 1064 to the user application 312 and progress to a next user interface, such as a character select interface 1070 shown in FIG. 7H.

The character select interface 1070 can permit the user to set a preferred character that will be used in various user interfaces of the user application 312. The character select interface 1070 can present a character request 1072, which asks a user to identify which character the user prefers, and changeable character elements 1074. The character select interface 1070 can include a select element 1078 that allows the user to confirm the selection of the identified character element and advance to another user interface. The character selected by the user can, in some aspects, be the centerpiece of a user experience for the user application 312 and influence how the user application 312 engages with the user, such as the type of encouragement or language used in communicating information or progress to the user.

FIGS. 8A-8L illustrate example user interfaces that can be presented by the user application 312 on the user interface 316 of the user operation device 310 and may remind the user about providing information to the user application 312 and permit the user to input the information.

Figure 8B:
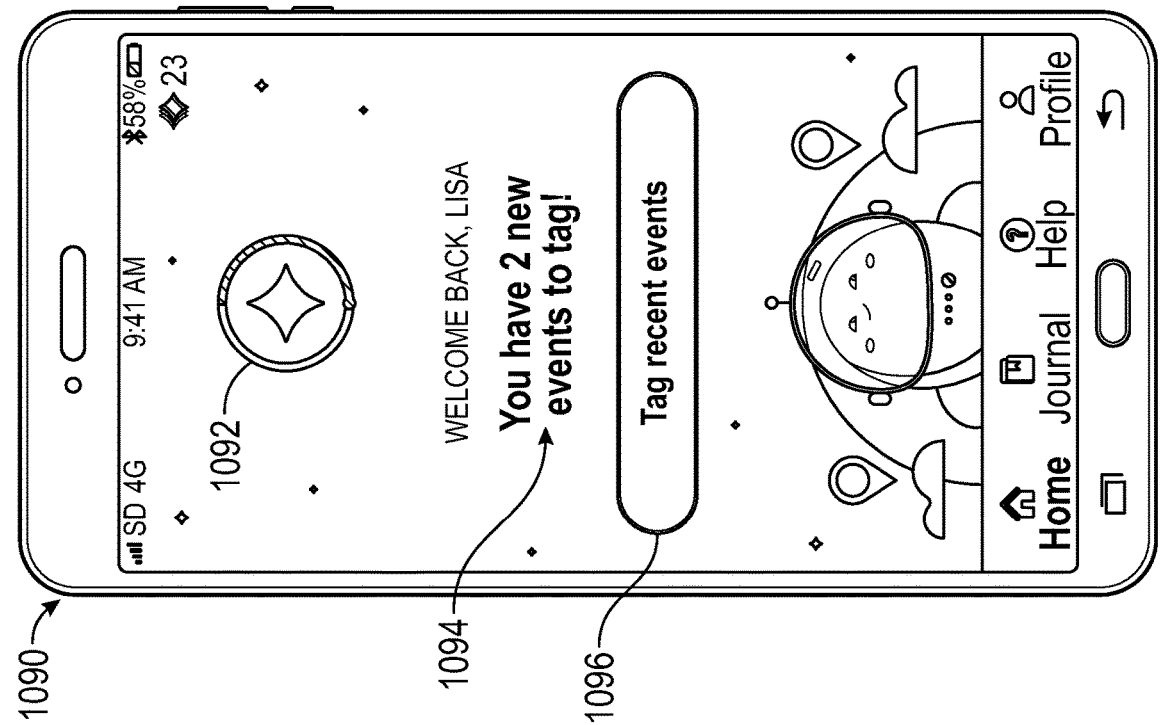
FIG. 8B illustrates an example event status interface presentable in the computing environment of FIG. 3.
Figure 8A:
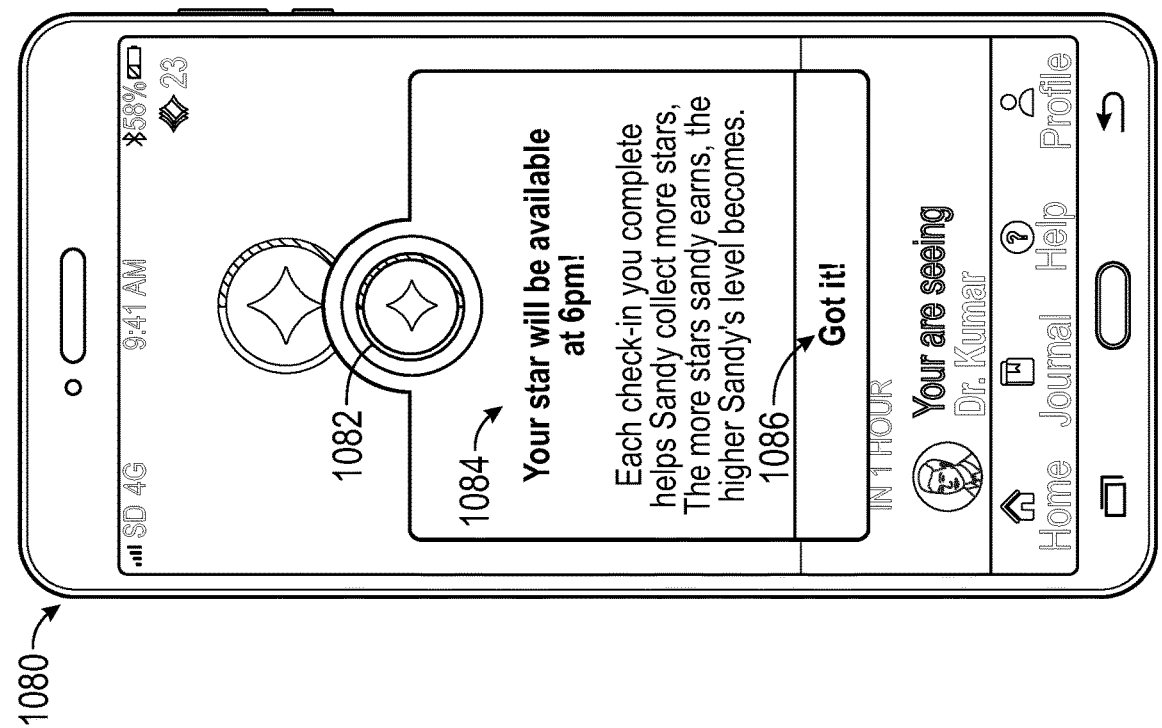
FIG. 8A illustrates an example check-in status interface presentable in the computing environment of FIG. 3.
Figure 8D:
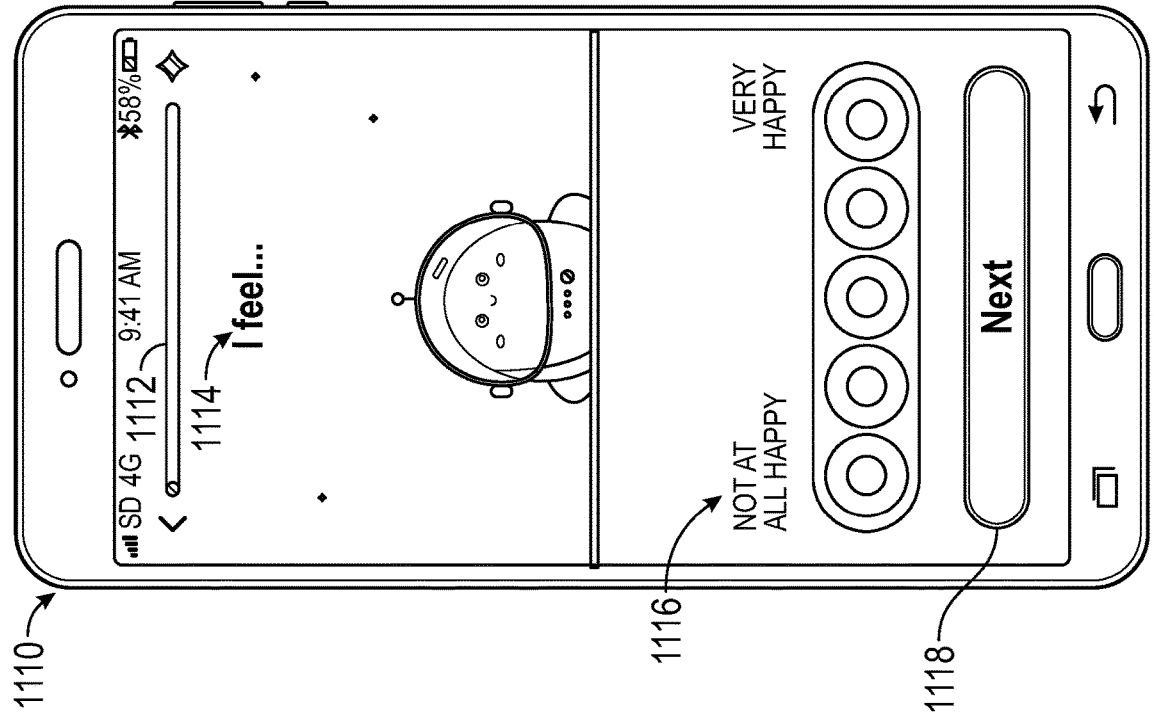
FIG. 8D illustrates an example wellness feedback interface presentable in the computing environment of FIG. 3.

FIG. 8A illustrates a check-in status interface 1080 that prompts or reminds the user when a time for input of context information is scheduled to occur. The user application 312 can present the check-in status interface 1080 when a user attempts to access a certain user interface or input certain data, such as data or feedback regarding a state of wellness of the user as described with respect to FIGS. 8D-8F, before the time permitted for such access or input has been reached (for example, the time at which such access or input may be permitted can start when the time to request information from the user has been reached as described with respect to block 430 of FIG. 4). The check-in status interface 1080 can present an informational message 1084 that can alert the user when the check-in time is scheduled. The time presented in the informational message 1084 can correspond with the time that the user input via the check-in setting interface 1060 during the onboarding or setup phase. The check-in status interface 1080 can present a status indicator 1082 that may provide visual feedback to the user when the time will occur or that the time has occurred, or that the ability for the user to activate or engage in a particular interaction with the user application 312 has not yet occurred. When the status indicator 1082 appears as a partial outline of a circle and without a token (illustrated as a center star) being filled as illustrated in FIG. 8B, the status indicator 1082 may signify that the time has not yet been reached. A selectable confirmatory element 1086, when selected by the user, cause a transition from the check-in status interface 1080 to a subsequent user interface.

FIG. 8B illustrates an event status interface 1090 that can present the user with an informational message 1094 to inform the user of a number of events that may remain untagged (for instance, a count of events for which the user has not yet provided contextual information). As described herein, an event can, for example, be an application of force to a limb of a user when the user was determined to have not been wearing an offloading device. A status indicator 1092 can present visual feedback to the user and may be the same as or similar to the status indicator 1082. A tag event element 1096, when selected, can transition the user application 312 from the event status interface 1090 to another interface that may request that the user input the information regarding untagged events. The user application 312 may display the event status interface 1090 prior to the time being reached.

Figure 8C:
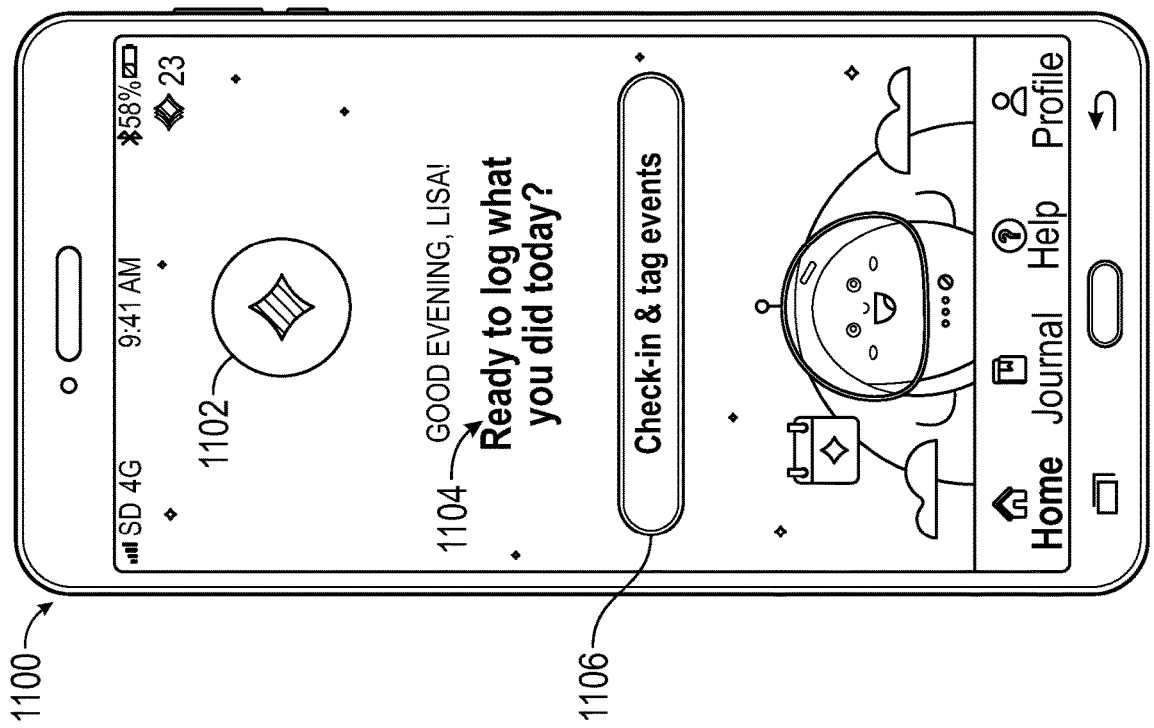
FIG. 8C illustrates an example tag log initiation interface presentable in the computing environment of FIG. 3.
Figure 8F:
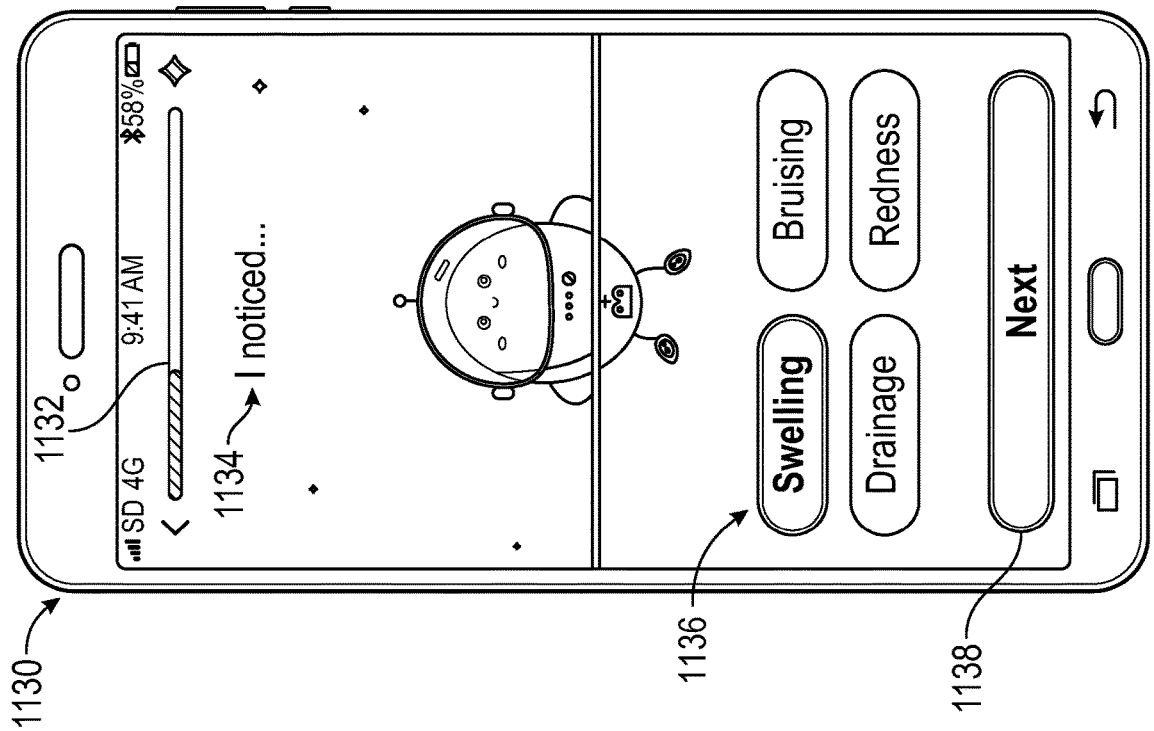
FIG. 8F illustrates an example observation user interface presentable in the computing environment of FIG. 3.
Figure 8E:
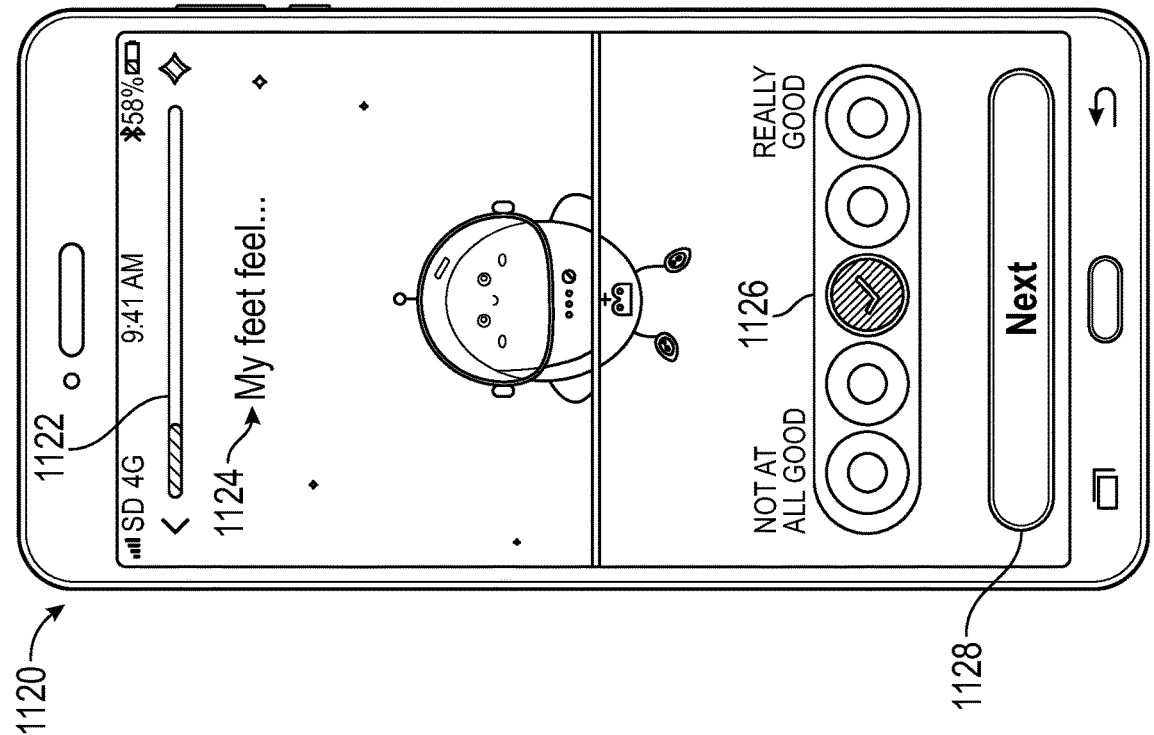
FIG. 8E illustrates an example foot health feedback interface presentable in the computing environment of FIG. 3.
Figure 8H:
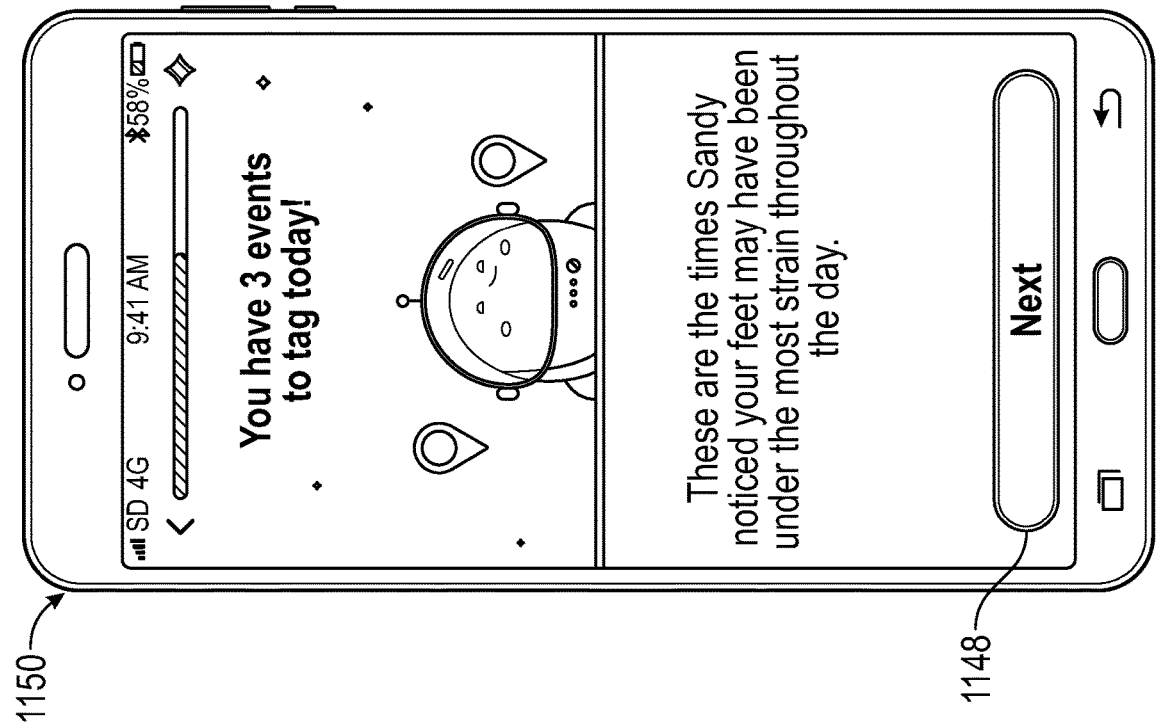
FIG. 8H illustrates an example untagged event summary interface presentable in the computing environment of FIG. 3.
Figure 8G:
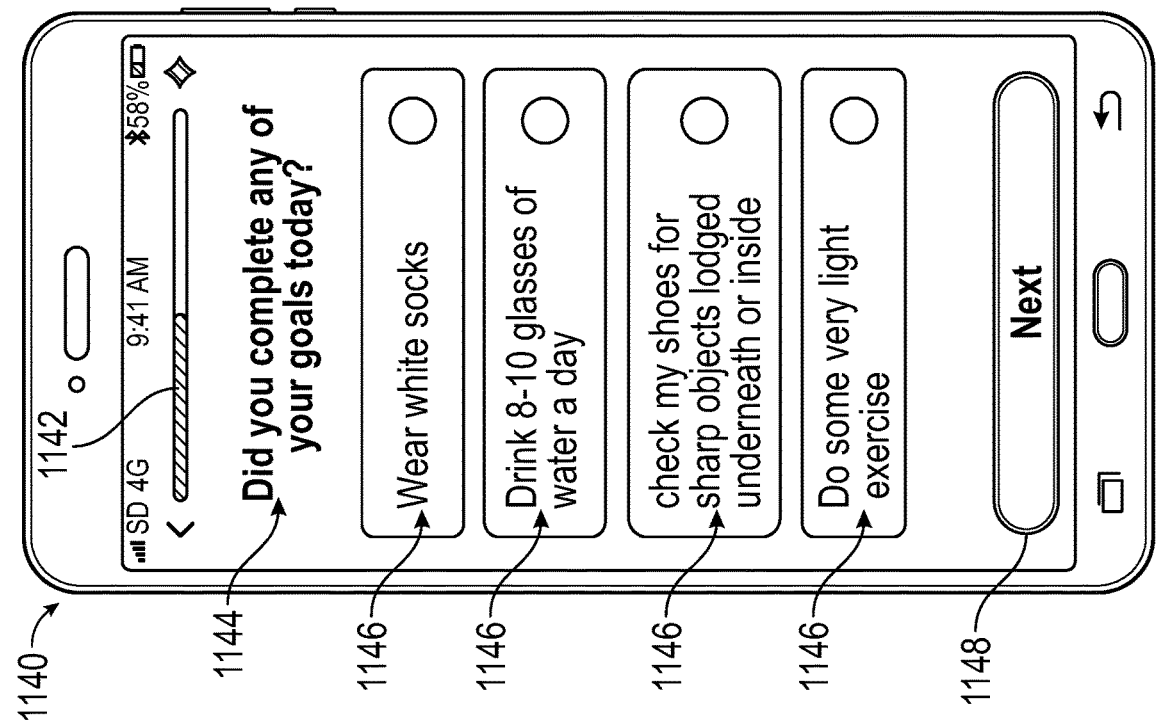
FIG. 8G illustrates an example goal completion interface presentable in the computing environment of FIG. 3.

FIG. 8C illustrates a tag log initiation interface 1100 that prompts the user to check in to provide the contextual information. When the status indicator 1102 appears with a token (illustrated as a center star) being filled in and without an outline of a circle as illustrated in FIG. 8A, the status indicator 1082 may signify that the time has been reached and that the user may now earn the token though completion of a check-in process (where the earning of the token may be a positive reward for the user and serve as a feedback for the user or clinician for tracking the user's utilization of the user application 312). The user application 312 may display the tag log initiation interface 1100 responsive to the time being reached. An instructional message 1104 can prompt the user to check in and tag any untagged events. A tag events selectable element 1106, when selected by the user, can trigger the user application 312 to transition from the tag log initiation interface 1100 to a subsequent user interface, such as a wellness feedback interface 1110 shown in FIG. 8D, for inputting the contextual information. The presentation of the tag log initiation interface 1100 by the user application 312 can, for example, indicate an enabling of disabled functionality of the user application 312, such as described respect to block 440 of FIG. 4, because the tag log initiation interface 1100 may provide access to at least some previously unavailable functionality of the user application 312.

The wellness feedback interface 1110 may request that the user input information regarding a state of wellness of the user. The wellness feedback interface 1110 can request that user provide a level of happiness of the user on a five-unit scale from "not happy at all" to "very happy". A wellness status bar 1112 can present a visual status indication of the user's progress through a check-in process, such as a portion of feedback questions of the check-in process that have been answered or are remaining for the user to answer. The wellness feedback interface 1110 can present a feedback question or prompt 1114 (regarding a first condition like "I feel . . . "), list data input that is desired, and selectable wellness elements 1116, each characterizing a different response to the feedback question or prompt 1114. Additionally, a next selectable element 1118 can, upon selection by the user, transition the user application 312 from the wellness feedback interface 1110 to a subsequent user interface, which can be a foot health feedback interface 1120 shown in FIG. 8E.

The foot health feedback interface 1120 may present a feedback question or prompt 1124 (regarding a second condition like "My feet feel . . . "). A wellness status bar 1122 may show the wellness status bar 1112 after completion of the feedback question or prompt 1114. The foot health feedback interface 1120 can present selectable feedback elements 1126, each characterizing a different response to the feedback question or prompt 1124, and a next selectable element 1128 by which the user can confirm the entry of the response to the feedback question or prompt 1124 and cause the user application 312 to transition from the foot health feedback interface 1120 to a subsequent user interface, such as an observation feedback interface 1130 shown in FIG. 8F.

The observation feedback interface 1130 can present a feedback question or prompt 1134 regarding a third condition, such as "I noticed . . . " to request information regarding one or more conditions of the user's foot or wound area, including observations of swelling, bruising, drainage, or redness. The observation feedback interface 1130 can include selectable elements 1136, each characterizing a different response to the feedback question or prompt 1134. A wellness status bar 1132 may show the wellness status bar 1112 after completion of the feedback question or prompt 1114 and the feedback question or prompt 1124. The observation feedback interface 1130 can present a next selectable element 1138 by which the user can confirm the entry of the response to the feedback question or prompt 1134 and cause the user application 312 to transition from the observation feedback interface 1130 to a subsequent user interface, such as a goal completion interface 1140 shown in FIG. 8G.

The goal completion interface 1140 can present a feedback question or prompt 1144 (for example, a question for the user about the user's goals that were previously input by the user via the user goal interface 1050 illustrated in FIG. 7F). A wellness status bar 1142 may show the wellness status bar 1112 after completion of the feedback question or prompt 1114, the feedback question or prompt 1124, and the feedback question or prompt 1134. The goal completion interface 1140 can include selectable goal elements 1146, each characterizing a different response to the feedback question or prompt 1144. The goal completion interface 1140 can extend beyond a single screen space on the user interface 316 such that the user may, for instance, swipe or scroll up or down to view an entirety of the goal completion interface 1140, including additional goals. The goal completion interface 1140 can present a next selectable element 1148 by which the user can confirm the entry of the response to the feedback question or prompt 1144 and cause the user application 312 to transition from the goal completion interface 1140 to a subsequent user interface, which can optionally be an untagged event summary interface 1150 shown in FIG. 8H.

The untagged event summary interface 1150 can indicate a number of events (for example, three events as illustrated) for which the user is requested to provide contextual information (for example, information about a type of activity engaged in by the user when an event occur, which may be referred to as tagging). A selectable next element is also included for advancing to another user interface, such as a geographic location interface 1160 illustrated in FIG. 8I.

The geographic location interface 1160 can be used to request that the user consider contextual information regarding an event. The geographic location interface 1160 may present event information 1162, including a time (which may also be a time range as shown) and a location of the event, to remind the user of the time and the location that the event occurred. The event information 1162 can, for example, provide the time and the location of the event as described with respect to block 550 of FIG. 5. A boot image 1163 can denote that the user was determined to have been wearing an offloading device during the event. The user application 312 may have received the time, the location, and the determination of wearing the offloading device from the device management system 340, such as in response to a request from the user operation device 310 or a push notification from the device management system 340. A map image 1164 can be used to depict the location of the user or the user operation device 310 at the time of the event. A location input element 1166 can, upon selection by the user, transition the user application 312 from the geographic location interface 1160 to a different user interface, such as an activity input interface 1170 shown in FIG. 8J.

The activity input interface 1170 can display event information 1172, which can be the same as the event information 1162. The activity input interface 1170 can prompt the user to provide activity category information 1174 by requesting that the user select the category of activity engaged in by the user at the time and the location of the event. The activity category information 1174 may be an example of the request from the user described with respect to block 560 of FIG. 5 and block 620 of FIG. 6. The activity category information 1174 can include activity description categories 1176, which can be selected by the user to input the category of activity that the user was engaged in during the event. The activity description categories 1176 can, for example, include home (to indicate that the user was at home), leisure (to indicate that the user was engaged in leisure), travel (to indicate that the user was traveling), work (to indicate that the user was working), exercise (to indicate that the user was engaged in exercise), or an I don't remember category (to indicate that the user does not recall what type of activity was being engaged in).

The activity description categories 1176 can, upon selection by the user, transition another user interface that prompts the user to input a type of activity within the selected category that the user was engaged in at the time and the location of the event. In some aspects, a category of activity may be the same as a type of activity rather than a group of types of activities as described in this example. A close element 1178 can be selected to confirm that the user has completed the input of the category or type information requested in the activity input interface 1170 and to transition from the activity input interface 1170 to a subsequent interface, such as a tagged event summary interface 1180 illustrated in FIG. 8K.

The tagged event summary interface 1180 can show a summary image 1182 representative of the type of activity that has been identified by the user for the event, as well as the time and a map showing the location of the event. The information presented on the tagged event summary interface 1180 can be confirmed by the user by selection of a save element 1188. The selection of the save element 1188 may prompt the user application 312 save the information for the event and transmit at least the type of activity identified by the user for storage by the device management system 340 in associate with the event, time, or location. The example of FIG. 8K shows that the user selected the exercise using machines as the type of activity that the user was engaged in during the event.

Although FIG. 8J illustrates that the user may navigate through selection of one or more categories or prior to selection of one or more types of activities, in some aspects, the user can instead be presented on the activity input interface 1170 with multiple activity description categories or types that may correspond to different activity types previously indicated by the user (such as via the travel type interface 1030 or the exercise type interface 1040) to be types of activities commonly engaged in by the user.

Figure 8L:
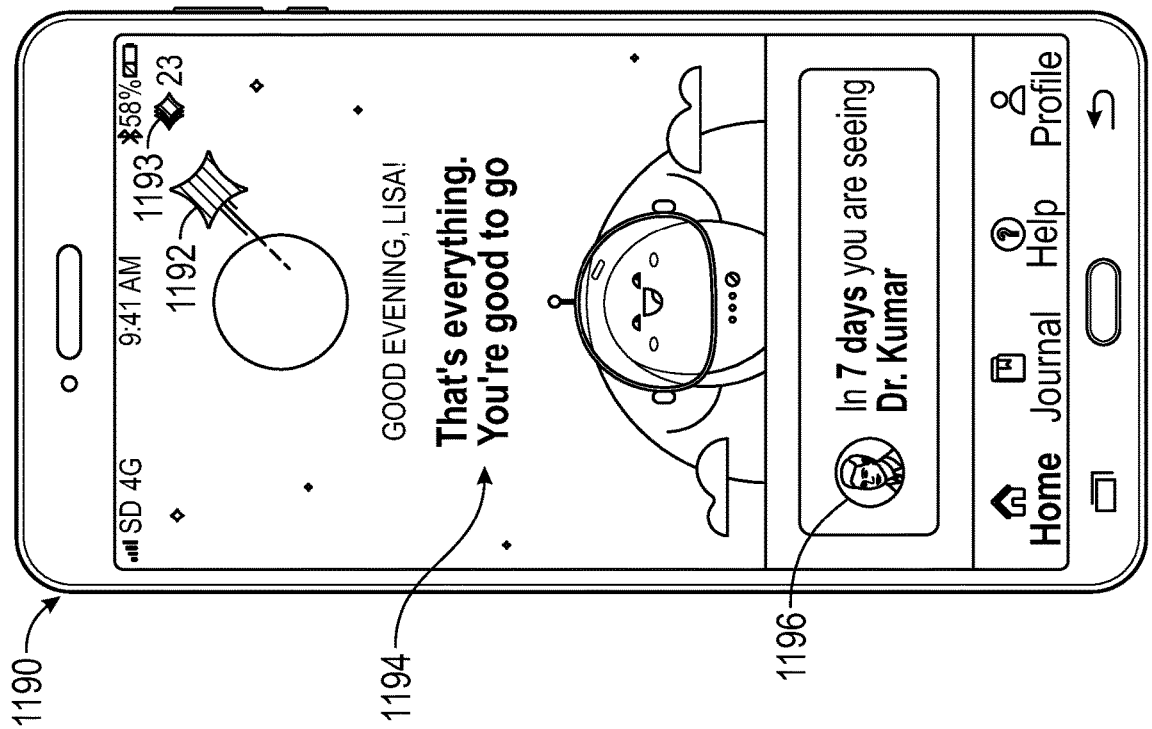
FIG. 8L illustrates an event confirmation interface presentable in the computing environment of FIG. 3.
Figure 8K:
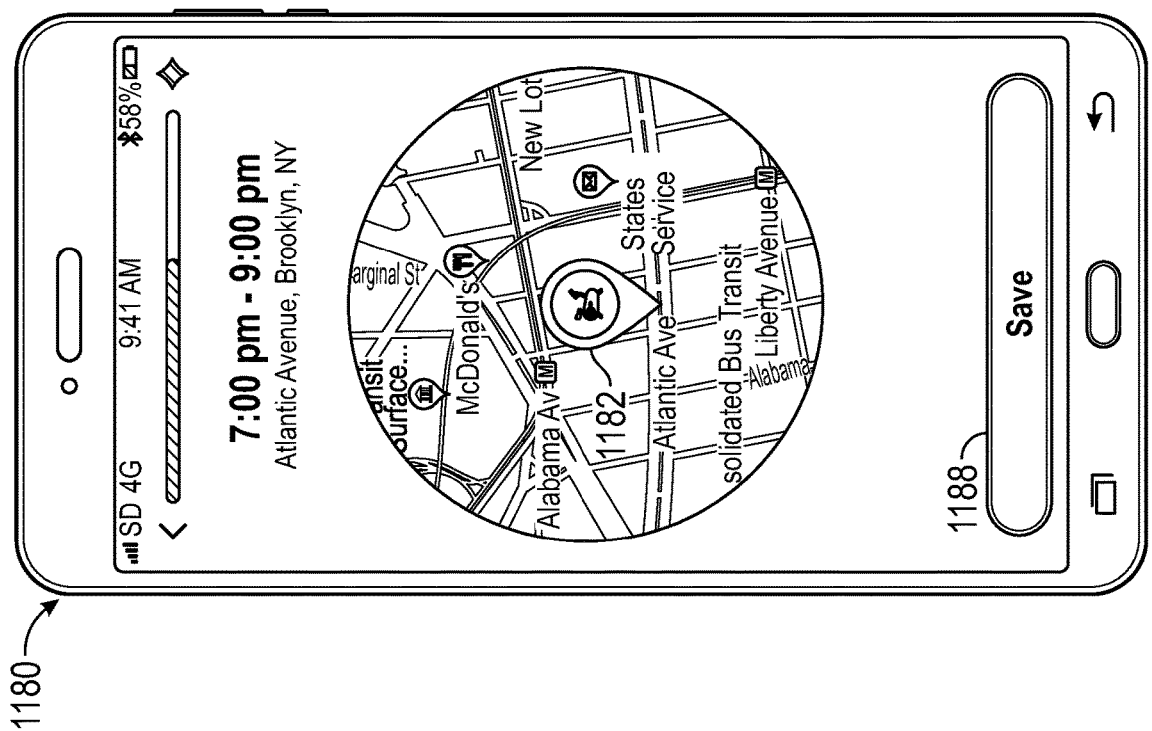
FIG. 8K illustrates an event summary interface presentable in the computing environment of FIG. 3.

FIG. 8L illustrates an event confirmation interface 1190 that may provide feedback to the user regarding the completion of the requested inputs for the check-in process. The event confirmation interface 1190 can show a token 1192 (which can be any symbol, such as a star) transitioning to a total token count 1193. The total token count 1193 can represent a total number of times the user successfully input all of the requested information for a check-in process and may be maintained by the user application 312. An information status 1194 can confirm by text the successful completion of the check-in process. The event confirmation interface 1190 can also display an appointment reminder 1196 for an upcoming doctor appointment.

FIGS. 9A-9G illustrate example user interfaces that can be presented by the user application 312 on the user interface 316 of the user operation device 310 to provide summaries of monitoring, activities, events, or determinations for a user. The summaries may assist in the monitoring and treatment of a foot ulcer on the user. The summaries can be presented to cover data collected over or determined with respect to a selectable length of time, such as over few hours or less, one day, multiple days, one or more weeks, or longer.

Figure 9A:
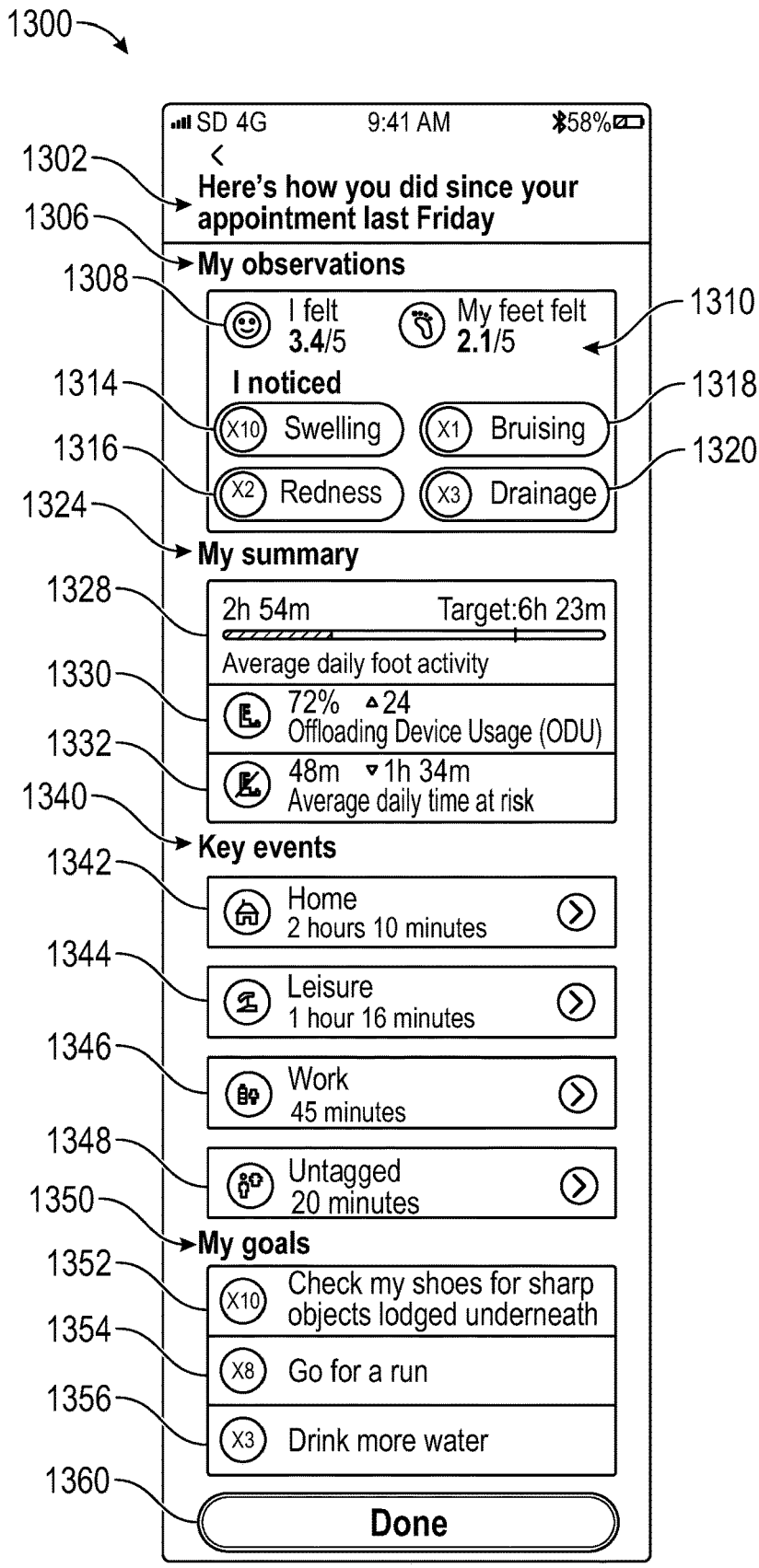
FIG. 9A illustrates an example user summary interface presentable in the computing environment of FIG. 3.

FIG. 9A illustrates a user summary interface 1300 that can present a range of summary information to the user. The user summary interface 1300 can include an overview message 1302 indicating a subject of the content to be presented and a time period that the summary information pertains to (for example, the illustrated aspect presents a summary of the information collected by the user application 312 or determined for the user since "last Friday") The summary information can include user observations 1306, such as a user feeling summary 1308 (which can present an average of the feeling data from the user on a five point scale regarding how the user felt during the time period and include a graphical symbol, such as a happy face or a sad face, to graphically communicate the feeling) a foot feeling summary 1310 (which can present an average of the feeling data from the user on a five point scale of regarding how the user's feet felt during the time period and include a graphical symbol, such as a bare foot, to graphically communicate the feeling).

The user summary interface 1300 can present a number of occurrences during the time period that the user indicated swelling 1314, redness 1316, bruising 1318, and drainage 1320 at the user's feet or foot wound. The user summary interface 1300 can present a summary of any other desired or meaningful observations that were input or selected by the user during user onboarding or a setup process for the user application 312. The user summary interface 1300 can present summary data 1324, such as actual and target average daily foot activity 1328 (for example, where actual is illustrated to be 2 hours and 54 minutes and target is illustrated to be 6 hours 23 minutes), offloading device usage 1330 (for example, where usage is illustrated to be 72% and up 24% from a previous period), and average daily time at risk 1332 (for example, where time at risk is illustrated to be 48 minutes which may be down 1 hour and 34 minutes from a previous period). The time at risk can refer to an amount of time during which a limb of the user may be active while an offloading device is not in use.

The user summary interface 1300 can present the user with a key events summary 1340, which can include a presentation of an amount of time the user spent engaging in particular activities during events. Such events can be grouped by category or type of activity and may include home time 1342, leisure time 1344, work time 1346, and untagged time 1348.

The home time 1342, leisure time 1344, work time 1346, and untagged time 1348, can be user selectable elements that, when selected by the user, expand the user summary interface 1300 to another user interface (such as a home interface 1370 illustrated in FIG. 9B) to present the user with additional information (for example, a total duration of events that occurred at the time/location, an increase or decrease in the total duration relative to a previous period, an offloading device usage, an amount of time at the time/location at which the user engaged in particular types of activities, a number of occurrences of events for particular types of activities, an average time per event for particular types of activities, a number of impacts for particular types of activities, an offloading device usage percentage for particular types of activities, or an assisted movement usage percentage for particular types of activities) regarding the selected one of the key events summary 1340.

The user summary interface 1300 can present a user with a goal occurrences summary 1350, which can include a presentation of a number of times that the user achieved individual goals. The goals can include the goals that the user input during the user onboarding or setup process for the user application 312. Examples of goals that can be presented include "Check my shoes for sharp objects lodged underneath", as shown a first goal 1352, "Go for a run" as a second goal 1354, and "Drink more water" as a third goal 1356. The goals can be ordered according to a number of times that the goal was achieved (such as, from highest to lowest number of occurrences or vice versa). The user summary interface 1300 can have a done element 1360, the selection of which by the user can trigger a transition by the user application 312 to a different or subsequent user interface.

Figure 9C:
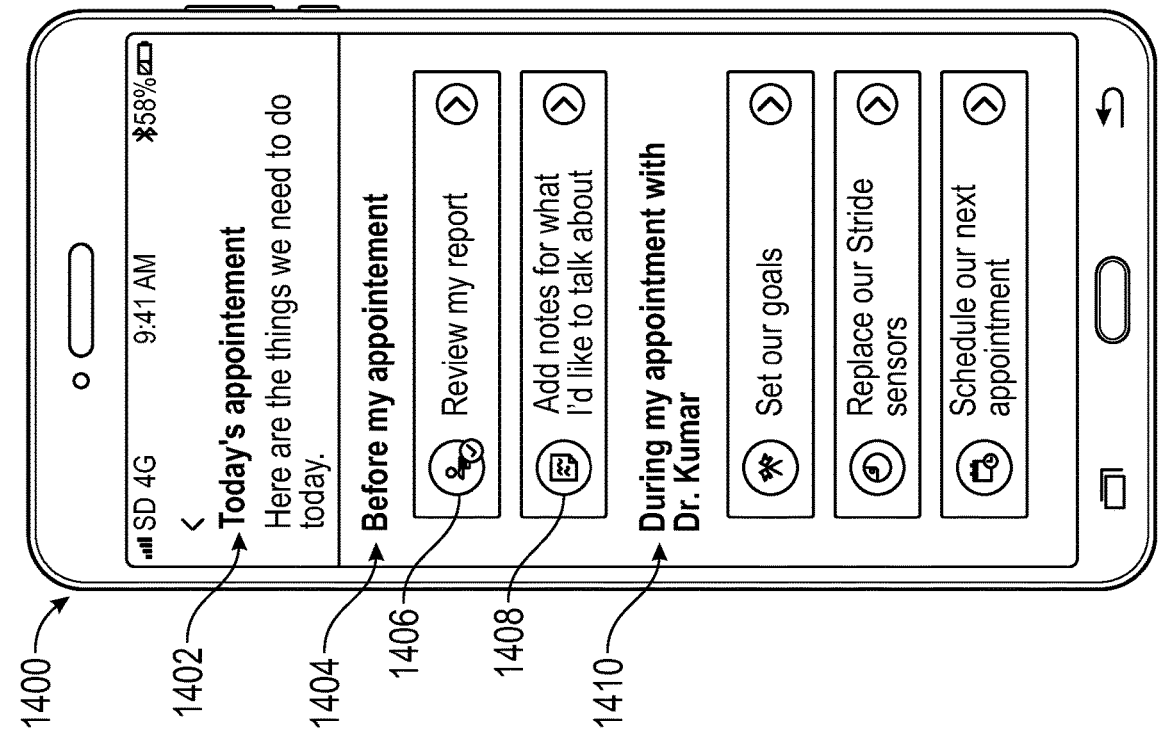
FIG. 9C illustrates an example appointment interface presentable in the computing environment of FIG. 3.
Figure 9B:
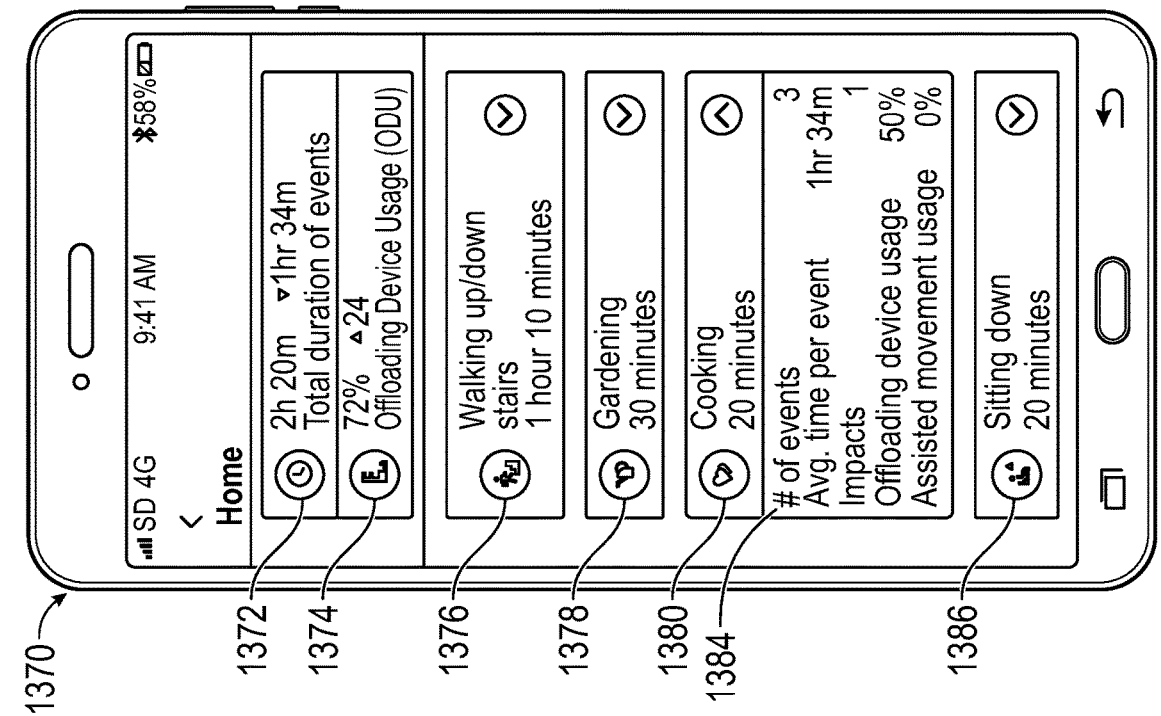
FIG. 9B illustrates an example home interface presentable in the computing environment of FIG. 3.

FIG. 9B illustrates a home interface 1370 that can include an interface identifier (for example, "Home") and present the user with data or information regarding the activities that occurred when the user was determined or identified to have been at his or her home. The home interface 1370 can present the user with a cumulative home event time 1372 and an offloading percentage usage 1374 for events that occurred while the user spent at home. The home interface 1370 can present the user with an amount of time that the user was engaged in particular activities while at home and during which events occurred. Such activities can correspond with activities, including walking up/down stairs 1376, gardening 1378, cooking 1380, or sitting down 1386 that were input or selected by the user, such as during the activity identification process 500.

The home interface 1370 can present an activity type summary 1384 that presents the user with information regarding the home events for a particular type of activity, such as cooking. The activity type summary 1384 can indicate the number of events that the user was engaged in during the home time, the average time the user spent per event, the number of impacts or trauma events that occurred during the home time, the percentage of time the user used the offloading device during the home time, and the percentage of time that the user was assisted during movement.

FIG. 9C illustrates an appointment interface 1400 that can present the user with a schedule of one day's (such as today's) appointments, as well as details and tasks related thereto. An instructional message 1402 that can state "Today's appointments" and other descriptive text or symbols can be included on an upper portion of the appointment interface 1400. The appointment interface 1400 can include a pre-appointment checklist 1404, which can present the user with tasks to be completed before the appointment, and an appointment activities checklist 1410, which include a name of the doctor for an upcoming appointment and other preparation options. A first task element 1406 can present the user with an option to select and review the first task. In the illustrated example, the first task can be to "review my report." Accordingly, selecting the first task element 1406 can transition the user application 312 from the appointment interface 1400 to another user interface that presents the user with a relevant report related to a doctor visit. A second task element 1408 can, upon selection by the user, transition the user application 312 from the appointment interface 1400 to another user interface in which the user can input questions, issues, reminders, or other information related to the appointment for which the user wishes to prepare. The appointment activities checklist 1410 can present the user with an ability to set goals, replace sensors (such as the activity monitoring device 120 or the offloading monitoring device 132 associated with the user application 312), or schedule a next appointment with a clinician.

Figure 9D:
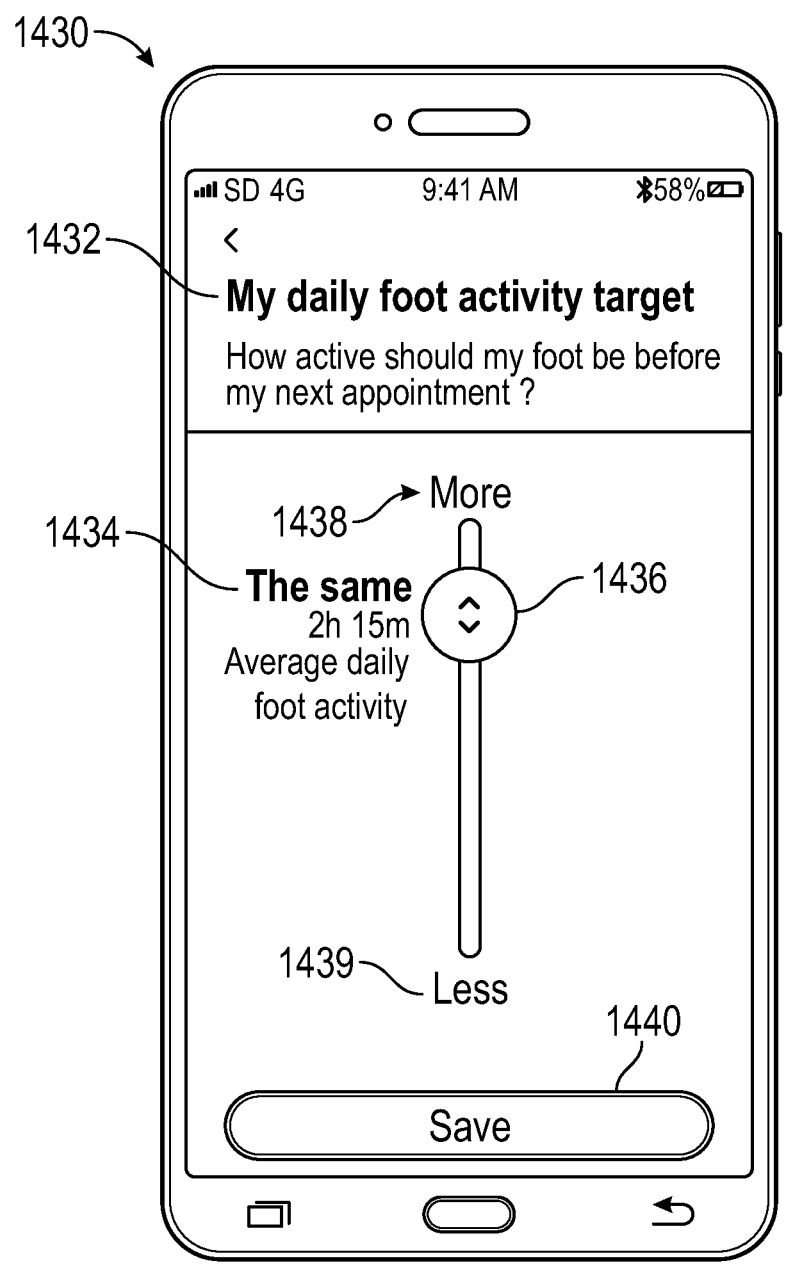
FIG. 9D illustrates an example foot activity target interface presentable in the computing environment of FIG. 3.

FIG. 9D illustrates a foot activity target interface 1430 that can present the user with an informational message 1432, which can include the title of the foot activity target interface 1430 (which can be "My daily foot activity target") and a description of the requested information to be input or adjusted on the foot activity target interface 1430. As illustrated, the requested information can be "How active should my foot be before my next appointment?" The foot activity target interface 1400 can enable the user to input an average target foot activity 1434, such as daily activity, over a length of time (for example, since the last doctor visit) and a slider element 1436 that may be maintained in a corresponding position, which can be moved up for a higher target (for example, toward more 1438), or moved down for a lower target (for example, toward less 1439). The foot activity target interface 1430 can have a save element 1440, the selection of which by the user can trigger a transition by the user application 312 to a different or subsequent user interface.

FIGS. 10A-10E illustrate example user interfaces that can be presented by the user application 312 on the user interface 316 of the user operation device 310 to encourage interactions by the user with the user application 312 and the input of requested information to the user application 312. The user interfaces of FIGS. 10A-10E or aspects thereof can be adjusted, as described herein, responsive to an engagement by the user with the user application 312, such as described with respect to block 650 of FIG. 6.

Figure 10B:
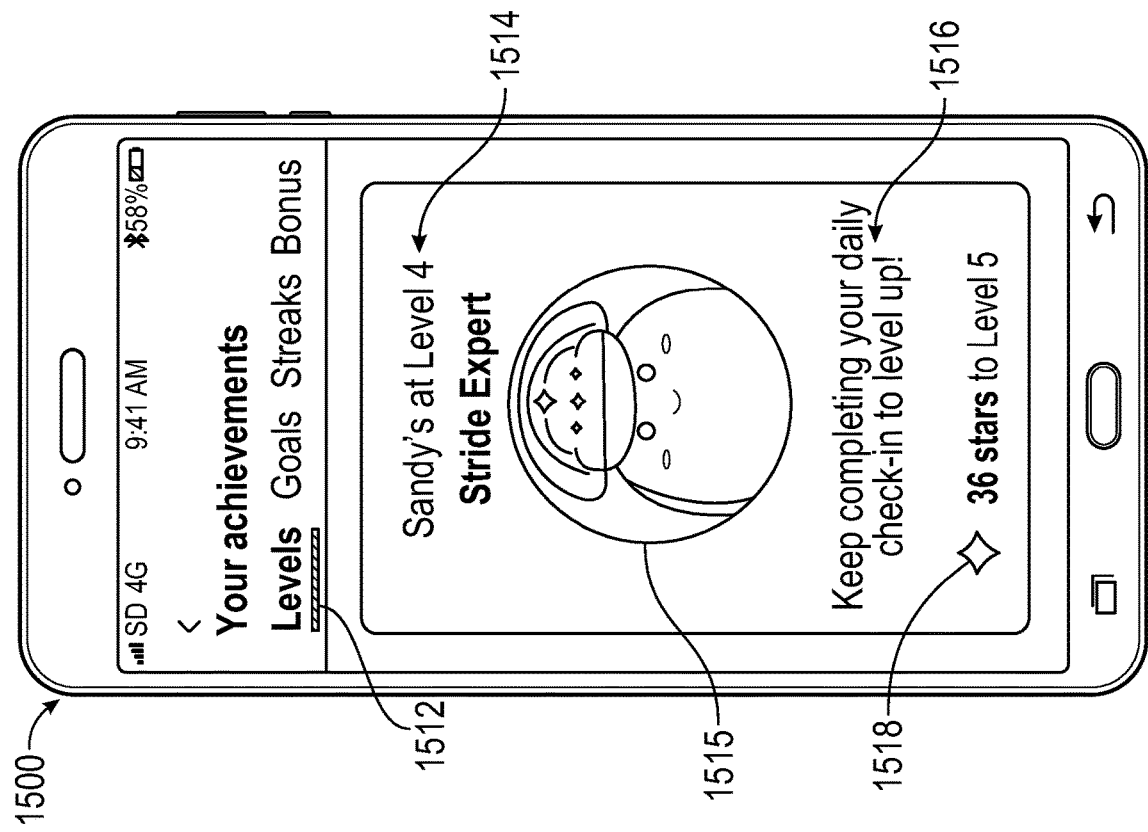
Figure 10A:
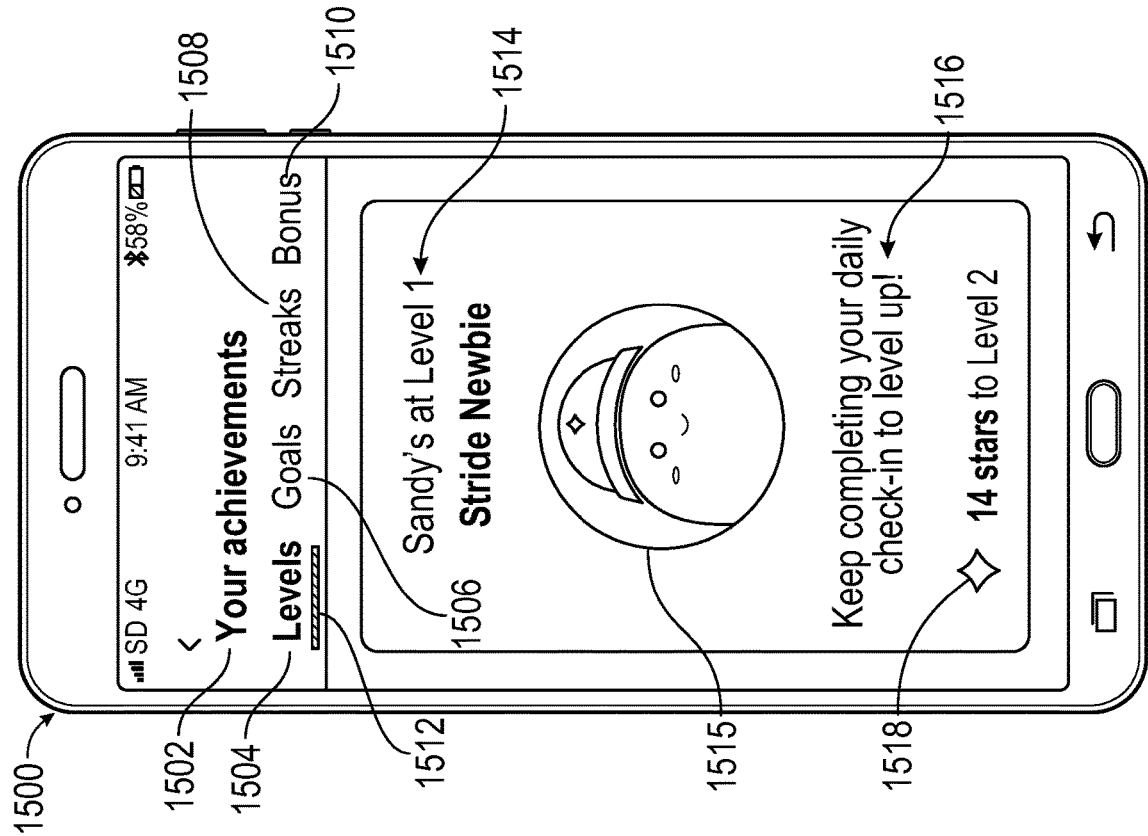

FIG. 10A illustrates an achievement summary interface 1500 that can present the user with a summary of achievements to date. The achievement summary interface 1500 can include an achievements summary table 1502 configured to present summary information regarding aspects of the user's achievements with the user application 312. The achievements summary table 1502 can present a levels element 1504, a goals element 1506, the streaks element 1508, and a bonus element 1510. Upon selection by the user of the levels element 1504, the achievement summary interface 1500 can transition to presenting the user with an assigned level 1514 that has been achieved based on the user's compliance or engagement with the user application 312. An underscore 1512 can indicate to the user which selectable table element has been selected and is being presented, and the unselected table elements can be shown in a lighter color, such as gray, while the selected table element can be shown in a brighter color, such as blue.

The levels can range, for example, from 1 to 5 and may include level 1 Newbie (shown in FIG. 10A), level 2 Novice (not shown), level 3 Pro (not shown), level 4 Expert (shown in FIG. 10B), and level 5 Master (not shown). Each of these different levels can have a present a character 1515, which may be the same character selected via the character select interface 1070 by the user, with different accessories or facial expressions to illustrate or represent the level that the character 1515 has achieved. The level of happiness expressed in the facial expressions of the character 1515 can increase with each increasing level from Newbie to Master.

The level assigned to the user may depend on a number of tokens (sometimes described herein as stars) that the user has accumulated through compliance or engagement with the user application 312. A token may be awarded each time a user completes a check-in or completes another task. Increases in the assigned level or number of tokens may result in visual changes in the graphical user interfaces presented on the user interface 316 to the user (for example, different formatting, color schemes, presentation of textual information). A token level indicator 1518 can present to the user the number of tokens that the user has accumulated and may accordingly allow the user to understand the number of stars to accumulate to achieve a next level. The achievement summary interface 1500 can include an instructional message 1516 instructing the user on how to achieve more stars and advance to the next level and may provide a count of tokens to advance to the next level.

Upon selection by the user of the goals element 1506, as indicated by the underscore 1512 in FIG. 10C, the achievement summary interface 1500 can transition to present the user with his or her goal-based achievements based on the user's successful completion of goals, as shown in FIG. 10C. Examples of goal-based achievements can include New Leaf 1530, Goalsetter 1532, Habit Hero 1534, Fearless Focus 1536, Plate Spinner 1538, and Multitasker 1540. Each of the different goal-based achievements can be achieved when the user has completed certain criteria associate with the goals. For example, New Leaf 1530 can be achieved when the user has completed three of his or her goals. Goalsetter 1532 can be achieved when a user has completed ten of his or her goals. The achievement summary interface 1500 can present a flag or checkmark symbol to indicate the goals that have been achieved by the user. Upon selecting a goal-based achievement, the achievement summary interface 1500 can present the user with information about achievement of the associated goal. The achievement summary interface 1500 can indicate the goals that have not yet been achieved by showing a padlock symbol positioned proximate to the unachieved goals. The achievements summary interface 1500 can present a progress ring 1541 which fills to indicate the user's progress in achieving a respective goal. As the progress ring 1541 fills, the progress ring denotes greater progress toward achieving the respective goal.

Upon selection by the user of the streaks element 1508, as indicated by the underscore 1512 in FIG. 10D, the achievement summary interface 1500 can transition to present the user with streak based achievement awards based on a consecutive number of days that a user has completed one or more activities or the checked-in process. If the user has completed one or more activities for seven consecutive days, the achievement summary interface 1500 can present the user with a 14 days activity achievement award 1544 for this achievement. Another achievement for activities can be presented for a 14 days activity achievement award 1548, a 21 days activity achievement award 1552, or a more than 21 days activity achievement award (not shown).

If a user has completed check-ins for seven consecutive days, the achievement summary interface 1500 can present the user with a 7 days check-in achievement award 1546 for this achievement. A 14 days check-in achievement award 1550 and a 21 days check-in achievement award 1554 can similarly be presented for a greater number of consecutive days of check-ins. The achievement summary interface 1500 can present a picture and checkmark symbol to indicate the streak achievement that has been achieved by the user. The achievement summary interface 1500 can indicate the streak achievement that have not yet been achieved by showing a padlock symbol for each of the unachieved achievements. The achievements summary interface 1500 can present a progress ring 1555 to indicate the user's progress in achieving the streak achievements.

Figure 10E:
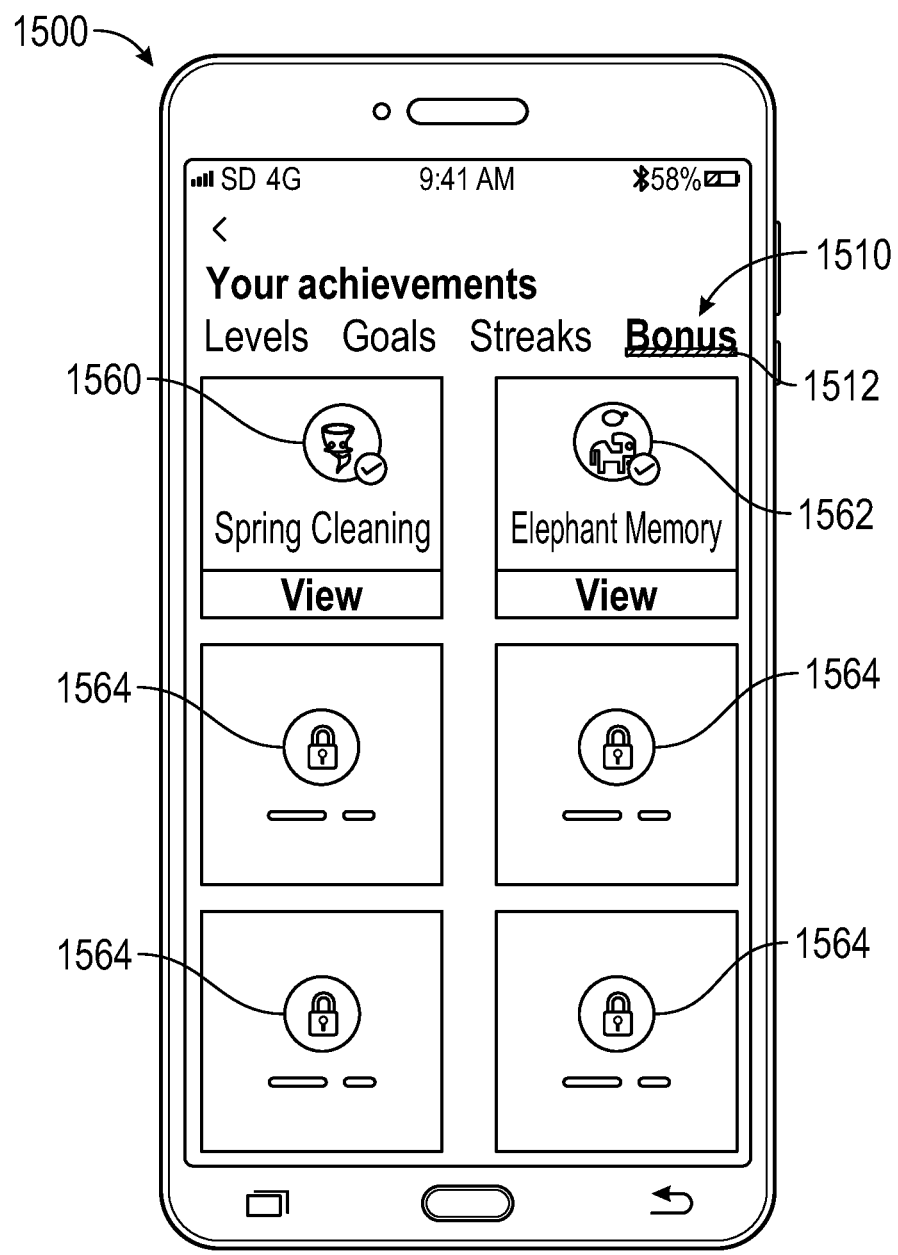

Upon selection by the user of the bonus element 1510, as indicated by the underscore 1512 in FIG. 10E, the achievement summary interface 1500 can transition to present the user with earned bonus achievements. Bonus achievements can be presented to the user when the user has achieved a threshold number of the following actions (for instance, cumulatively): achieving multiple goals in one day, editing multiple events previously identified as "I don't remember", tagging events from 2 or more days prior, viewing multiple journal entries, adding multiple talking points for clinician appointments, or having checked-in and stayed within activity target level for a set number of days. Bonus achievements that can be presented include Spring Cleaning 1560, Elephant Memory 1562, or others. Locked bonus achievements 1564 can be presented to indicate bonus achievements that are not yet achieved or viewable.

Figure 11A:
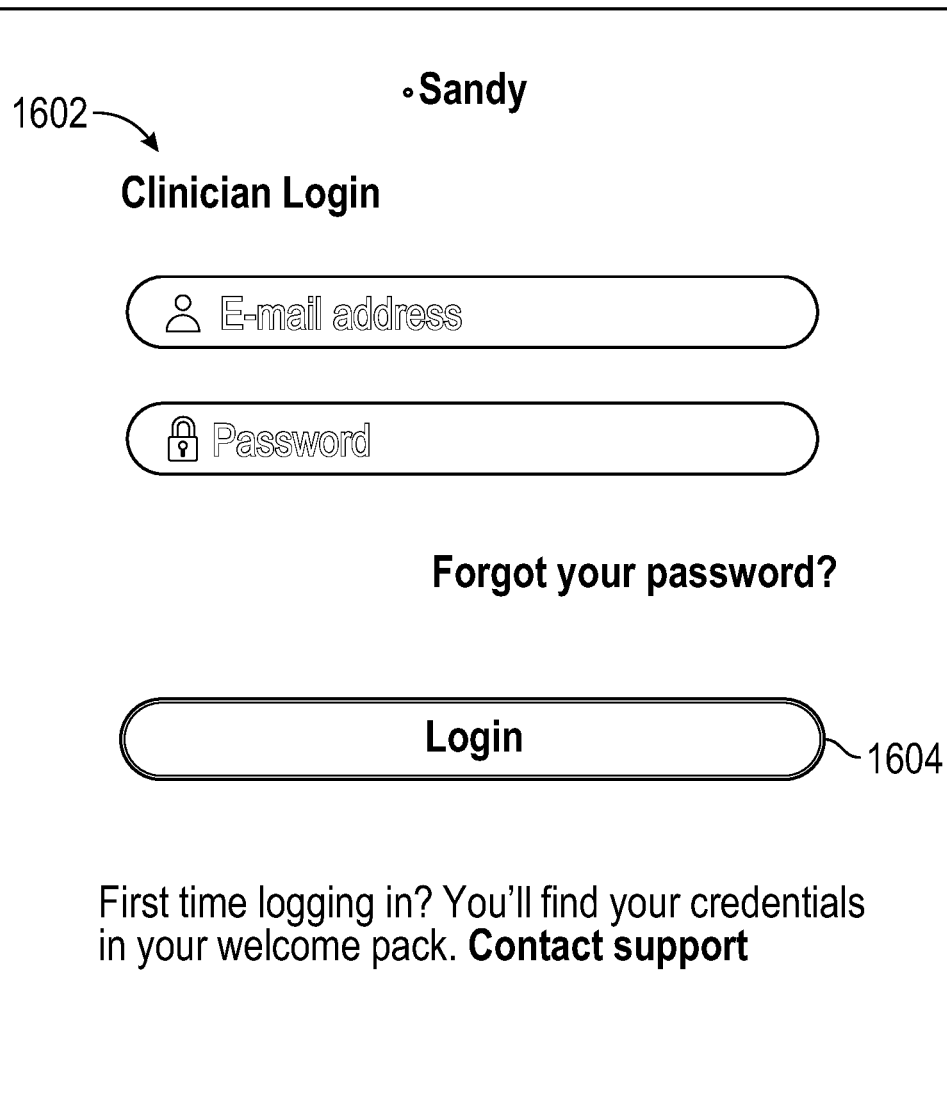
FIG. 11A illustrates an example clinician login interface presentable in the computing environment of FIG. 3.
Figure 11B:
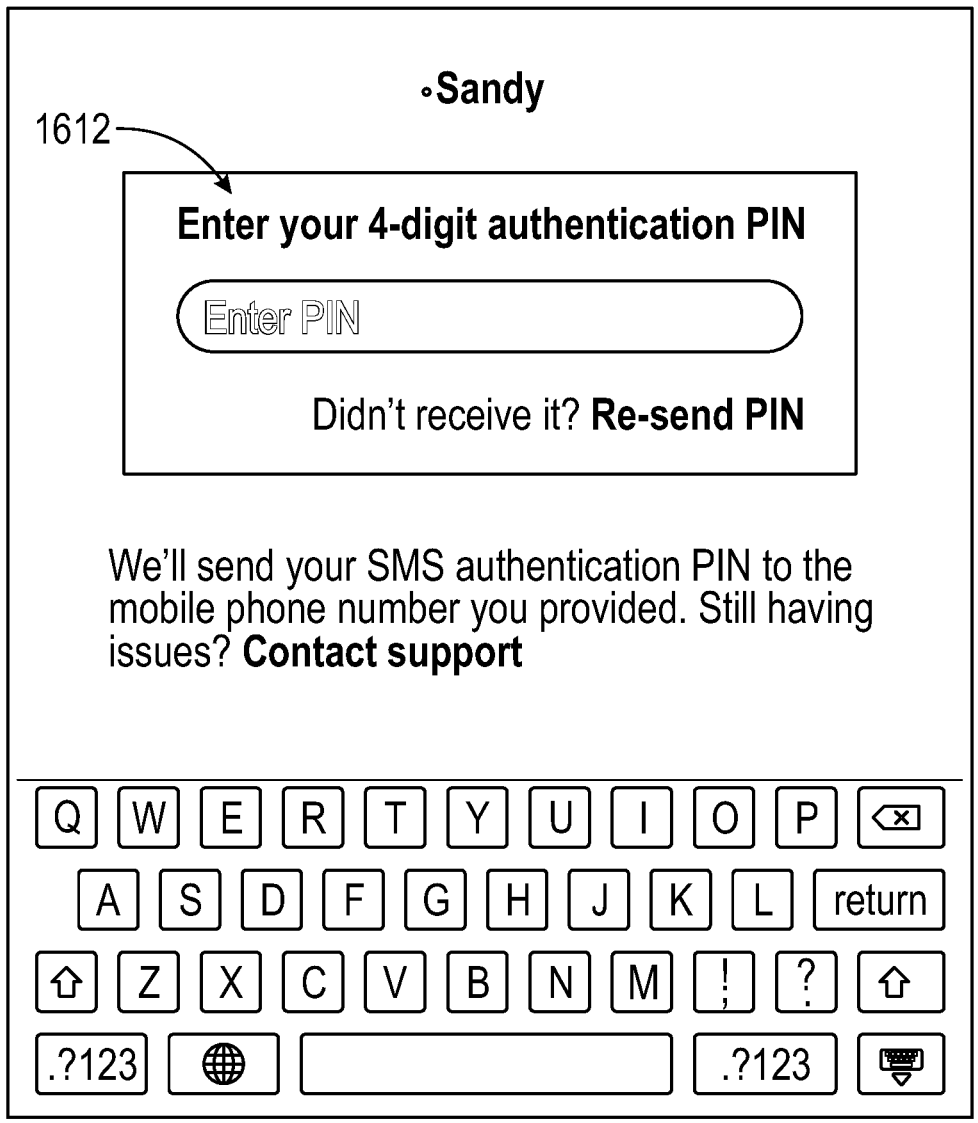
FIG. 11B illustrates an example authentication interface presentable in the computing environment of FIG. 3.

FIGS. 11A and 11B illustrate example user interfaces that can be presented by the clinician application 322 to permit a clinician to initiate access to information for the users which the clinician may be assisting. The information may have been gathered or determined by the device management system 340 through the user operation device 310, as well as the activity monitoring device 120 or the offloading monitoring device 132. A clinician login interface 1600 can present a login prompt 1602 requesting an email address or account name, as well as a password. Upon selection of the login element 1604, the clinician application 322 can transition from the clinician login interface 1600 to an authentication interface 1610. The authentication interface 1610 can present an authentication request 1612 for an authentication PIN, which may be provided to the clinician via out-of-band communication, such as through a text message like a short message service message (SMS) over a cellular network.

FIGS. 12A-12G illustrate example user interfaces that can be presented by the clinician application 322 to allow a clinician to review information for the users which the clinician may be assisting. As described with respect to FIGS. 11A and 11B, the information may have been gathered or determined by the device management system 340 through the user operation device 310, as well as the activity monitoring device 120 or the offloading monitoring device 132

Figure 12A:
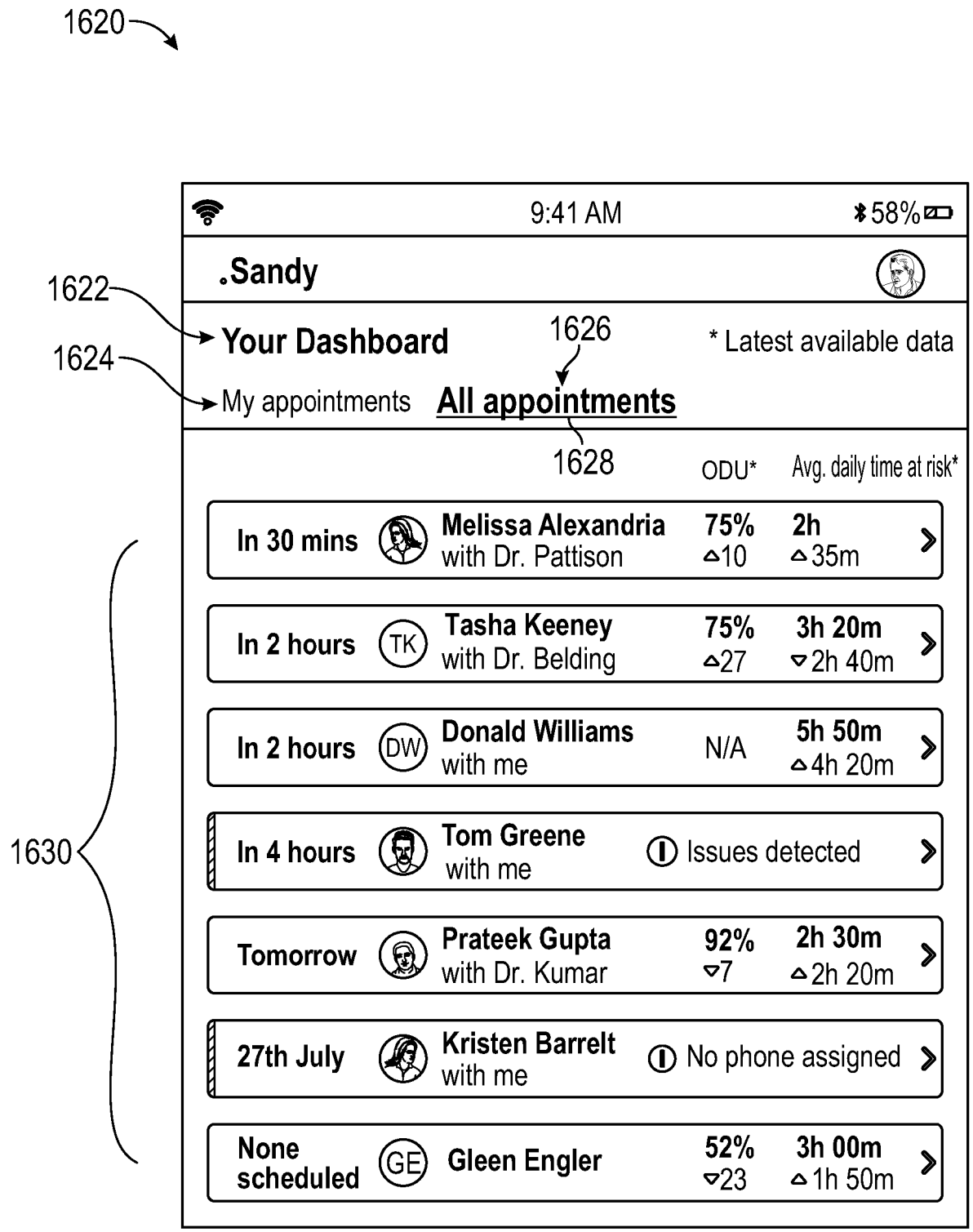
FIG. 12A illustrates an example dashboard interface presentable in the computing environment of FIG. 3.

FIG. 12A illustrates a dashboard interface 1620, which may present a dashboard heading 1622, a my appointments element 1624, and an all appointments element 1626. An underscore 1628 can indicate to the clinician which appointments element has been selected and is being presented. The dashboard interface 1620 can provide an appointment list 1630 of the appointments with users in chronological order for a period of time. The appointment list 1630 can identify a time when an appointment with a user will start, a name of the user, a name of the clinician, and a summary of other metrics that may be relevant to the user, and a brief summary of the user's activities or progress during a period of time, including an offloading device usage (ODU) and an average daily time at risk for each user. The appointment list 1630 can present the information for each user appointment on a selectable element that, upon selection by the clinician, can transition the clinician application 322 from the dashboard interface 1620 to an individual user interface 1640 shown in FIG. 12B that has additional information and details regarding the patient that was selected.

Figure 12B:
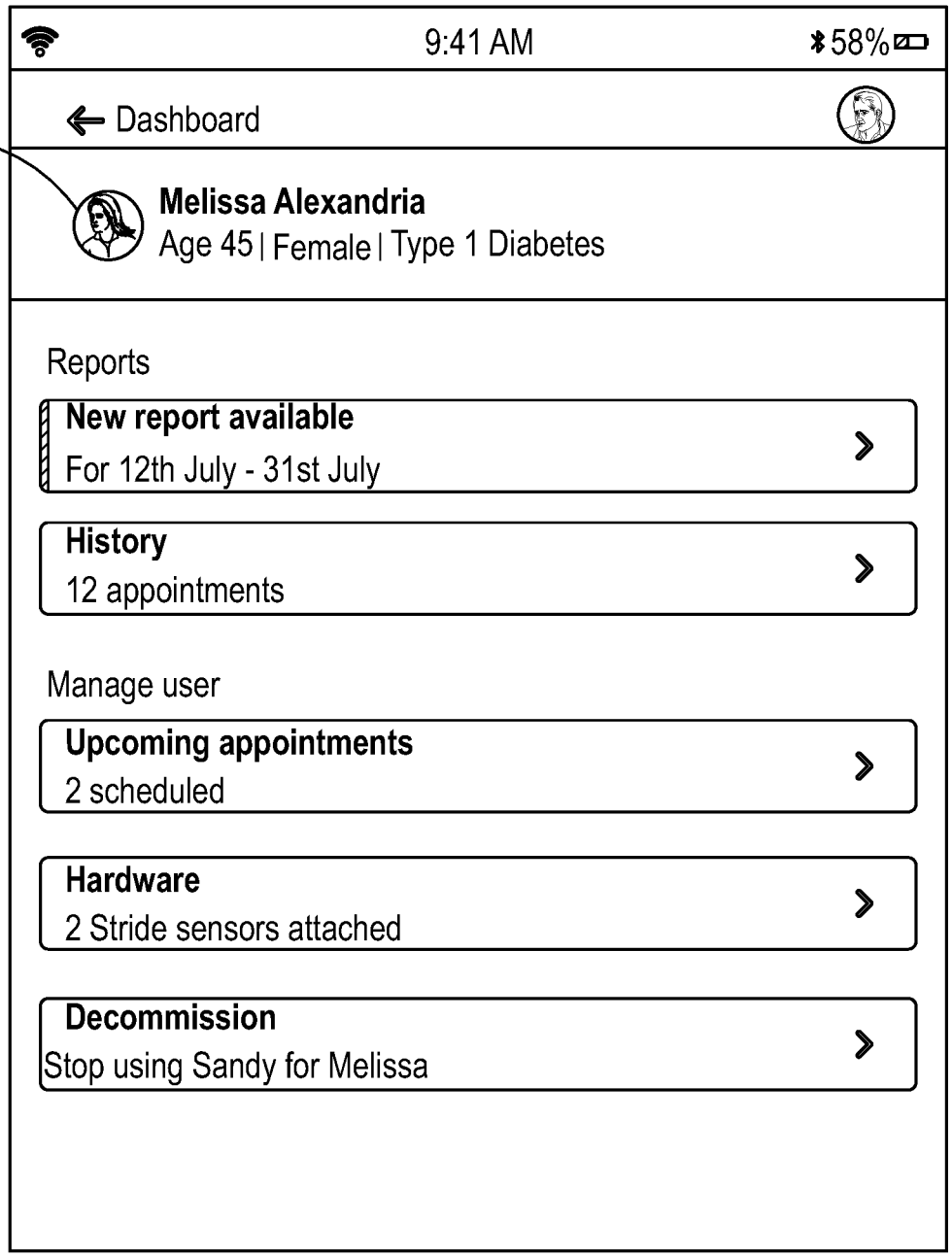
FIG. 12B illustrates an example individual user interface presentable in the computing environment of FIG. 3.

With reference to FIG. 12B, the individual user interface 1640 can present a user identifier 1642 that can include the user's name, picture, age, gender, or other medical conditions for the user. The individual user interface 1640 can present a report menu 1644 that can include summary information regarding available reports and a history of appointments for the user. Upon selection by the clinician of any of the selectable elements within the report table, the clinician application 322 can transition from the individual user interface 1640 to another user-related interface that can, for example, present a detailed report of the user or a history of the user, including an appointment history. The individual user interface 1640 can present a user management menu 1645 (which may be referred to as a manage user menu) that, upon selection by the clinician, can transition the clinician application 322 from the individual user interface 1640 to a manage appointments interface, a manage hardware interface, or a decommission application interface.

Figure 12C:
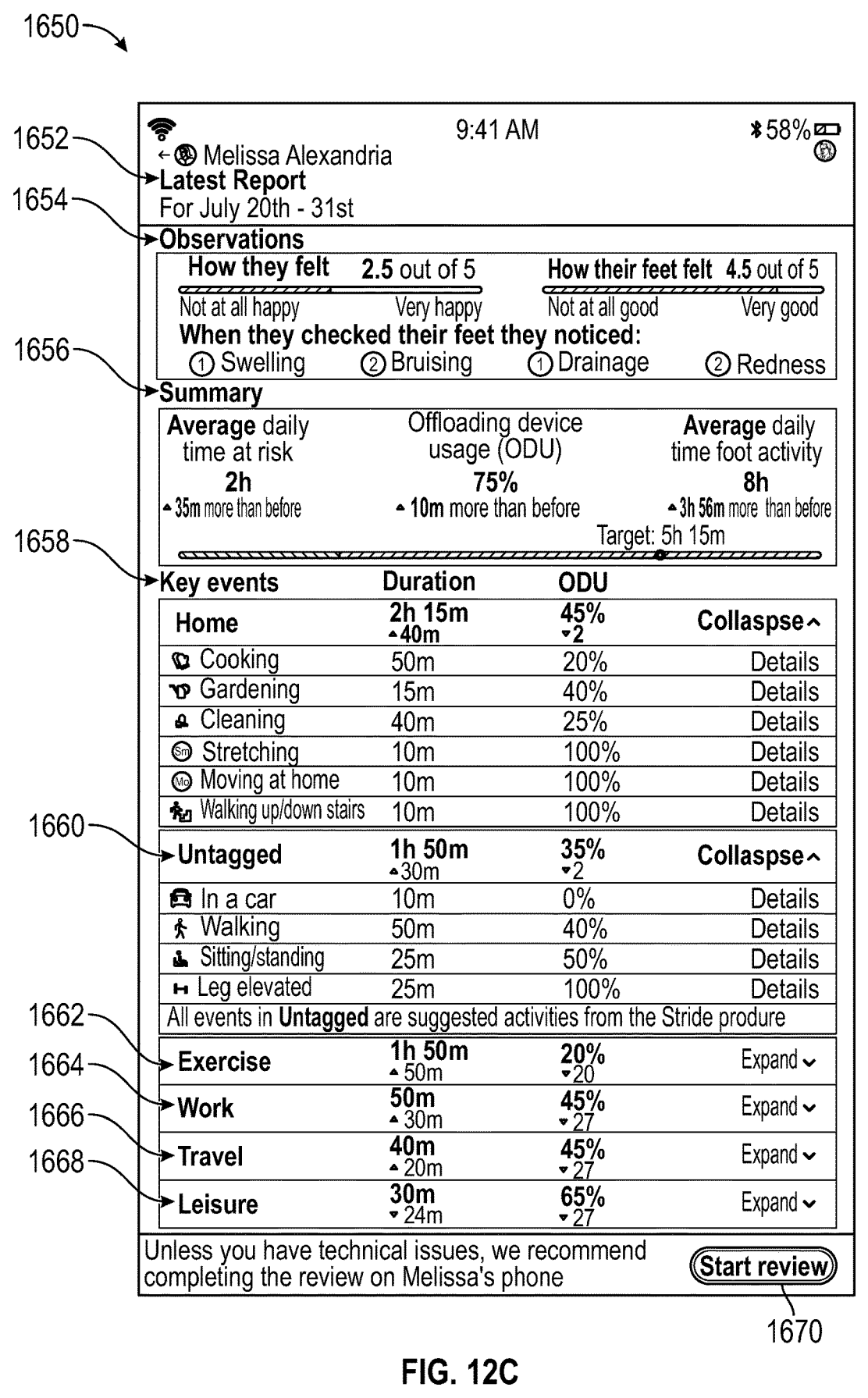

Upon selection of the new report available element of the report menu 1644, the clinician application 322 can transition from the individual user interface 1640 to an individual user interface 1650 (as shown in FIG. 12C) that can present a report identifier 1652, an observations table 1654, a summary table 1656, a key events table 1658, an untagged table 1660, an exercise activity summary 1662, a work activity summary 1664, a travel activity summary 1666, and a leisure activity summary 1668. The observations table 1654 can present to the clinician a summary of how the user felt, how the user's foot felt, or symptoms observed by the user regarding his or her feet during a period of time. The summary table 1656 can present to the clinician an average daily time at risk, an offloading device usage, or an average daily time that the foot was active, such as is described with respect to FIG. 9A. For example, the summary table 1656 can include (i) a time the foot was loaded (or active), which can reflect the amount of time the user has engaged in activity that loaded the foot (such as, any activity other than laying down or sitting/standing up with the foot lifted) and (ii) an amount of time from the time the foot was loaded that the user wore the offloading device (which can be expressed as a percentage or ratio). Any of these times can be expressed as a daily time or average daily time (or another time period). The summary table 1656 can include a time the foot has been at risk, which can be determined as the difference between the time the foot was loaded and the amount of time the user wore the offloading device. The summary table 1656 can include information (for example, in form of a line graph or another user interface element) that visually illustrates a time the foot was loaded (illustrated as a line segment on the left side), a time the foot has been at risk (illustrated as the entire line segment), and a target amount of time for wearing the offloading device (illustrated as a dot). These three metrics, alone or in combination with the visual illustration, can allow the clinician to quickly and reliably analyze the user's lifestyle, determine a user's compliance with wearing the offloading device, a healing trajectory, or a risk of exacerbating an existing ulcer or developing a new ulcer, or make appropriate adjustments to therapy.

The key events table 1658 can present the clinician with information regarding the activities engaged in by the user and the duration of such activities. The category or type of activity may be presented in the key events table in a selectable format wherein, upon selection of a particular key event category, the clinician application 322 can transition from the individual user interface 1650 to a detailed key event report interface showing more details regarding the selected key event, such as described with respect to FIG. 12D. The untagged table 1660 can present information regarding untagged events, which may be been assigned by the data processing system 344 with likely activities engaged in by the user at the time of the untagged activities. The untagged activities can include, for example, time spent in a car (such as driving), time spent walking, time spent sitting or standing, or time spent with the leg elevated. A transition element 1670 can transition the clinician application 322 from the individual user interface 1650 to a subsequent interface.

Figure 12D:
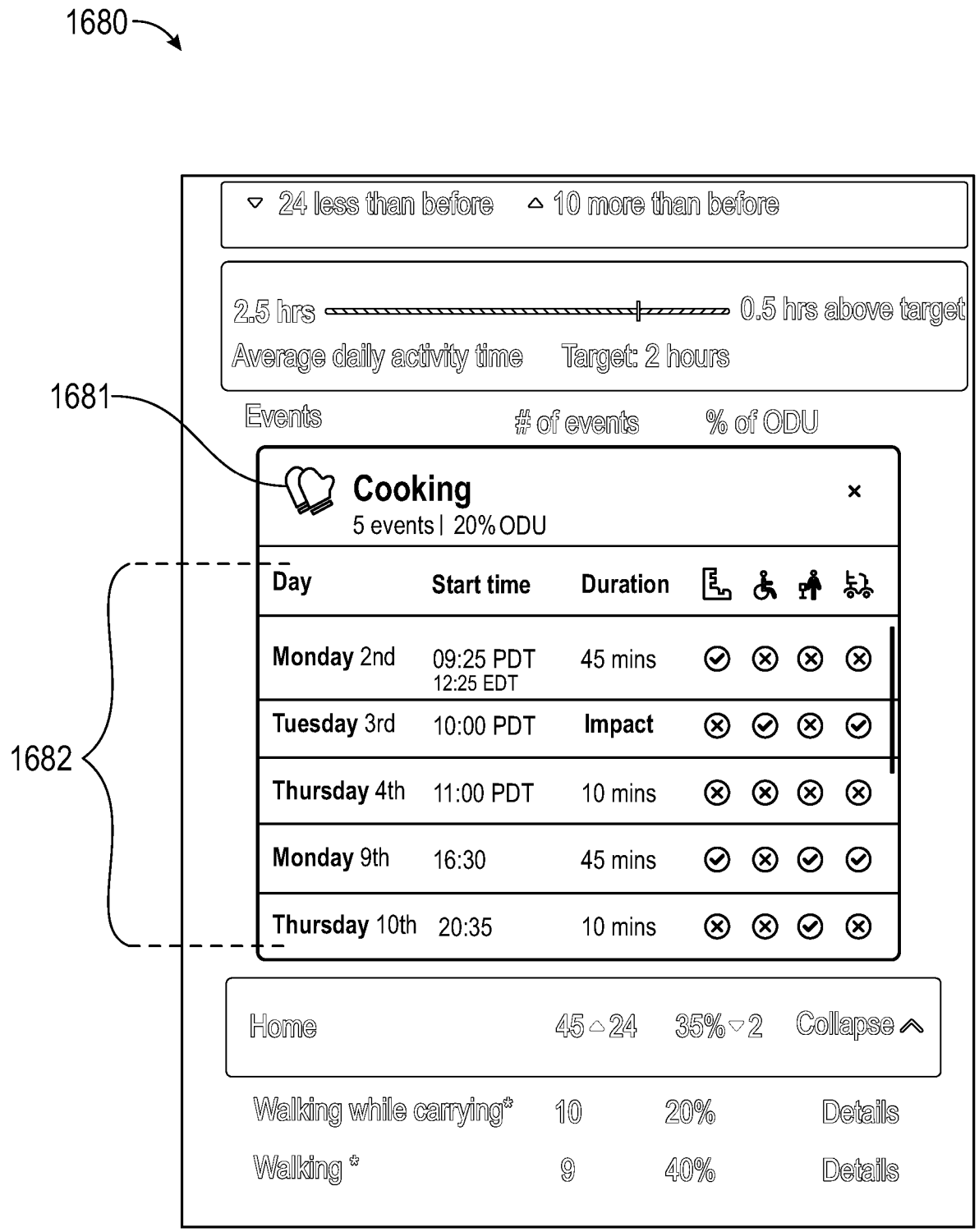
FIG. 12D illustrates an example cooking report interface presentable in the computing environment of FIG. 3.

FIG. 12D illustrates a cooking report interface 1680, which is an example of a detailed key event report for cooking. The cooking report interface 1680 can include information about cooking events, including a summary 1681 presenting the name of the respective key event category (such as, "Cooking"), number of cooking event occurrences, and the percentage of offloading device usage during the cooking events. The cooking report interface 1680 can present a detailed event report 1682 that can show the day of the week of each event, the start time and duration of each event, whether an impact (which can be a quick strike to the limb of a user) occurred during the respective cooking event, and the type of assisted movement used, if any, during the event. Similar report interfaces can be available for other activities.

Figure 12E:
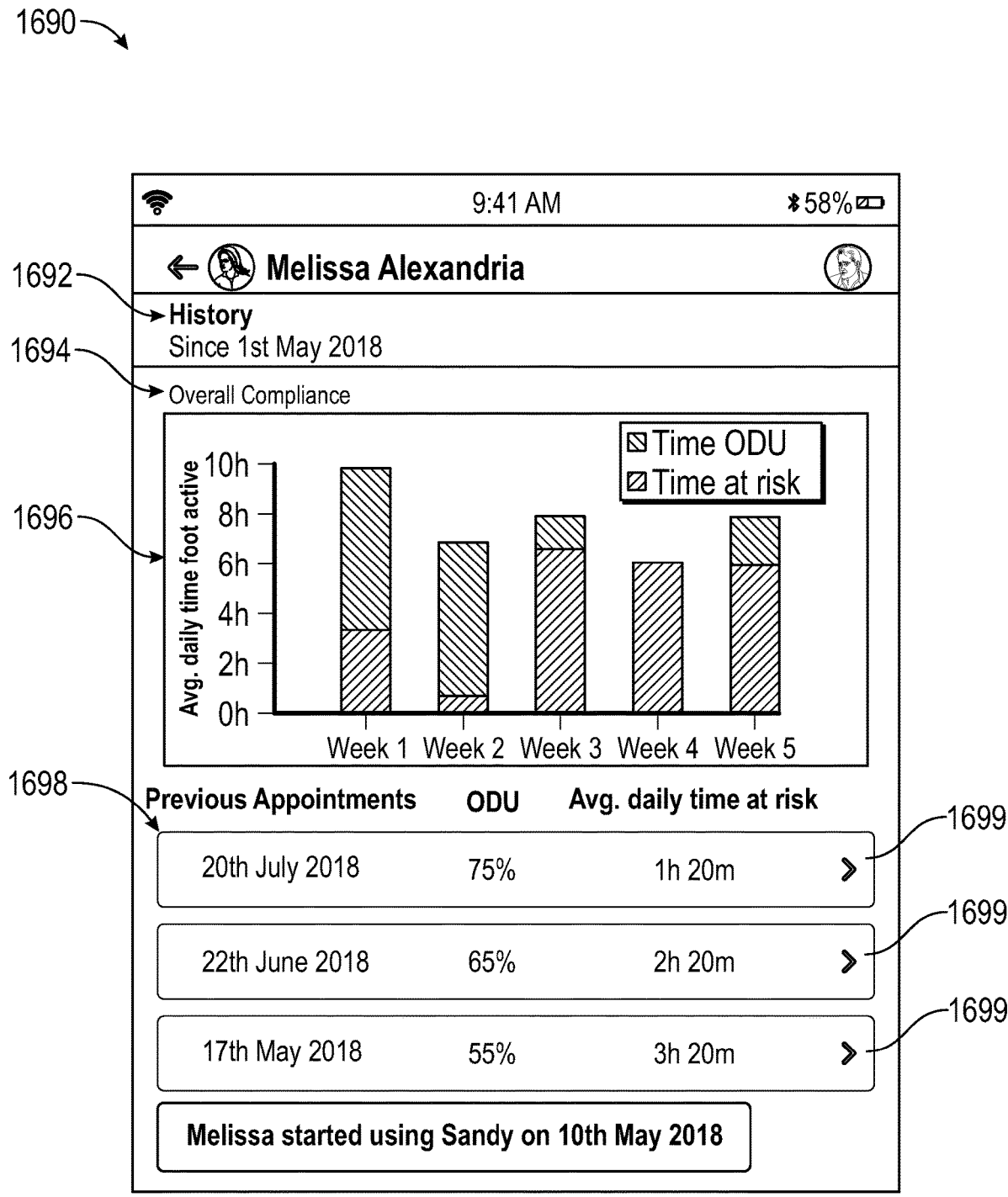
FIG. 12E illustrates an example individual user interface presentable in the computing environment of FIG. 3.
Figure 12F:
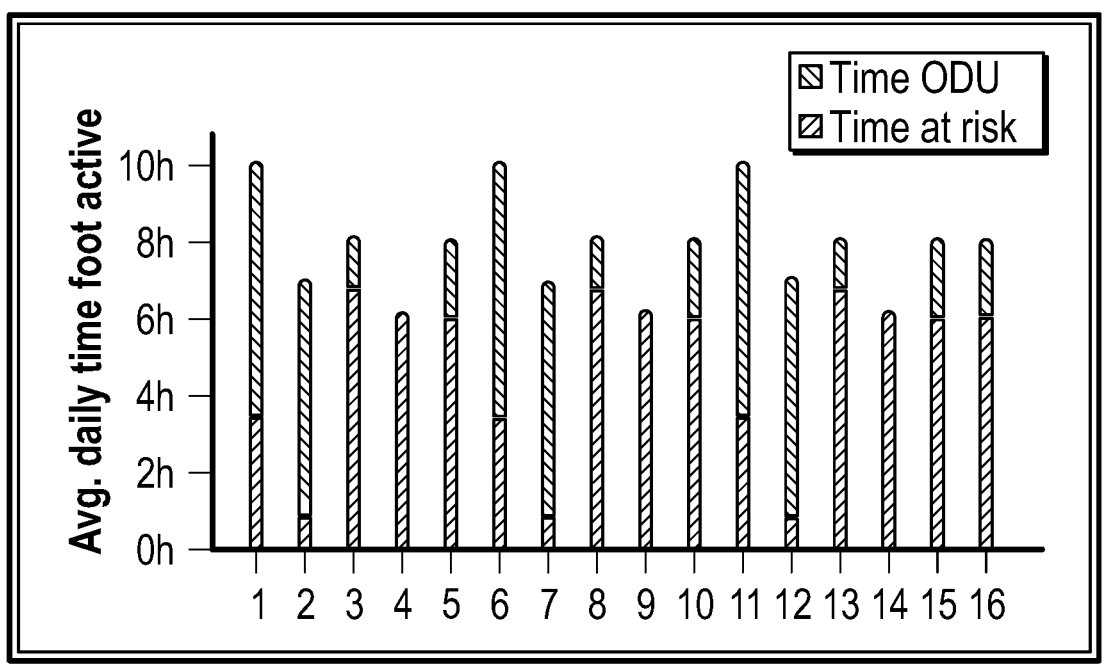
FIG. 12F illustrates an example daily bar graph summary presentable in the computing environment of FIG. 3.

FIG. 12E illustrates a user history interface 1690 that can present an informational message 1692 including the date range of the history report presented on the user history interface 1690, an overall compliance table 1694, and an appointment history table 1698. The overall compliance table 1694 can present a bar graph summary 1696 that presents the ODU time and time at risk, such as on a weekly basis during the report duration. The appointment history table 1698 can show the dates of previous appointments, the ODU during the time period before the appointment, and the average daily time at risk during the time period before the appointment. The appointment history table 1698 can have selectable appointment elements 1699 associated with each previous appointment that, upon selection by the clinician, can transition the clinician application 322 from the user history interface 1690 to a daily bar graph summary 1710 illustrated in FIG. 12F that can present the clinician with the ODU time and time at risk on a daily basis during the report duration. As described herein, this information can allow the clinician to quickly and reliably analyze the user's lifestyle, determine a user's compliance with wearing the offloading device, a healing trajectory, or a risk of exacerbating an existing ulcer or developing a new ulcer, or make appropriate adjustments to therapy.

Figure 12G:
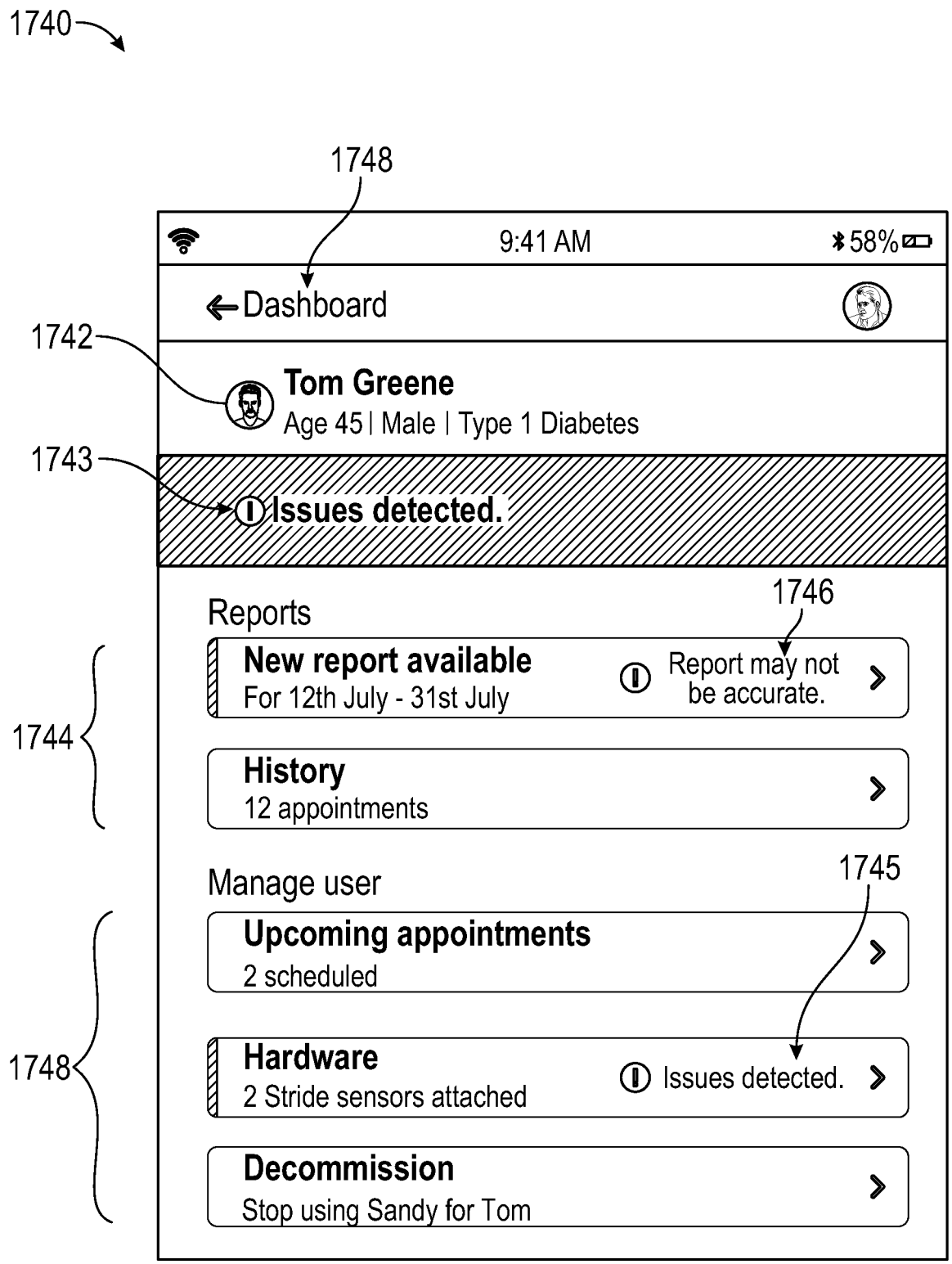
FIG. 12G illustrates another example individual user interface presentable in the computing environment of FIG. 3.

FIG. 12G illustrates another individual user interface 1740 similar to the individual user interface 1650, but which presents error information for the user. A user identifier 1742 on the individual user interface 1740 that can include the user's name, picture, age, gender, or other medical conditions. The individual user interface 1740 can present a report menu 1744 that can present summary information regarding reports that are available and history of appointments for the user. The report menu 1744 can present a report status indicator 1746 that can alert the clinician that one or more reports may be inaccurate or incomplete. Upon selection by the clinician of any of the selectable elements within the report menu 1744, the clinician application can transition from the individual user interface 1740 to another user-related interface. The individual user interface 1740 can present a user management menu 1748 that, upon selection by the clinician, can cause presentation of a manage appointments interface, a manage hardware interface, or a decommission application interface. The individual user interface 1740 can include a first warning indicator 1743 and a second warning indicator 1745 that can alert the clinician that issues were detected in the hardware components of the activity monitoring device 120 or the offloading monitoring device 132.

Any of the features, components, images, designs, or other details of any of the user interfaces or aspects of user interfaces shown or described herein can additionally or alternatively be included in any of the other user interfaces or aspects of user interfaces shown or described herein to form additional user interfaces.

The user interfaces shown and described herein can include one or more interface controls that may be selected, for example, using the user interface 316 of the user operation device 310 or the user interface 326 of the clinician operation device 320. The user interfaces may be output for presentation by the user application 312 of the user operation device 310 or the clinician application 322 of the clinician operation device 320. The user controls shown are merely illustrative examples and can be varied in other aspects. For instance, buttons, dropdown boxes, select boxes, text boxes, check boxes, slider controls, or other user interface controls may be substituted with other types of user interface controls that provide the same or similar functionality. Further, interface controls may be combined or divided into other sets of interface controls such that similar functionality or the same functionality may be provided with very different looking user interfaces. Moreover, each of the interface controls may be selected by a user using one or more input options, such as a mouse, touch screen input, or keyboard input, among other interface input options.

Computer System Components

Figure 13:
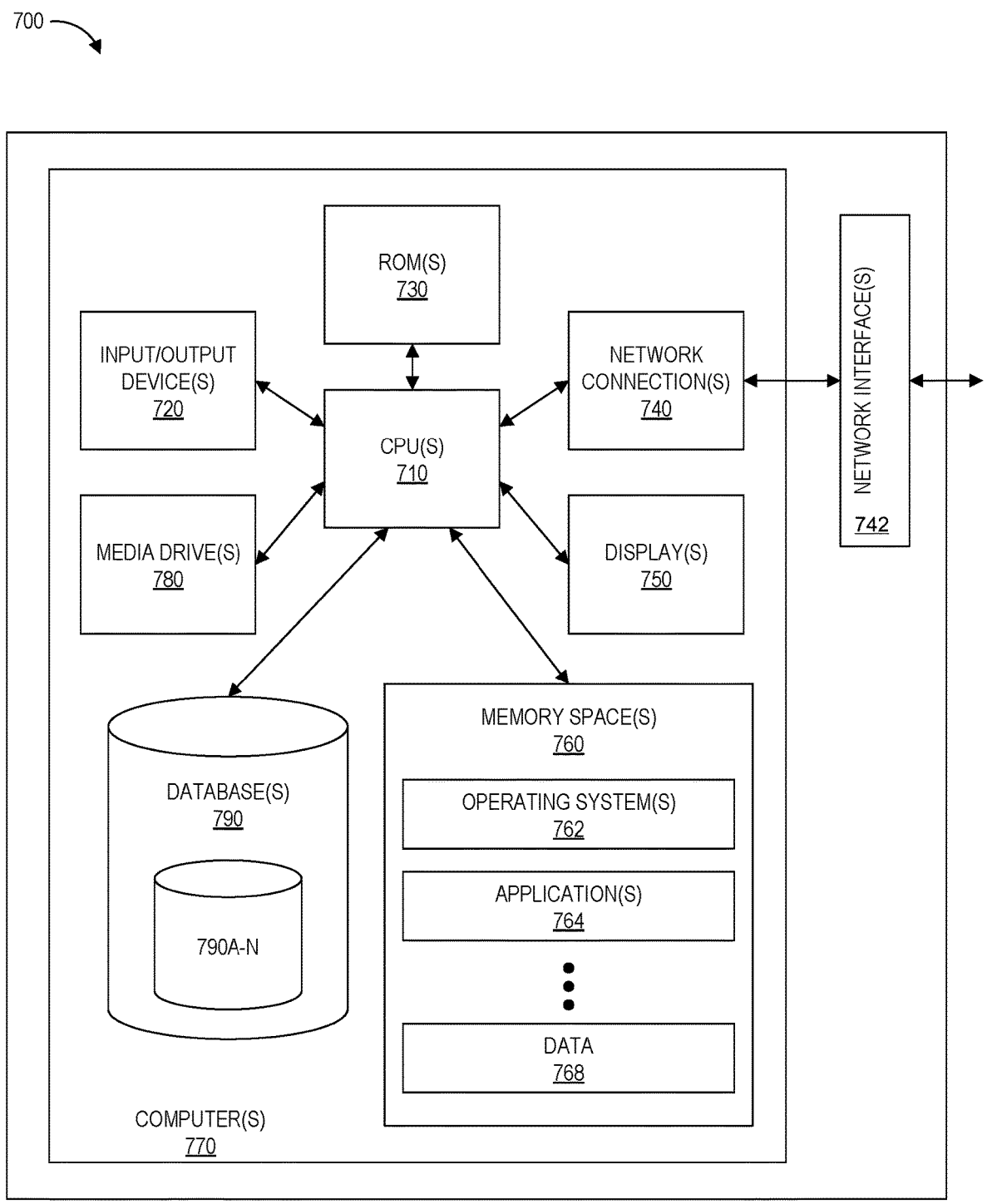
FIG. 13 illustrates an example computer system usable to construct one or more of the devices or systems within the computing environment of FIG. 3.

FIG. 13 illustrates a computer system 700 usable to construct one or more of the devices (for instance, the user operation device 310 or the clinician operation device 320), systems (for instance, the device management system 340), servers, or the like within the computing environment 300 of FIG. 3.

As shown in FIG. 13, the computer system 700 can include (i) a processor(s) (CPUs) 710, (ii) an input/output device(s) 720 configured to allow users to input and output information and interact with the computer system 700 as well as transfer and receive data or capture data with one or more sensors like an image sensor, (iii) a read only memory device(s) (ROMs) 730 or equivalents to provide nonvolatile storage of data or programs, (iv) a display(s) 750 such as a computer monitor or other display device, (v) a network connection(s) 740 and a network interface(s) 742 configured to allow the computer system 700 to connect to other systems, servers, or portable devices, as well as a memory space(s) 760 and a database(s) 790. The database(s) 790 may be further divided or distributed as sub-database(s) 790A-790N, with the sub-database(s) storing feature or function specific information associated with a particular feature or function. The various components shown in FIG. 13 may be incorporated in a computer(s) 770. It is noted that the various components shown in FIG. 13, including the database(s) 790, are typically included as part of the computer(s) 770, however, they may be external to the computer(s) 770 in some embodiments. For example, the database(s) 790 may be external to the computer(s) 770 and may be part of a separate database computer system or networked database system. In some instances, the computer system 700 may be a computing device like a desktop computer, mobile phone, or a server.

The memory space(s) 760 may include DRAM, SRAM, FLASH, hard disk drives, or other memory storage devices, such as a media drive(s) 780, configured to store an operating system(s) 762, an application program(s) 764, and data 768, and the memory space(s) 760 may be shared with, distributed with or overlap with the memory storage capacity of the database(s) 790. In some embodiments, the memory space(s) 760 may include the database(s) 790 or in some embodiments the database(s) 790 may include the data 768 as shown in the memory space(s) 760. The data stored in the memory space(s) 760 or the database(s) 790 may include information, such as motion data, pairing program information, data processing routines, or other types of data described herein.

Other Variations and Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines or computing systems that can function together.

One or more user inputs described in this disclosure may be received using one or more different mechanisms. For example, user interface controls may be selected by a user using one or more input options, such as a mouse, touch screen input, or keyboard input, among other user interface input options. The user interface controls selected by the user can include one or more of buttons, dropdown boxes, select boxes, text boxes, check boxes, slider controls, or other user interface controls.

Although certain features are described in context of controlling of pairing, features of the disclosure can apply to control of communication permissions in types of system communications other than pairing.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, a microprocessor, a state machine, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A hardware processor can include electrical circuitry or digital logic circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain aspects include, while other aspects do not include, certain features, elements or states. Thus, such conditional language is not generally intended to imply that features, elements or states are in any way required for one or more aspects or that one or more aspects necessarily include logic for deciding, with or without author input or prompting, whether these features, elements or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A non-transitory computer readable medium having an application stored thereon that when executed by a processor of an electronic device causes the processor to perform a process for monitoring movement of a body part for assisting in treatment of the body part, the process comprising:
    receiving over a first computer network, by a communication interface, motion data from a motion sensor, the motion data being indicative of motion by a user while wearing the motion sensor;
    transmitting over a second computer network, by the communication interface, the motion data to a server;
    receiving over the second computer network, by the communication interface, from the server a particular time at which the motion data indicates a foot of the user experienced a loading force which risked adversely impacting an existing ulcer on the foot or risked causing a new ulcer on the foot;
    displaying to the user on a display the particular time and a geographic location of the motion sensor at the particular time;
    responsive to the foot of the user having experienced the loading force, causing displaying on the display a request that the user identify an activity engaged in by the user at the particular time and the geographic location; and
    transmitting over the second computer network the activity to the server for storage to a memory device in association with the particular time and the geographic location.

2. The non-transitory computer readable medium of claim 1, wherein the motion data is received from the motion sensor when the communication interface is no more than 100 meters from the motion sensor.

3. The non-transitory computer readable medium of claim 1, wherein the second computer network comprises a cellular network.

4. The non-transitory computer readable medium of claim 1, wherein the motion sensor comprises an accelerometer and a magnetometer, and the motion data comprises sensor data from the accelerometer and the magnetometer.

5. The non-transitory computer readable medium of claim 1, wherein the process comprises determining the geographic location from a physical location of the electronic device at the particular time.

6. The non-transitory computer readable medium of claim 5, wherein said determining comprises determining the physical location using a global positioning system (GPS) receiver or a communication received via the second computer network.

7. The non-transitory computer readable medium of claim 1, wherein said displaying comprises displaying the particular time and the geographic location together on the display.

8. The non-transitory computer readable medium of claim 1, wherein the particular time indicates when, based at least on the motion data, the foot experienced the loading force which risked adversely impacting the existing ulcer and the user is determined to have not been wearing an offloading device.

9. The non-transitory computer readable medium of claim 1, wherein the activity comprises a type of transportation, a type of exercise, a type of leisure, a type of home activity, or a type of work.

10. The non-transitory computer readable medium of claim 1, wherein the request comprises requesting that the user identify the activity from a plurality of different activity types previously indicated by the user to be types of activities commonly engaged in by the user.

11. The non-transitory computer readable medium of claim 1, wherein the process further comprises:
   permitting the display to accept a first type of input from the user during a time interval;
   responsive to the foot of the user having experienced the loading force, permitting the display to accept a second type of input from the user outside the time interval, the second type of input identifying the activity engaged in by the user at the particular time and the geographic location, and the second type of input being different from the first type of input; and
   locking out the display from accepting the first type of input from the user outside the time interval.

12. A method for gathering motion data from a motion sensor and processing event information associated with the motion data, the method comprising:
   receiving over a first computer network, by a communication interface, motion data from a motion sensor, the motion data being indicative of motion by a user while wearing the motion sensor;
   transmitting over a second computer network, by the communication interface, the motion data to a server;
   receiving over the second computer network, by the communication interface, from the server a particular time at which the motion data indicates a foot of the user experienced a loading force which risked adversely impacting an existing ulcer on the foot or risked causing a new ulcer on the foot;
   displaying to the user on a display the particular time and a geographic location of the motion sensor at the particular time;
   responsive to the foot of the user having experienced the loading force, causing displaying on the display a request that the user identify an activity engaged in by the user at the particular time and the geographic location; and
   transmitting over the second computer network the activity to the server for storage to a memory device in association with the particular time and the geographic location,
   wherein the method is performed under control of an electronic computing device.

13. The method of claim 12, wherein the motion data is received from the motion sensor when the communication interface is no more than 100 meters from the motion sensor.

14. The method of claim 11, wherein the second computer network comprises a cellular network.

15. The method of claim 12, wherein the motion sensor comprises an accelerometer and a magnetometer, and the motion data comprises sensor data from the accelerometer and the magnetometer.

16. The method of claim 12, further comprising determining the geographic location from a physical location of the electronic computing device at the particular time.

17. The method of claim 16, wherein said determining comprises determining the physical location using a global positioning system (GPS) receiver or a communication received via the second computer network.

18. The method of claim 12, wherein the particular time indicates when, based at least on the motion data, the foot experienced the loading force which risked adversely impacting the existing ulcer.

19. The method of claim 12, further comprising receiving the activity from the user via a user input.

20. The method of claim 12, wherein the activity comprises a type of transportation, a type of exercise, a type of leisure, a type of hobby, or a type of work.

21. The method of claim 12, wherein said requesting comprises requesting that the user identify the activity from a plurality of different activity types previously indicated by the user to be types of activities commonly engaged in by the user.

22. An apparatus for gathering motion data from a motion sensor and processing event information associated with the motion data, the apparatus comprising:
   a communication interface configured to communicate with a motion sensor and a server; and
   a processor configured to:
      receive over a first computer network motion data from the motion sensor, the motion data being indicative of motion by a user while wearing the motion sensor,
      transmit over a second computer network the motion data to the server,
      receive over the second computer network from the server a particular time at which the motion data indicates a foot of the user experienced a loading force which risked adversely impacting an existing ulcer on the foot or risked causing a new ulcer on the foot,
      output for presentation to the user the particular time and a geographic location of the motion sensor at the particular time,
      responsive to the foot of the user having experienced the loading force, cause output of a request that the user identify an activity engaged in by the user at the particular time and the geographic location, and
      transmit over the second computer network the activity to the server for storage to a memory device in association with the particular time and the geographic location.

23. The apparatus of claim 22, further comprising:
   a housing supporting the communication interface and the processor;
   a display configured to present the particular time and the geographic location; and
   a user input configured to receive the activity from the user.

* * * * *

UNITED STATES PATENT AND TRADEMARK OFFICE
CERTIFICATE OF CORRECTION

PATENT NO.        : 12,239,454 B2
APPLICATION NO.   : 17/607233
DATED             : March 4, 2025
INVENTOR(S)       : Jonathan Edward Mika Belding Page 1 of 1

It is certified that error appears in the above-identified patent and that said Letters Patent is hereby corrected as shown below:

In the Claims

In Column 39, Claim 14, Line 60 (Approx.), delete "of claim 11, wherein" and insert --of claim 12, wherein--.

In Column 40, Claim 21, Line 20, delete "said requesting comprises" and insert --said request comprises--.

Signed and Sealed this
Twenty-seventh Day of May, 2025

Coke Morgan Stewart
*Acting Director of the United States Patent and Trademark Office*